US012668826B2

(12) United States Patent
Mao et al.

(10) Patent No.: US 12,668,826 B2
(45) Date of Patent: Jun. 30, 2026

(54) BIOSYNTHETIC PRODUCTION OF VARIANT STEVIOL GLYCOSIDES

(71) Applicant: Conagen Inc., Bedford, MA (US)

(72) Inventors: Guohong Mao, Burlington, MA (US); Michael Batten, Westford, MA (US); Yang Luo, Wuxi Jiangsu (CN); Oliver Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 960 days.

(21) Appl. No.: 17/345,034

(22) Filed: Jun. 11, 2021

(65) Prior Publication Data

US 2021/0381019 A1 Dec. 9, 2021

Related U.S. Application Data

(63) Continuation of application No. PCT/US2019/066090, filed on Dec. 12, 2019.

(60) Provisional application No. 62/778,422, filed on Dec. 12, 2018.

(51) Int. Cl.

| | |
|---|---|
| ***C12P 19/56*** | (2006.01) |
| ***A23L 2/60*** | (2006.01) |
| ***A23L 27/30*** | (2016.01) |
| ***C07H 15/24*** | (2006.01) |
| ***C12N 9/10*** | (2006.01) |

(52) U.S. Cl.

CPC ................ *C12P 19/56* (2013.01); *A23L 2/60* (2013.01); *A23L 27/36* (2016.08); *C07H 15/24* (2013.01); *C12N 9/1051* (2013.01); *C12N 9/1062* (2013.01)

(58) Field of Classification Search

CPC . A23L 2/60; A23L 27/36; C07H 15/24; C12P 19/56; C12N 9/1051; C12N 9/1062

USPC ........................................................... 435/78

See application file for complete search history.

(56) References Cited

U.S. PATENT DOCUMENTS

| | | | |
|---|---|---|---|
| 9,522,929 | B2 | 12/2016 | Mao et al. |
| 2015/0031869 | A1 | 1/2015 | Markosyan et al. |

OTHER PUBLICATIONS

Kisselev L., (Structure, 2002, vol. 10: 8-9.*

Witkowski et al., (Biochemistry 38:11643-11650, 1999.*

Whisstock et al., (Quarterly Reviews of Biophysics 2003, vol. 36 (3): 307-340.*

Devos et al., (Proteins: Structure, Function and Genetics, 2000, vol. 41: 98-107.*

* cited by examiner

*Primary Examiner* — Tekchand Saidha
*Assistant Examiner* — Mohammad Y Meah
(74) *Attorney, Agent, or Firm* — Wolf, Greenfield & Sacks, P.C.

(57) ABSTRACT

The present invention relates to novel steviol glycosides R6-1, R6-2A, R6-2B, R6-4A, R6-4B and R7-2 and the production of these novel steviol glycosides, such as through enzymatic bioconversion. The use of these novel steviol glycosides as sweeteners and in orally consumable products are also provided.

11 Claims, 18 Drawing Sheets

Specification includes a Sequence Listing.

Reb D3

R6-2A

R6-2B

R7-2

Reb D

R6-1

Reb Z1

R6-4A

Reb Z2

R6-4B

R6-4A

R6-4B

SEQUENCE LISTING

```
<160> NUMBER OF SEQ ID NOS: 10

<210> SEQ ID NO 1
<211> LENGTH: 458
<212> TYPE: PRT
<213> ORGANISM: Stevia rebaudiana

<400> SEQUENCE: 1

Met Glu Asn Lys Thr Glu Thr Thr Val Arg Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
```

-continued

```
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455


<210> SEQ ID NO 2
<211> LENGTH: 1377
<212> TYPE: DNA
<213> ORGANISM: Artificial Sequence
<220> FEATURE:
<223> OTHER INFORMATION: Synthetic Polynucleotide

<400> SEQUENCE: 2

atggagaata agacagaaac aaccgtaaga cggaggcgga ggattatctt gttccctgta      60

ccatttcagg gccatattaa tccgatcctc caattagcaa acgtcctcta ctccaaggga     120

ttttcaataa caatcttcca tactaacttt aacaagccta aaacgagtaa ttatcctcac     180

tttacattca ggttcattct agacaacgac cctcaggatg agcgtatctc aaatttacct     240

acgcatggcc ccttggcagg tatgcgaata ccaataatca atgagcatgg agccgatgaa     300

ctccgtcgcg agttagagct tctcatgctc gcaagtgagg aagacgagga agtttcgtgc     360

ctaataactg atgcgctttg gtacttcgcc caatcagtcg cagactcact gaatctacgc     420

cgtttggtcc ttatgacaag ttcattattc aactttcacg cacatgtatc actgccgcaa     480

tttgacgagt tgggttacct ggacccggat gacaaaacgc gattggagga acaagcgtcg     540

ggcttcccca tgctgaaagt caaagatatt aagagcgctt atagtaattg gcaaattctg     600

aaagaaattc tcggaaaaat gataaagcaa accaaagcgt cctctggagt aatctggaac     660
```

-continued

```
tccttcaagg agttagagga atctgaactt gaaacggtca tcagagaaat ccccgctccc    720

tcgttcttaa ttccactacc caagcacctt actgcaagta gcagttccct cctagatcat    780

gaccgaaccg tgtttcagtg gctggatcag caaccccgt cgtcagttct atatgtaagc     840

tttgggagta cttcggaagt ggatgaaaag gacttcttag agattgcgcg agggctcgtg    900

gatagcaaac agagcttcct gtgggtagtg agaccgggat tcgttaaggg ctcgacgtgg    960

gtcgagccgt tgccagatgg ttttctaggg gagagaggga gaatcgtgaa atgggttcca   1020

cagcaagagg ttttggctca cggagctata ggggcctttt ggacccactc tggttggaat   1080

tctactcttg aaagtgtctg tgaaggcgtt ccaatgatat tttctgattt tgggcttgac   1140

cagcctctaa acgctcgcta tatgtctgat gtgttgaagg ttggcgtgta cctggagaat   1200

ggttgggaaa ggggggaaat tgccaacgcc atacgccggg taatggtgga cgaggaaggt   1260

gagtacatac gtcagaacgc tcgggtttta aaacaaaaag cggacgtcag ccttatgaag   1320

ggaggtagct cctatgaatc cctagaatcc ttggtaagct atatatcttc gttataa      1377
```

<210> SEQ ID NO 3
<211> LENGTH: 459
<212> TYPE: PRT
<213> ORGANISM: Hordeum vulgare

<400> SEQUENCE: 3

```
Met Asp Gly Asn Ser Ser Ser Ser Pro Leu His Val Val Ile Cys Pro
1               5                   10                  15

Trp Leu Ala Leu Gly His Leu Leu Pro Cys Leu Asp Ile Ala Glu Arg
            20                  25                  30

Leu Ala Ser Arg Gly His Arg Val Ser Phe Val Ser Thr Pro Arg Asn
        35                  40                  45

Ile Ala Arg Leu Pro Pro Leu Arg Pro Ala Val Ala Pro Leu Val Asp
    50                  55                  60

Phe Val Ala Leu Pro Leu Pro His Val Asp Gly Leu Pro Glu Gly Ala
65                  70                  75                  80

Glu Ser Thr Asn Asp Val Pro Tyr Asp Lys Phe Glu Leu His Arg Lys
                85                  90                  95

Ala Phe Asp Gly Leu Ala Ala Pro Phe Ser Glu Phe Leu Arg Ala Ala
            100                 105                 110

Cys Ala Glu Gly Ala Gly Ser Arg Pro Asp Trp Leu Ile Val Asp Thr
        115                 120                 125

Phe His His Trp Ala Ala Ala Ala Ala Val Glu Asn Lys Val Pro Cys
    130                 135                 140

Val Met Leu Leu Leu Gly Ala Ala Thr Val Ile Ala Gly Phe Ala Arg
145                 150                 155                 160

Gly Val Ser Glu His Ala Ala Ala Ala Val Gly Lys Glu Arg Pro Ala
                165                 170                 175

Ala Glu Ala Pro Ser Phe Glu Thr Glu Arg Arg Lys Leu Met Thr Thr
            180                 185                 190

Gln Asn Ala Ser Gly Met Thr Val Ala Glu Arg Tyr Phe Leu Thr Leu
        195                 200                 205

Met Arg Ser Asp Leu Val Ala Ile Arg Ser Cys Ala Glu Trp Glu Pro
    210                 215                 220

Glu Ser Val Ala Ala Leu Thr Thr Leu Ala Gly Lys Pro Val Val Pro
225                 230                 235                 240

Leu Gly Leu Leu Pro Pro Ser Pro Glu Gly Gly Arg Gly Val Ser Lys
                245                 250                 255
```

```
Glu Asp Ala Ala Val Arg Trp Leu Asp Ala Gln Pro Ala Lys Ser Val
            260                 265                 270

Val Tyr Val Ala Leu Gly Ser Glu Val Pro Leu Arg Ala Glu Gln Val
        275                 280                 285

His Glu Leu Ala Leu Gly Leu Glu Leu Ser Gly Ala Arg Phe Leu Trp
    290                 295                 300

Ala Leu Arg Lys Pro Thr Asp Ala Pro Asp Ala Ala Val Leu Pro Pro
305                 310                 315                 320

Gly Phe Glu Glu Arg Thr Arg Gly Arg Gly Leu Val Val Thr Gly Trp
                325                 330                 335

Val Pro Gln Ile Gly Val Leu Ala His Gly Ala Val Ala Ala Phe Leu
            340                 345                 350

Thr His Cys Gly Trp Asn Ser Thr Ile Glu Gly Leu Leu Phe Gly His
        355                 360                 365

Pro Leu Ile Met Leu Pro Ile Ser Ser Asp Gln Gly Pro Asn Ala Arg
    370                 375                 380

Leu Met Glu Gly Arg Lys Val Gly Met Gln Val Pro Arg Asp Glu Ser
385                 390                 395                 400

Asp Gly Ser Phe Arg Arg Glu Asp Val Ala Ala Thr Val Arg Ala Val
                405                 410                 415

Ala Val Glu Glu Asp Gly Arg Arg Val Phe Thr Ala Asn Ala Lys Lys
            420                 425                 430

Met Gln Glu Ile Val Ala Asp Gly Ala Cys His Glu Arg Cys Ile Asp
        435                 440                 445

Gly Phe Ile Gln Gln Leu Arg Ser Tyr Lys Ala
    450                 455
```

<210> SEQ ID NO 4
<211> LENGTH: 1380
<212> TYPE: DNA
<213> ORGANISM: Artificial Sequence
<220> FEATURE:
<223> OTHER INFORMATION: Synthetic polynucleotide

<400> SEQUENCE: 4

```
atggatggta actcctcctc ctcgccgctg catgtggtca tttgtccgtg gctggctctg      60

ggtcacctgc tgccgtgtct ggatattgct gaacgtctgg cgtcacgcgg ccatcgtgtc     120

agttttgtgt ccaccccgcg caacattgcc cgtctgccgc cgctgcgtcc ggctgttgca     180

ccgctggttg atttcgtcgc actgccgctg ccgcatgttg acggtctgcc ggagggtgcg     240

gaatcgacca atgatgtgcc gtatgacaaa tttgaactgc accgtaaggc gttcgatggt     300

ctggcggccc cgtttagcga atttctgcgt gcagcttgcg cagaaggtgc aggttctcgc     360

ccggattggc tgattgtgga cacctttcat cactgggcgg cggcggcggc ggtggaaaac     420

aaagtgccgt gtgttatgct gctgctgggt gcagcaacgg tgatcgctgg tttcgcgcgt     480

ggtgttagcg aacatgcggc ggcggcggtg ggtaaagaac gtccggctgc ggaagccccg     540

agttttgaaa ccgaacgtcg caagctgatg accacgcaga atgcctccgg catgaccgtg     600

gcagaacgct atttcctgac gctgatgcgt agcgatctgg ttgccatccg ctcttgcgca     660

gaatgggaac cggaaagcgt ggcagcactg accacgctgg caggtaaacc ggtggttccg     720

ctgggtctgc tgccgccgag tccggaaggc ggtcgtggcg tttccaaaga agatgctgcg     780

gtccgttggc tggacgcaca gccggcaaag tcagtcgtgt acgtcgcact gggttcggaa     840

gtgccgctgc gtgcggaaca agttcacgaa ctggcactgg gcctggaact gagcggtgct     900
```

-continued

```
cgctttctgt gggcgctgcg taaaccgacc gatgcaccgg acgccgcagt gctgccgccg    960

ggtttcgaag aacgtacccg cggccgtggt ctggttgtca cgggttgggt gccgcagatt   1020

ggcgttctgg ctcatggtgc ggtggctgcg tttctgaccc actgtggctg gaactctacg   1080

atcgaaggcc tgctgttcgg tcatccgctg attatgctgc cgatcagctc tgatcagggt   1140

ccgaatgcgc gcctgatgga aggccgtaaa gtcggtatgc aagtgccgcg tgatgaatca   1200

gacggctcgt ttcgtcgcga agatgttgcc gcaaccgtcc gcgccgtggc agttgaagaa   1260

gacggtcgtc gcgtcttcac ggctaacgcg aaaaagatgc aagaaattgt ggccgatggc   1320

gcatgccacg aacgttgtat tgacggtttt atccagcaac tgcgcagtta caaggcgtaa   1380


<210> SEQ ID NO 5
<211> LENGTH: 1268
<212> TYPE: PRT
<213> ORGANISM: Artificial Sequence
<220> FEATURE:
<223> OTHER INFORMATION: Synthetic Polypeptide

<400> SEQUENCE: 5

Met Glu Asn Lys Thr Glu Thr Thr Val Arg Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
```

-continued

```
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu Gly Ser Gly Ala Asn Ala
    450                 455                 460

Glu Arg Met Ile Thr Arg Val His Ser Gln Arg Glu Arg Leu Asn Glu
465                 470                 475                 480

Thr Leu Val Ser Glu Arg Asn Glu Val Leu Ala Leu Leu Ser Arg Val
                485                 490                 495

Glu Ala Lys Gly Lys Gly Ile Leu Gln Gln Asn Gln Ile Ile Ala Glu
            500                 505                 510

Phe Glu Ala Leu Pro Glu Gln Thr Arg Lys Lys Leu Glu Gly Gly Pro
        515                 520                 525

Phe Phe Asp Leu Leu Lys Ser Thr Gln Glu Ala Ile Val Leu Pro Pro
    530                 535                 540

Trp Val Ala Leu Ala Val Arg Pro Arg Pro Gly Val Trp Glu Tyr Leu
545                 550                 555                 560

Arg Val Asn Leu His Ala Leu Val Val Glu Glu Leu Gln Pro Ala Glu
                565                 570                 575

Phe Leu His Phe Lys Glu Glu Leu Val Asp Gly Val Lys Asn Gly Asn
            580                 585                 590

Phe Thr Leu Glu Leu Asp Phe Glu Pro Phe Asn Ala Ser Ile Pro Arg
        595                 600                 605

Pro Thr Leu His Lys Tyr Ile Gly Asn Gly Val Asp Phe Leu Asn Arg
    610                 615                 620

His Leu Ser Ala Lys Leu Phe His Asp Lys Glu Ser Leu Leu Pro Leu
625                 630                 635                 640

Leu Lys Phe Leu Arg Leu His Ser His Gln Gly Lys Asn Leu Met Leu
                645                 650                 655

Ser Glu Lys Ile Gln Asn Leu Asn Thr Leu Gln His Thr Leu Arg Lys
            660                 665                 670

Ala Glu Glu Tyr Leu Ala Glu Leu Lys Ser Glu Thr Leu Tyr Glu Glu
        675                 680                 685

Phe Glu Ala Lys Phe Glu Glu Ile Gly Leu Glu Arg Gly Trp Gly Asp
    690                 695                 700
```

```
Asn Ala Glu Arg Val Leu Asp Met Ile Arg Leu Leu Leu Asp Leu Leu
705                 710                 715                 720

Glu Ala Pro Asp Pro Cys Thr Leu Glu Thr Phe Leu Gly Arg Val Pro
                725                 730                 735

Met Val Phe Asn Val Val Ile Leu Ser Pro His Gly Tyr Phe Ala Gln
            740                 745                 750

Asp Asn Val Leu Gly Tyr Pro Asp Thr Gly Gly Gln Val Val Tyr Ile
        755                 760                 765

Leu Asp Gln Val Arg Ala Leu Glu Ile Glu Met Leu Gln Arg Ile Lys
    770                 775                 780

Gln Gln Gly Leu Asn Ile Lys Pro Arg Ile Leu Ile Leu Thr Arg Leu
785                 790                 795                 800

Leu Pro Asp Ala Val Gly Thr Thr Cys Gly Glu Arg Leu Glu Arg Val
                805                 810                 815

Tyr Asp Ser Glu Tyr Cys Asp Ile Leu Arg Val Pro Phe Arg Thr Glu
            820                 825                 830

Lys Gly Ile Val Arg Lys Trp Ile Ser Arg Phe Glu Val Trp Pro Tyr
        835                 840                 845

Leu Glu Thr Tyr Thr Glu Asp Ala Ala Val Glu Leu Ser Lys Glu Leu
    850                 855                 860

Asn Gly Lys Pro Asp Leu Ile Ile Gly Asn Tyr Ser Asp Gly Asn Leu
865                 870                 875                 880

Val Ala Ser Leu Leu Ala His Lys Leu Gly Val Thr Gln Cys Thr Ile
                885                 890                 895

Ala His Ala Leu Glu Lys Thr Lys Tyr Pro Asp Ser Asp Ile Tyr Trp
            900                 905                 910

Lys Lys Leu Asp Asp Lys Tyr His Phe Ser Cys Gln Phe Thr Ala Asp
        915                 920                 925

Ile Phe Ala Met Asn His Thr Asp Phe Ile Ile Thr Ser Thr Phe Gln
    930                 935                 940

Glu Ile Ala Gly Ser Lys Glu Thr Val Gly Gln Tyr Glu Ser His Thr
945                 950                 955                 960

Ala Phe Thr Leu Pro Gly Leu Tyr Arg Val Val His Gly Ile Asp Val
                965                 970                 975

Phe Asp Pro Lys Phe Asn Ile Val Ser Pro Gly Ala Asp Met Ser Ile
            980                 985                 990

Tyr Phe Pro Tyr Thr Glu Glu Lys  Arg Arg Leu Thr Lys  Phe His Ser
        995                 1000                1005

Glu Ile  Glu Glu Leu Leu Tyr  Ser Asp Val Glu Asn  Lys Glu His
    1010                1015                1020

Leu Cys  Val Leu Lys Asp Lys  Lys Lys Pro Ile Leu  Phe Thr Met
    1025                1030                1035

Ala Arg  Leu Asp Arg Val Lys  Asn Leu Ser Gly Leu  Val Glu Trp
    1040                1045                1050

Tyr Gly  Lys Asn Thr Arg Leu  Arg Glu Leu Ala Asn  Leu Val Val
    1055                1060                1065

Val Gly  Gly Asp Arg Arg Lys  Glu Ser Lys Asp Asn  Glu Glu Lys
    1070                1075                1080

Ala Glu  Met Lys Lys Met Tyr  Asp Leu Ile Glu Glu  Tyr Lys Leu
    1085                1090                1095

Asn Gly  Gln Phe Arg Trp Ile  Ser Ser Gln Met Asp  Arg Val Arg
    1100                1105                1110
```

-continued

```
Asn Gly  Glu Leu Tyr Arg Tyr  Ile Cys Asp Thr Lys  Gly Ala Phe
    1115                 1120                 1125

Val Gln  Pro Ala Leu Tyr Glu  Ala Phe Gly Leu Thr  Val Val Glu
    1130                 1135                 1140

Ala Met  Thr Cys Gly Leu Pro  Thr Phe Ala Thr Cys  Lys Gly Gly
    1145                 1150                 1155

Pro Ala  Glu Ile Ile Val His  Gly Lys Ser Gly Phe  His Ile Asp
    1160                 1165                 1170

Pro Tyr  His Gly Asp Gln Ala  Ala Asp Thr Leu Ala  Asp Phe Phe
    1175                 1180                 1185

Thr Lys  Cys Lys Glu Asp Pro  Ser His Trp Asp Glu  Ile Ser Lys
    1190                 1195                 1200

Gly Gly  Leu Gln Arg Ile Glu  Glu Lys Tyr Thr Trp  Gln Ile Tyr
    1205                 1210                 1215

Ser Gln  Arg Leu Leu Thr Leu  Thr Gly Val Tyr Gly  Phe Trp Lys
    1220                 1225                 1230

His Val  Ser Asn Leu Asp Arg  Leu Glu Ala Arg Arg  Tyr Leu Glu
    1235                 1240                 1245

Met Phe  Tyr Ala Leu Lys Tyr  Arg Pro Leu Ala Gln  Ala Val Pro
    1250                 1255                 1260

Leu Ala  Gln Asp Asp
    1265
```

<210> SEQ ID NO 6
<211> LENGTH: 3807
<212> TYPE: DNA
<213> ORGANISM: Artificial Sequence
<220> FEATURE:
<223> OTHER INFORMATION: Synthetic Polynucleotide

<400> SEQUENCE: 6

```
atggagaata agacagaaac aaccgtaaga cggaggcgga ggattatctt gttccctgta     60

ccatttcagg gccatattaa tccgatcctc caattagcaa acgtcctcta ctccaaggga    120

ttttcaataa caatcttcca tactaacttt aacaagccta aaacgagtaa ttatcctcac    180

tttacattca ggttcattct agacaacgac cctcaggatg agcgtatctc aaatttacct    240

acgcatggcc ccttggcagg tatgcgaata ccaataatca atgagcatgg agccgatgaa    300

ctccgtcgcg agttagagct tctcatgctc gcaagtgagg aagacgagga agtttcgtgc    360

ctaataactg atgcgctttg gtacttcgcc caatcagtcg cagactcact gaatctacgc    420

cgtttggtcc ttatgacaag ttcattattc aactttcacg cacatgtatc actgccgcaa    480

tttgacgagt tgggttacct ggacccggat gacaaaacgc gattggagga acaagcgtcg    540

ggcttcccca tgctgaaagt caaagatatt aagagcgctt atagtaattg gcaaattctg    600

aaagaaattc tcggaaaaat gataaagcaa accaaagcgt cctctggagt aatctggaac    660

tccttcaagg agttagagga atctgaactt gaaacggtca tcagagaaat ccccgctccc    720

tcgttcttaa ttccactacc caagcacctt actgcaagta gcagttccct cctagatcat    780

gaccgaaccg tgtttcagtg gctggatcag caaccccccgt cgtcagttct atatgtaagc    840

tttgggagta cttcggaagt ggatgaaaag gacttcttag agattgcgcg agggctcgtg    900

gatagcaaac agagcttcct gtgggtagtg agaccgggat tcgttaaggg ctcgacgtgg    960

gtcgagccgt tgccagatgg ttttctaggg gagagaggga gaatcgtgaa atgggttcca   1020

cagcaagagg ttttggctca cggagctata ggggcctttt ggacccactc tggttggaat   1080
```

-continued

```
tctactcttg aaagtgtctg tgaaggcgtt ccaatgatat tttctgattt tgggcttgac   1140
cagcctctaa acgctcgcta tatgtctgat gtgttgaagg ttggcgtgta cctggagaat   1200
ggttgggaaa gggggaaat tgccaacgcc atacgccggg taatggtgga cgaggaaggt   1260
gagtacatac gtcagaacgc tcgggtttta aaacaaaaag cggacgtcag ccttatgaag   1320
ggaggtagct cctatgaatc cctagaatcc ttggtaagct atatatcttc gttaggttct   1380
ggtgcaaacg ctgaacgtat gataacgcgc gtccacagcc aacgtgagcg tttgaacgaa   1440
acgcttgttt ctgagagaaa cgaagtcctt gccttgcttt ccagggttga agccaaaggt   1500
aaaggtattt tacaacaaaa ccagatcatt gctgaattcg aagctttgcc tgaacaaacc   1560
cggaagaaac ttgaaggtgg tcctttcttt gaccttctca aatccactca ggaagcaatt   1620
gtgttgccac catgggttgc tctagctgtg aggccaaggc ctggtgtttg ggaatactta   1680
cgagtcaatc tccatgctct tgtcgttgaa gaactccaac ctgctgagtt tcttcatttc   1740
aaggaagaac tcgttgatgg agttaagaat ggtaatttca ctcttgagct tgatttcgag   1800
ccattcaatg cgtctatccc tcgtccaaca ctccacaaat acattggaaa tggtgttgac   1860
ttccttaacc gtcatttatc ggctaagctc ttccatgaca aggagagttt gcttccattg   1920
cttaagttcc ttcgtcttca cagccaccag ggcaagaacc tgatgttgag cgagaagatt   1980
cagaacctca acactctgca acacaccttg aggaaagcag aagagtatct agcagagctt   2040
aagtccgaaa cactgtatga agagtttgag gccaagtttg aggagattgg tcttgagagg   2100
ggatggggag acaatgcaga gcgtgtcctt gacatgatac gtcttctttt ggaccttctt   2160
gaggcgcctg atccttgcac tcttgagact tttcttggaa gagtaccaat ggtgttcaac   2220
gttgtgatcc tctctccaca tggttacttt gctcaggaca atgttcttgg ttaccctgac   2280
actggtggac aggttgttta cattcttgat caagttcgtg ctctggagat agagatgctt   2340
caacgtatta agcaacaagg actcaacatt aaaccaagga ttctcattct aactcgactt   2400
ctacctgatg cggtaggaac tacatgcggt gaacgtctcg agagagttta tgattctgag   2460
tactgtgata ttcttcgtgt gcccttcaga acagagaagg gtattgttcg caaatggatc   2520
tcaaggttcg aagtctggcc atatctagag acttacaccg aggatgctgc ggttgagcta   2580
tcgaaagaat tgaatggcaa gcctgacctt atcattggta actacagtga tggaaatctt   2640
gttgcttctt tattggctca caaacttggt gtcactcagt gtaccattgc tcatgctctt   2700
gagaaaacaa agtacccgga ttctgatatc tactggaaga agcttgacga caagtaccat   2760
ttctcatgcc agttcactgc ggatattttc gcaatgaacc acactgattt catcatcact   2820
agtactttcc aagaaattgc tggaagcaaa gaaactgttg ggcagtatga aagccacaca   2880
gcctttactc ttcccggatt gtatcgagtt gttcacggga ttgatgtgtt tgatcccaag   2940
ttcaacattg tctctcctgg tgctgatatg agcatctact tcccttacac agaggagaag   3000
cgtagattga ctaagttcca ctctgagatc gaggagctcc tctacagcga tgttgagaac   3060
aaagagcact tatgtgtgct caaggacaag aagaagccga ttctcttcac aatggctagg   3120
cttgatcgtg tcaagaactt gtcaggtctt gttgagtggt acgggaagaa cacccgcttg   3180
cgtgagctag ctaacttggt tgttgttgga ggagacagga ggaaagagtc aaaggacaat   3240
gaagagaaag cagagatgaa gaaaatgtat gatctcattg aggaatacaa gctaaacggt   3300
cagttcaggt ggatctcctc tcagatggac cgggtaagga acggtgagct gtaccggtac   3360
atctgtgaca ccaagggtgc ttttgtccaa cctgcattat atgaagcctt tgggttaact   3420
gttgtggagg ctatgacttg tggtttaccg actttcgcca cttgcaaagg tggtccagct   3480
```

gagatcattg tgcacggtaa atcgggtttc cacattgacc cttaccatgg tgatcaggct 3540
gctgatactc ttgctgattt cttcaccaag tgtaaggagg atccatctca ctgggatgag 3600
atctcaaaag gagggcttca gaggattgag gagaaataca cttggcaaat ctattcacag 3660
aggctcttga cattgactgg tgtgtatgga ttctggaagc atgtctcgaa ccttgaccgt 3720
cttgaggctc gccgttacct tgaaatgttc tatgcattga agtatcgccc attggctcag 3780
gctgttcctc ttgcacaaga tgattga 3807

<210> SEQ ID NO 7
<211> LENGTH: 1269
<212> TYPE: PRT
<213> ORGANISM: Artificial Sequence
<220> FEATURE:
<223> OTHER INFORMATION: Synthetic Polypeptide

<400> SEQUENCE: 7

Met Asp Gly Asn Ser Ser Ser Ser Pro Leu His Val Val Ile Cys Pro
1 5 10 15

Trp Leu Ala Leu Gly His Leu Leu Pro Cys Leu Asp Ile Ala Glu Arg
20 25 30

Leu Ala Ser Arg Gly His Arg Val Ser Phe Val Ser Thr Pro Arg Asn
35 40 45

Ile Ala Arg Leu Pro Pro Leu Arg Pro Ala Val Ala Pro Leu Val Asp
50 55 60

Phe Val Ala Leu Pro Leu Pro His Val Asp Gly Leu Pro Glu Gly Ala
65 70 75 80

Glu Ser Thr Asn Asp Val Pro Tyr Asp Lys Phe Glu Leu His Arg Lys
85 90 95

Ala Phe Asp Gly Leu Ala Ala Pro Phe Ser Glu Phe Leu Arg Ala Ala
100 105 110

Cys Ala Glu Gly Ala Gly Ser Arg Pro Asp Trp Leu Ile Val Asp Thr
115 120 125

Phe His His Trp Ala Ala Ala Ala Ala Val Glu Asn Lys Val Pro Cys
130 135 140

Val Met Leu Leu Leu Gly Ala Ala Thr Val Ile Ala Gly Phe Ala Arg
145 150 155 160

Gly Val Ser Glu His Ala Ala Ala Ala Val Gly Lys Glu Arg Pro Ala
165 170 175

Ala Glu Ala Pro Ser Phe Glu Thr Glu Arg Arg Lys Leu Met Thr Thr
180 185 190

Gln Asn Ala Ser Gly Met Thr Val Ala Glu Arg Tyr Phe Leu Thr Leu
195 200 205

Met Arg Ser Asp Leu Val Ala Ile Arg Ser Cys Ala Glu Trp Glu Pro
210 215 220

Glu Ser Val Ala Ala Leu Thr Thr Leu Ala Gly Lys Pro Val Val Pro
225 230 235 240

Leu Gly Leu Leu Pro Pro Ser Pro Glu Gly Gly Arg Gly Val Ser Lys
245 250 255

Glu Asp Ala Ala Val Arg Trp Leu Asp Ala Gln Pro Ala Lys Ser Val
260 265 270

Val Tyr Val Ala Leu Gly Ser Glu Val Pro Leu Arg Ala Glu Gln Val
275 280 285

His Glu Leu Ala Leu Gly Leu Glu Leu Ser Gly Ala Arg Phe Leu Trp
290 295 300

-continued

```
Ala Leu Arg Lys Pro Thr Asp Ala Pro Asp Ala Ala Val Leu Pro Pro
305                 310                 315                 320

Gly Phe Glu Glu Arg Thr Arg Gly Arg Gly Leu Val Val Thr Gly Trp
                325                 330                 335

Val Pro Gln Ile Gly Val Leu Ala His Gly Ala Val Ala Ala Phe Leu
            340                 345                 350

Thr His Cys Gly Trp Asn Ser Thr Ile Glu Gly Leu Leu Phe Gly His
        355                 360                 365

Pro Leu Ile Met Leu Pro Ile Ser Ser Asp Gln Gly Pro Asn Ala Arg
    370                 375                 380

Leu Met Glu Gly Arg Lys Val Gly Met Gln Val Pro Arg Asp Glu Ser
385                 390                 395                 400

Asp Gly Ser Phe Arg Arg Glu Asp Val Ala Ala Thr Val Arg Ala Val
                405                 410                 415

Ala Val Glu Glu Asp Gly Arg Arg Val Phe Thr Ala Asn Ala Lys Lys
            420                 425                 430

Met Gln Glu Ile Val Ala Asp Gly Ala Cys His Glu Arg Cys Ile Asp
        435                 440                 445

Gly Phe Ile Gln Gln Leu Arg Ser Tyr Lys Ala Gly Ser Gly Ala Asn
    450                 455                 460

Ala Glu Arg Met Ile Thr Arg Val His Ser Gln Arg Glu Arg Leu Asn
465                 470                 475                 480

Glu Thr Leu Val Ser Glu Arg Asn Glu Val Leu Ala Leu Leu Ser Arg
                485                 490                 495

Val Glu Ala Lys Gly Lys Gly Ile Leu Gln Gln Asn Gln Ile Ile Ala
            500                 505                 510

Glu Phe Glu Ala Leu Pro Glu Gln Thr Arg Lys Lys Leu Glu Gly Gly
        515                 520                 525

Pro Phe Phe Asp Leu Leu Lys Ser Thr Gln Glu Ala Ile Val Leu Pro
    530                 535                 540

Pro Trp Val Ala Leu Ala Val Arg Pro Arg Pro Gly Val Trp Glu Tyr
545                 550                 555                 560

Leu Arg Val Asn Leu His Ala Leu Val Val Glu Glu Leu Gln Pro Ala
                565                 570                 575

Glu Phe Leu His Phe Lys Glu Glu Leu Val Asp Gly Val Lys Asn Gly
            580                 585                 590

Asn Phe Thr Leu Glu Leu Asp Phe Glu Pro Phe Asn Ala Ser Ile Pro
        595                 600                 605

Arg Pro Thr Leu His Lys Tyr Ile Gly Asn Gly Val Asp Phe Leu Asn
    610                 615                 620

Arg His Leu Ser Ala Lys Leu Phe His Asp Lys Glu Ser Leu Leu Pro
625                 630                 635                 640

Leu Leu Lys Phe Leu Arg Leu His Ser His Gln Gly Lys Asn Leu Met
                645                 650                 655

Leu Ser Glu Lys Ile Gln Asn Leu Asn Thr Leu Gln His Thr Leu Arg
            660                 665                 670

Lys Ala Glu Glu Tyr Leu Ala Glu Leu Lys Ser Glu Thr Leu Tyr Glu
        675                 680                 685

Glu Phe Glu Ala Lys Phe Glu Glu Ile Gly Leu Glu Arg Gly Trp Gly
    690                 695                 700

Asp Asn Ala Glu Arg Val Leu Asp Met Ile Arg Leu Leu Leu Asp Leu
705                 710                 715                 720
```

-continued

```
Leu Glu Ala Pro Asp Pro Cys Thr Leu Glu Thr Phe Leu Gly Arg Val
                725                 730                 735

Pro Met Val Phe Asn Val Val Ile Leu Ser Pro His Gly Tyr Phe Ala
            740                 745                 750

Gln Asp Asn Val Leu Gly Tyr Pro Asp Thr Gly Gly Gln Val Val Tyr
        755                 760                 765

Ile Leu Asp Gln Val Arg Ala Leu Glu Ile Glu Met Leu Gln Arg Ile
    770                 775                 780

Lys Gln Gln Gly Leu Asn Ile Lys Pro Arg Ile Leu Ile Leu Thr Arg
785                 790                 795                 800

Leu Leu Pro Asp Ala Val Gly Thr Thr Cys Gly Glu Arg Leu Glu Arg
                805                 810                 815

Val Tyr Asp Ser Glu Tyr Cys Asp Ile Leu Arg Val Pro Phe Arg Thr
            820                 825                 830

Glu Lys Gly Ile Val Arg Lys Trp Ile Ser Arg Phe Glu Val Trp Pro
        835                 840                 845

Tyr Leu Glu Thr Tyr Thr Glu Asp Ala Ala Val Glu Leu Ser Lys Glu
    850                 855                 860

Leu Asn Gly Lys Pro Asp Leu Ile Ile Gly Asn Tyr Ser Asp Gly Asn
865                 870                 875                 880

Leu Val Ala Ser Leu Leu Ala His Lys Leu Gly Val Thr Gln Cys Thr
                885                 890                 895

Ile Ala His Ala Leu Glu Lys Thr Lys Tyr Pro Asp Ser Asp Ile Tyr
            900                 905                 910

Trp Lys Lys Leu Asp Asp Lys Tyr His Phe Ser Cys Gln Phe Thr Ala
        915                 920                 925

Asp Ile Phe Ala Met Asn His Thr Asp Phe Ile Ile Thr Ser Thr Phe
    930                 935                 940

Gln Glu Ile Ala Gly Ser Lys Glu Thr Val Gly Gln Tyr Glu Ser His
945                 950                 955                 960

Thr Ala Phe Thr Leu Pro Gly Leu Tyr Arg Val Val His Gly Ile Asp
                965                 970                 975

Val Phe Asp Pro Lys Phe Asn Ile Val Ser Pro Gly Ala Asp Met Ser
            980                 985                 990

Ile Tyr Phe Pro Tyr Thr Glu Glu  Lys Arg Arg Leu Thr  Lys Phe His
        995                 1000                1005

Ser Glu  Ile Glu Glu Leu Leu  Tyr Ser Asp Val Glu  Asn Lys Glu
    1010                1015                1020

His Leu  Cys Val Leu Lys Asp  Lys Lys Lys Pro Ile  Leu Phe Thr
    1025                1030                1035

Met Ala  Arg Leu Asp Arg Val  Lys Asn Leu Ser Gly  Leu Val Glu
    1040                1045                1050

Trp Tyr  Gly Lys Asn Thr Arg  Leu Arg Glu Leu Ala  Asn Leu Val
    1055                1060                1065

Val Val  Gly Gly Asp Arg Arg  Lys Glu Ser Lys Asp  Asn Glu Glu
    1070                1075                1080

Lys Ala  Glu Met Lys Lys Met  Tyr Asp Leu Ile Glu  Glu Tyr Lys
    1085                1090                1095

Leu Asn  Gly Gln Phe Arg Trp  Ile Ser Ser Gln Met  Asp Arg Val
    1100                1105                1110

Arg Asn  Gly Glu Leu Tyr Arg  Tyr Ile Cys Asp Thr  Lys Gly Ala
    1115                1120                1125

Phe Val  Gln Pro Ala Leu Tyr  Glu Ala Phe Gly Leu  Thr Val Val
```

```
    1130                1135                1140

Glu Ala  Met Thr Cys Gly Leu  Pro Thr Phe Ala Thr  Cys Lys Gly
    1145                1150                1155

Gly Pro  Ala Glu Ile Ile Val  His Gly Lys Ser Gly  Phe His Ile
    1160                1165                1170

Asp Pro  Tyr His Gly Asp Gln  Ala Ala Asp Thr Leu  Ala Asp Phe
    1175                1180                1185

Phe Thr  Lys Cys Lys Glu Asp  Pro Ser His Trp Asp  Glu Ile Ser
    1190                1195                1200

Lys Gly  Gly Leu Gln Arg Ile  Glu Glu Lys Tyr Thr  Trp Gln Ile
    1205                1210                1215

Tyr Ser  Gln Arg Leu Leu Thr  Leu Thr Gly Val Tyr  Gly Phe Trp
    1220                1225                1230

Lys His  Val Ser Asn Leu Asp  Arg Leu Glu Ala Arg  Arg Tyr Leu
    1235                1240                1245

Glu Met  Phe Tyr Ala Leu Lys  Tyr Arg Pro Leu Ala  Gln Ala Val
    1250                1255                1260

Pro Leu  Ala Gln Asp Asp
    1265


<210> SEQ ID NO 8
<211> LENGTH: 3810
<212> TYPE: DNA
<213> ORGANISM: Artificial Sequence
<220> FEATURE:
<223> OTHER INFORMATION: Synthetic Polynucleotide

<400> SEQUENCE: 8

atggatggta actcctcctc ctcgccgctg catgtggtca tttgtccgtg gctggctctg     60

ggtcacctgc tgccgtgtct ggatattgct gaacgtctgg cgtcacgcgg ccatcgtgtc    120

agttttgtgt ccaccccgcg caacattgcc cgtctgccgc cgctgcgtcc ggctgttgca    180

ccgctggttg atttcgtcgc actgccgctg ccgcatgttg acggtctgcc ggagggtgcg    240

gaatcgacca atgatgtgcc gtatgacaaa tttgaactgc accgtaaggc gttcgatggt    300

ctggcggccc cgtttagcga atttctgcgt gcagcttgcg cagaaggtgc aggttctcgc    360

ccggattggc tgattgtgga cacctttcat cactgggcgg cggcggcggc ggtggaaaac    420

aaagtgccgt gtgttatgct gctgctgggt gcagcaacgg tgatcgctgg tttcgcgcgt    480

ggtgttagcg aacatgcggc ggcggcggtg ggtaaagaac gtccggctgc ggaagccccg    540

agttttgaaa ccgaacgtcg caagctgatg accacgcaga atgcctccgg catgaccgtg    600

gcagaacgct atttcctgac gctgatgcgt agcgatctgg ttgccatccg ctcttgcgca    660

gaatgggaac cggaaagcgt ggcagcactg accacgctgg caggtaaacc ggtggttccg    720

ctgggtctgc tgccgccgag tccggaaggc ggtcgtggcg tttccaaaga agatgctgcg    780

gtccgttggc tggacgcaca gccggcaaag tcagtcgtgt acgtcgcact gggttcggaa    840

gtgccgctgc gtgcggaaca agttcacgaa ctggcactgg gcctggaact gagcggtgct    900

cgctttctgt gggcgctgcg taaaccgacc gatgcaccgg acgccgcagt gctgccgccg    960

ggtttcgaag aacgtacccg cggccgtggt ctggttgtca cgggttgggt gccgcagatt   1020

ggcgttctgg ctcatggtgc ggtggctgcg tttctgaccc actgtggctg gaactctacg   1080

atcgaaggcc tgctgttcgg tcatccgctg attatgctgc cgatcagctc tgatcagggt   1140

ccgaatgcgc gcctgatgga aggccgtaaa gtcggtatgc aagtgccgcg tgatgaatca   1200
```

-continued

```
gacggctcgt ttcgtcgcga agatgttgcc gcaaccgtcc gcgccgtggc agttgaagaa   1260
gacggtcgtc gcgtcttcac ggctaacgcg aaaaagatgc aagaaattgt ggccgatggc   1320
gcatgccacg aacgttgtat tgacggtttt atccagcaac tgcgcagtta caaggcgggt   1380
tctggtgcaa acgctgaacg tatgataacg cgcgtccaca gccaacgtga gcgtttgaac   1440
gaaacgcttg tttctgagag aaacgaagtc cttgccttgc tttccagggt tgaagccaaa   1500
ggtaaaggta ttttacaaca aaaccagatc attgctgaat tcgaagcttt gcctgaacaa   1560
acccggaaga aacttgaagg tggtcctttc tttgaccttc tcaaatccac tcaggaagca   1620
attgtgttgc caccatgggt tgctctagct gtgaggccaa ggcctggtgt ttgggaatac   1680
ttacgagtca atctccatgc tcttgtcgtt gaagaactcc aacctgctga gtttcttcat   1740
ttcaaggaag aactcgttga tggagttaag aatggtaatt tcactcttga gcttgatttc   1800
gagccattca atgcgtctat ccctcgtcca acactccaca aatacattgg aaatggtgtt   1860
gacttcctta accgtcattt atcggctaag ctcttccatg acaaggagag tttgcttcca   1920
ttgcttaagt tccttcgtct tcacagccac cagggcaaga acctgatgtt gagcgagaag   1980
attcagaacc tcaacactct gcaacacacc ttgaggaaag cagaagagta tctagcagag   2040
cttaagtccg aaacactgta tgaagagttt gaggccaagt ttgaggagat tggtcttgag   2100
aggggatggg gagacaatgc agagcgtgtc cttgacatga tacgtcttct tttggacctt   2160
cttgaggcgc ctgatccttg cactcttgag actttttcttg gaagagtacc aatggtgttc   2220
aacgttgtga tcctctctcc acatggttac tttgctcagg acaatgttct tggttaccct   2280
gacactggtg gacaggttgt ttacattctt gatcaagttc gtgctctgga gatagagatg   2340
cttcaacgta ttaagcaaca aggactcaac attaaaccaa ggattctcat tctaactcga   2400
cttctacctg atgcggtagg aactacatgc ggtgaacgtc tcgagagagt ttatgattct   2460
gagtactgtg atattcttcg tgtgcccttc agaacagaga agggtattgt tcgcaaatgg   2520
atctcaaggt tcgaagtctg gccatatcta gagacttaca ccgaggatgc tgcggttgag   2580
ctatcgaaag aattgaatgg caagcctgac cttatcattg gtaactacag tgatggaaat   2640
cttgttgctt ctttattggc tcacaaactt ggtgtcactc agtgtaccat tgctcatgct   2700
cttgagaaaa caaagtaccc ggattctgat atctactgga agaagcttga cgacaagtac   2760
catttctcat gccagttcac tgcggatatt ttcgcaatga accacactga tttcatcatc   2820
actagtactt tccaagaaat tgctggaagc aaagaaactg ttgggcagta tgaaagccac   2880
acagccttta ctcttcccgg attgtatcga gttgttcacg ggattgatgt gtttgatccc   2940
aagttcaaca ttgtctctcc tggtgctgat atgagcatct acttccctta cacagaggag   3000
aagcgtagat tgactaagtt ccactctgag atcgaggagc tcctctacag cgatgttgag   3060
aacaaagagc acttatgtgt gctcaaggac aagaagaagc cgattctctt cacaatggct   3120
aggcttgatc gtgtcaagaa cttgtcaggt cttgttgagt ggtacgggaa gaacacccgc   3180
ttgcgtgagc tagctaactt ggttgttgtt ggaggagaca ggaggaaaga gtcaaaggac   3240
aatgaagaga aagcagagat gaagaaaatg tatgatctca ttgaggaata caagctaaac   3300
ggtcagttca ggtggatctc ctctcagatg gaccgggtaa ggaacggtga gctgtaccgg   3360
tacatctgtg acaccaaggg tgcttttgtc caacctgcat tatatgaagc ctttgggtta   3420
actgttgtgg aggctatgac ttgtggttta ccgactttcg ccacttgcaa aggtggtcca   3480
gctgagatca ttgtgcacgg taaatcgggt ttccacattg acccttacca tggtgatcag   3540
gctgctgata ctcttgctga tttcttcacc aagtgtaagg aggatccatc tcactgggat   3600
```

```
gagatctcaa aaggagggct tcagaggatt gaggagaaat acacttggca aatctattca   3660

cagaggctct tgacattgac tggtgtgtat ggattctgga agcatgtctc gaaccttgac   3720

cgtcttgagg ctcgccgtta ccttgaaatg ttctatgcat tgaagtatcg cccattggct   3780

caggctgttc ctcttgcaca agatgattaa                                    3810


<210> SEQ ID NO 9
<211> LENGTH: 808
<212> TYPE: PRT
<213> ORGANISM: Arabidopsis thaliana

<400> SEQUENCE: 9

Met Ala Asn Ala Glu Arg Met Ile Thr Arg Val His Ser Gln Arg Glu
1               5                   10                  15

Arg Leu Asn Glu Thr Leu Val Ser Glu Arg Asn Glu Val Leu Ala Leu
            20                  25                  30

Leu Ser Arg Val Glu Ala Lys Gly Lys Gly Ile Leu Gln Gln Asn Gln
        35                  40                  45

Ile Ile Ala Glu Phe Glu Ala Leu Pro Glu Gln Thr Arg Lys Lys Leu
    50                  55                  60

Glu Gly Gly Pro Phe Phe Asp Leu Leu Lys Ser Thr Gln Glu Ala Ile
65                  70                  75                  80

Val Leu Pro Pro Trp Val Ala Leu Ala Val Arg Pro Arg Pro Gly Val
                85                  90                  95

Trp Glu Tyr Leu Arg Val Asn Leu His Ala Leu Val Val Glu Glu Leu
            100                 105                 110

Gln Pro Ala Glu Phe Leu His Phe Lys Glu Glu Leu Val Asp Gly Val
        115                 120                 125

Lys Asn Gly Asn Phe Thr Leu Glu Leu Asp Phe Glu Pro Phe Asn Ala
    130                 135                 140

Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
                165                 170                 175

Leu Leu Pro Leu Leu Lys Phe Leu Arg Leu His Ser His Gln Gly Lys
            180                 185                 190

Asn Leu Met Leu Ser Glu Lys Ile Gln Asn Leu Asn Thr Leu Gln His
        195                 200                 205

Thr Leu Arg Lys Ala Glu Glu Tyr Leu Ala Glu Leu Lys Ser Glu Thr
    210                 215                 220

Leu Tyr Glu Glu Phe Glu Ala Lys Phe Glu Glu Ile Gly Leu Glu Arg
225                 230                 235                 240

Gly Trp Gly Asp Asn Ala Glu Arg Val Leu Asp Met Ile Arg Leu Leu
                245                 250                 255

Leu Asp Leu Leu Glu Ala Pro Asp Pro Cys Thr Leu Glu Thr Phe Leu
            260                 265                 270

Gly Arg Val Pro Met Val Phe Asn Val Val Ile Leu Ser Pro His Gly
        275                 280                 285

Tyr Phe Ala Gln Asp Asn Val Leu Gly Tyr Pro Asp Thr Gly Gly Gln
    290                 295                 300

Val Val Tyr Ile Leu Asp Gln Val Arg Ala Leu Glu Ile Glu Met Leu
305                 310                 315                 320

Gln Arg Ile Lys Gln Gln Gly Leu Asn Ile Lys Pro Arg Ile Leu Ile
                325                 330                 335
```

-continued

```
Leu Thr Arg Leu Leu Pro Asp Ala Val Gly Thr Thr Cys Gly Glu Arg
            340                 345                 350

Leu Glu Arg Val Tyr Asp Ser Glu Tyr Cys Asp Ile Leu Arg Val Pro
        355                 360                 365

Phe Arg Thr Glu Lys Gly Ile Val Arg Lys Trp Ile Ser Arg Phe Glu
    370                 375                 380

Val Trp Pro Tyr Leu Glu Thr Tyr Thr Glu Asp Ala Ala Val Glu Leu
385                 390                 395                 400

Ser Lys Glu Leu Asn Gly Lys Pro Asp Leu Ile Ile Gly Asn Tyr Ser
                405                 410                 415

Asp Gly Asn Leu Val Ala Ser Leu Leu Ala His Lys Leu Gly Val Thr
            420                 425                 430

Gln Cys Thr Ile Ala His Ala Leu Glu Lys Thr Lys Tyr Pro Asp Ser
        435                 440                 445

Asp Ile Tyr Trp Lys Lys Leu Asp Asp Lys Tyr His Phe Ser Cys Gln
    450                 455                 460

Phe Thr Ala Asp Ile Phe Ala Met Asn His Thr Asp Phe Ile Ile Thr
465                 470                 475                 480

Ser Thr Phe Gln Glu Ile Ala Gly Ser Lys Glu Thr Val Gly Gln Tyr
                485                 490                 495

Glu Ser His Thr Ala Phe Thr Leu Pro Gly Leu Tyr Arg Val Val His
            500                 505                 510

Gly Ile Asp Val Phe Asp Pro Lys Phe Asn Ile Val Ser Pro Gly Ala
        515                 520                 525

Asp Met Ser Ile Tyr Phe Pro Tyr Thr Glu Glu Lys Arg Arg Leu Thr
    530                 535                 540

Lys Phe His Ser Glu Ile Glu Glu Leu Leu Tyr Ser Asp Val Glu Asn
545                 550                 555                 560

Lys Glu His Leu Cys Val Leu Lys Asp Lys Lys Lys Pro Ile Leu Phe
                565                 570                 575

Thr Met Ala Arg Leu Asp Arg Val Lys Asn Leu Ser Gly Leu Val Glu
            580                 585                 590

Trp Tyr Gly Lys Asn Thr Arg Leu Arg Glu Leu Ala Asn Leu Val Val
        595                 600                 605

Val Gly Gly Asp Arg Arg Lys Glu Ser Lys Asp Asn Glu Glu Lys Ala
    610                 615                 620

Glu Met Lys Lys Met Tyr Asp Leu Ile Glu Glu Tyr Lys Leu Asn Gly
625                 630                 635                 640

Gln Phe Arg Trp Ile Ser Ser Gln Met Asp Arg Val Arg Asn Gly Glu
                645                 650                 655

Leu Tyr Arg Tyr Ile Cys Asp Thr Lys Gly Ala Phe Val Gln Pro Ala
            660                 665                 670

Leu Tyr Glu Ala Phe Gly Leu Thr Val Val Glu Ala Met Thr Cys Gly
        675                 680                 685

Leu Pro Thr Phe Ala Thr Cys Lys Gly Gly Pro Ala Glu Ile Ile Val
    690                 695                 700

His Gly Lys Ser Gly Phe His Ile Asp Pro Tyr His Gly Asp Gln Ala
705                 710                 715                 720

Ala Asp Thr Leu Ala Asp Phe Phe Thr Lys Cys Lys Glu Asp Pro Ser
                725                 730                 735

His Trp Asp Glu Ile Ser Lys Gly Gly Leu Gln Arg Ile Glu Glu Lys
            740                 745                 750
```

-continued

```
Tyr Thr Trp Gln Ile Tyr Ser Gln Arg Leu Leu Thr Leu Thr Gly Val
        755                 760                 765

Tyr Gly Phe Trp Lys His Val Ser Asn Leu Asp Arg Leu Glu Ala Arg
    770                 775                 780

Arg Tyr Leu Glu Met Phe Tyr Ala Leu Lys Tyr Arg Pro Leu Ala Gln
785                 790                 795                 800

Ala Val Pro Leu Ala Gln Asp Asp
                805
```

```
<210> SEQ ID NO 10
<211> LENGTH: 2427
<212> TYPE: DNA
<213> ORGANISM: Arabidopsis thaliana

<400> SEQUENCE: 10

atggcaaacg ctgaacgtat gattacccgt gtccactccc aacgcgaacg cctgaacgaa     60

accctggtgt cggaacgcaa cgaagttctg gcactgctga gccgtgtgga agctaagggc    120

aaaggtattc tgcagcaaaa ccagattatc gcggaatttg aagccctgcc ggaacaaacc    180

cgcaaaaagc tggaaggcgg tccgtttttc gatctgctga aatctacgca ggaagcgatc    240

gttctgccgc cgtgggtcgc actggcagtg cgtccgcgtc cgggcgtttg ggaatatctg    300

cgtgtcaacc tgcatgcact ggtggttgaa gaactgcagc cggctgaatt tctgcacttc    360

aaggaagaac tggttgacgg cgtcaaaaac ggtaatttta ccctggaact ggattttgaa    420

ccgttcaatg ccagtatccc gcgtccgacg ctgcataaat atattggcaa cggtgtggac    480

tttctgaatc gccatctgag cgcaaagctg ttccacgata aagaatctct gctgccgctg    540

ctgaaattcc tgcgtctgca tagtcaccag ggcaagaacc tgatgctgtc cgaaaaaatt    600

cagaacctga ataccctgca acacacgctg cgcaaggcgg aagaatacct ggccgaactg    660

aaaagtgaaa ccctgtacga agaattcgaa gcaaagttcg aagaaattgg cctggaacgt    720

ggctggggtg acaatgctga acgtgttctg gatatgatcc gtctgctgct ggacctgctg    780

gaagcaccgg acccgtgcac cctggaaacg tttctgggtc gcgtgccgat ggttttcaac    840

gtcgtgattc tgtccccgca tggctatttt gcacaggaca atgtgctggg ttacccggat    900

accggcggtc aggttgtcta tattctggat caagttcgtg cgctggaaat tgaaatgctg    960

cagcgcatca agcagcaagg cctgaacatc aaaccgcgta ttctgatcct gacccgtctg   1020

ctgccggatg cagttggtac cacgtgcggt gaacgtctgg aacgcgtcta tgacagcgaa   1080

tactgtgata ttctgcgtgt cccgtttcgc accgaaaagg gtattgtgcg taaatggatc   1140

agtcgcttcg aagtttggcc gtatctggaa acctacacgg aagatgcggc cgtggaactg   1200

tccaaggaac tgaatggcaa accggacctg attatcggca actatagcga tggtaatctg   1260

gtcgcatctc tgctggctca taaactgggt gtgacccagt gcacgattgc acacgctctg   1320

gaaaagacca aatatccgga ttcagacatc tactggaaaa agctggatga caaatatcat   1380

ttttcgtgtc agttcaccgc ggacattttt gccatgaacc acacggattt tattatcacc   1440

agtacgttcc aggaaatcgc gggctccaaa gaaaccgtgg gtcaatacga atcacatacc   1500
```

-continued

```
gccttcacgc tgccgggcct gtatcgtgtg gttcacggta tcgatgtttt tgacccgaaa   1560
ttcaatattg tcagtccggg cgcggatatg tccatctatt ttccgtacac cgaagaaaag   1620
cgtcgcctga cgaaattcca ttcagaaatt gaagaactgc tgtactcgga cgtggaaaac   1680
aaggaacacc tgtgtgttct gaaagataaa aagaaaccga tcctgtttac catggcccgt   1740
ctggatcgcg tgaagaatct gtcaggcctg gttgaatggt atggtaaaaa cacgcgtctg   1800
cgcgaactgg caaatctggt cgtggttggc ggtgaccgtc gcaaggaatc gaaagataac   1860
gaagaaaagg ctgaaatgaa gaaaatgtac gatctgatcg aagaatacaa gctgaacggc   1920
cagtttcgtt ggatcagctc tcaaatggac cgtgtgcgca atggcgaact gtatcgctac   1980
atttgcgata ccaagggtgc gtttgttcag ccggcactgt acgaagcttt cggcctgacc   2040
gtcgtggaag ccatgacgtg cggtctgccg acctttgcga cgtgtaaagg cggtccggcc   2100
gaaattatcg tgcatggcaa atctggtttc catatcgatc cgtatcacgg tgatcaggca   2160
gctgacaccc tggcggattt ctttacgaag tgtaaagaag acccgtcaca ctgggatgaa   2220
atttcgaagg gcggtctgca acgtatcgaa gaaaaatata cctggcagat ttacagccaa   2280
cgcctgctga ccctgacggg cgtctacggt ttttggaaac atgtgtctaa tctggatcgc   2340
ctggaagccc gtcgctatct ggaaatgttt tacgcactga agtatcgccc gctggcacaa   2400
gccgttccgc tggcacagga cgactaa                                       2427
```

BIOSYNTHETIC PRODUCTION OF VARIANT STEVIOL GLYCOSIDES

RELATED APPLICATION

This application is a continuation of International Patent Application No. PCT/US2019/066090, filed Dec. 12, 2019, entitled "BIOSYNTHETIC PRODUCTION OF VARIANT STEVIOL GLYCOSIDES", which claims the benefit under 35 U.S.C. § 119 (e) to U.S. Provisional Patent Application No. 62/778,422, filed Dec. 12, 2018, entitled "BIOSYNTHETIC PRODUCTION OF VARIANT STEVIOL GLYCOSIDES". The contents of which are incorporated herein by reference in their entirety.

FIELD OF THE INVENTION

The field of the invention relates to methods and processes useful in the production of several specific steviol glycosides via enzymatic conversion as well as related compositions.

BACKGROUND

Several steviol glycosides are found as compounds in *Stevia rebaudiana* leaves, and several of them have been widely used as high intensity, low-calorie sweeteners in food, feed and beverages. These naturally occurring steviol glycosides have the same basic diterpene structure (steviol backbone) but differ in the number and structure of their carbohydrate residue modifications (e.g. glucose, rhamnose, and xylose residues) at the C13 and C19 positions of the steviol backbone. Interestingly, these changes in sugar 'ornamentation' of the base steviol structure can affect the properties of the individual steviol glycosides themselves. These properties can include, without limitation: the taste profile, crystallization point, solubility, mouth feel and perceived sweetness among other differences. Steviol glycosides with known structures include stevioside, rebaudioside A, rebaudioside B, rebaudioside C, rebaudioside D, rebaudioside E, rebaudioside I, rebaudioside M, rebaudioside D3, rebaudioside N and rebaudioside O. In terms of commercial use rebaudiosides D and M have become generally regarded as safe (that is, it has 'GRAS' status) and are being studied for a wide range of uses in the food and beverage markets.

On a dry weight basis, stevioside, rebaudioside A, rebaudioside C, and dulcoside A, account for 9.1, 3.8, 0.6, and 0.30 percent of the total weight of the steviol glycosides found in wild type *Stevia* leaves, respectively, while the other steviol glucosides, such as Reb D and Reb M are present in significantly lower amounts. Extracts from the *Stevia rebaudiana* plant are commercially available and, in such extracts, stevioside and rebaudioside A are most often the primary components and can be used as the starting components or substrates for further enzymatic activity. Comparatively, the other known steviol glycosides are typically present in the stevia extract as minor or trace components. For example, the amount of rebaudioside A in typical commercial preparations can vary from about 20% to more than 90% of the total steviol glycoside content, with the amount of rebaudioside B at about 1-2%, the amount of rebaudioside C about 7-15%, and the amount of rebaudioside D can be about 2% of the total steviol glycosides.

Each of the different steviol glycosides can have different degrees of sweetness, 'mouth feel' and specific after-tastes associated with them. Relative to table sugar (i.e., "sucrose") the sweetness of steviol glycosides is generally significantly higher. For example, stevioside is 100-150 times sweeter than sucrose but has a bitter after-taste as noted in numerous taste tests, while rebaudiosides A and E are 250-450 times sweeter than sucrose and the after-taste profile is much better than stevioside. However, these steviol glycosides themselves still retain a noticeable aftertaste and lend themselves naturally to those applications in the food and beverage industries where this aftertaste or difference from sucrose can be masked or eliminated. In addition, the overall taste profile of plant-derived stevia extracts can be affected by the presence of the various steviol glycosides in the extract, which in turn may be affected by the environmental conditions experienced by the underlying plants and the extraction process used. These variations in plant production, weather conditions and extraction conditions can lead to inconsistent compositions of the steviol glycosides in the stevia extracts, such that taste profiles can vary strongly among different batches of extraction products. In such instances, these batches may not be useful for specific uses or formulations in the food and beverage industry. The taste profile of stevia extracts also can be affected by plant-derived or environment derived contaminants (such as pigments, lipids, proteins, phenolics and saccharides) that remain in the product after the extractions process. These contaminants typically have their own off-flavors, and can make the resultant extract undesirable for use in consumer products. In addition, the cost of isolating individual or specific combinations of steviol rebaudiosides that are not abundant or simply not present in stevia extracts may be cost and resource prohibitive.

Generally steviol glycosides are formed by a series of glycosylation reactions of steviol, which typically are catalyzed by UDP-glycosyltransferase (UGT) enzymes using uridine 5'-diphosphoglucose (UDP-glucose) as a donor of the sugar moiety. In plants, UGTs are a very divergent group of enzymes that can transfer a glucose residue from UDP-glucose to steviol. In these reactions, stevioside is often an intermediate in the biosynthesis of various rebaudioside compounds. For example, glycosylation of stevioside at the C-3' at the C-13-O-glucose of stevioside yields rebaudioside A; while glycosylation at the C-2' at the 19-O-glucose position of stevioside yields rebaudioside E.

It has previously been described that Reb D3 (13-[(2-O-β-D-glucopyranosyl-6-O-β-D-glucopyranosyl-β-Dglucopyranosyl)oxy] ent-kaur-16-en-19-oic acid-(2-O-β-D-glucopyranosyl-β-D glucopyranosyl)ester) can be converted from Reb E by EUGT11 or the EUS enzyme. Reb Z (Z1 and Z2) can be converted from Reb E by the HV1 enzyme. A mixture of two compounds named Reb Z was characterized as 13-[(2-O-β-D-glucopyranosyl-2-O-β-D-glucopyranosyl-β-D-glucopyranosyl)oxy] ent-kaur-16-en-19-oic acid-2-O-β-D-glucopyranosyl-β-D-glucopyranosyl ester (Reb Z1), or 13-[(2-O-β-D-glucopyranosyl-β-D-glucopyranosyl)oxy] ent-kaur-16-en-19-oic acid-R2-O-β-D-glucopyranosyl-2-O-β-D-glucopyranosyl-β-D-glucopyranosyl) ester (Reb Z2).

The steviol glycoside biosynthesis pathway involves conversion of ent-kaurenoic acid to steviol by the activity of enzyme KAH. It has been shown that UGT76G1 exhibits glucosylation activity towards steviol bioside forming rebaudioside B, and stevioside resulting in the production of rebaudioside A. In addition, the interaction affinity of KAH, UGT85C2, UGT74G1 and UGT76G1 has been evaluated for ent-kaurenoic acids and steviol. A model for KAH showed highest affinity for the ligand steviol, followed by steviol-monoside and ent-kaurenoic acid. The docking results for the three-dimensional model of UGT76G1 suggested its highest binding affinity for ent-kaurenoic acid but also suggested that these enzymes have the ability to interact with more than one of the ligands in the steviol glycoside biosynthesis pathway.

A practical approach to improve the taste quality of stevia extracts is to increase the yield of those rebaudioside compounds that have more desirable taste characteristics in general and to do this via a more productive synthetic pathway. Of those steviol glycosides tested many believe that Reb M has the most desirable taste and chemical characteristics for use in a variety of food and beverages. As stated above, however, the plant has vanishingly small amounts of this compound present in its leaves.

Going further, the extraction process from plants, typically employs solid-liquid extraction techniques using solvents like hexane, chloroform, and ethanol for steviol glycoside recovery (Catchpole et al., 2003). However, solvent extraction is itself energy intensive, leads to problems of toxic waste disposal, requires extensive acreage for the plants themselves to be grown and yields a product that requires further purification/modification or bioconversion The use of fermentation and/or enzymatic bio-conversion technology can allow for the production of steviol glycosides in microbial species that can increase the selectivity, abundance and purity of desired steviol glycosides.

In addition to the above, while consumers approve and actively seek natural and biological sources for food, feed, flavor or medicinal components they are also concerned about sourcing, consistent taste profile and environmentally sustainable production. Microbial fermentation and production methods can invention provide rebaudiosides in quantities useful for a variety of industries and research while doing so in a more natural fashion than inorganic synthesis or current plant extraction techniques.

Accordingly, a need exists for the development of novel steviol glycoside variants as well as related production methods that can be performed economically and conveniently to further enable human and animal consumption.

SUMMARY

The present disclosure relates, at least in part, to the identification, synthesis and production of several steviol glycosides from various rebaudiosides. In some aspects, the present disclosure provides the use of Reb D3 in the production of Reb R7-2 or Reb R6-2. In some aspects, the present disclosure provides the use of Reb D in the production of Reb R6-1. In some aspects, the present disclosure provides the use of Reb Z1 or Reb Z2 as the starting material for the production of Reb R6-4A. In some aspects, the present disclosure provides the use of Reb Z2 as the starting material for the production of R6-4B. The product steviol glycosides were identified by NMR analysis and after production were subjected to various taste tests and processing tests to identify their particular flavor and performance characteristics.

Some aspects of the present disclosure provide methods of producing rebaudioside R6-2A and/or R6-2B, the method comprising:

(I) preparing a reaction mixture comprising:

(i) rebaudioside D3;

(ii) one or more substrates selected from the group consisting of sucrose, uridine diphosphate (UDP), uridine diphosphate-glucose (UDP-glucose), and combinations thereof; and (iii) an enzyme selected from the group consisting of:

(a) a UDP-glycosyltransferase (UGT);

(b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain; and (II) incubating the reaction mixture for a sufficient time to produce rebaudioside R6-2A and/or R6-2B;

wherein the rebaudioside D3 has the structure of:

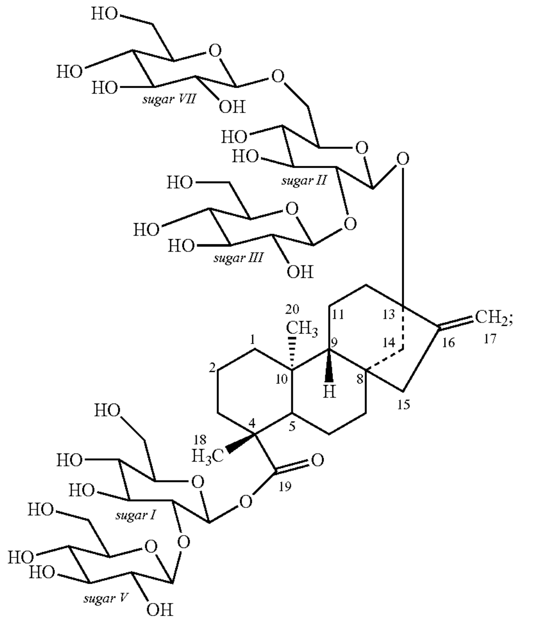

the rebaudioside R6-2A has the structure of:

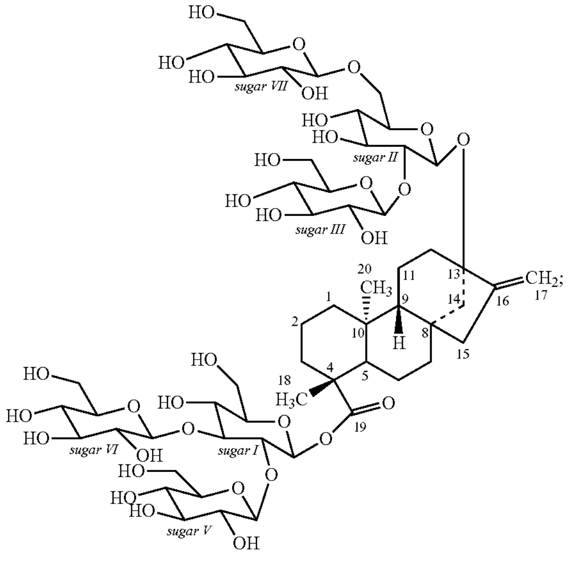

and the rebaudioside R6-2B has the structure of:

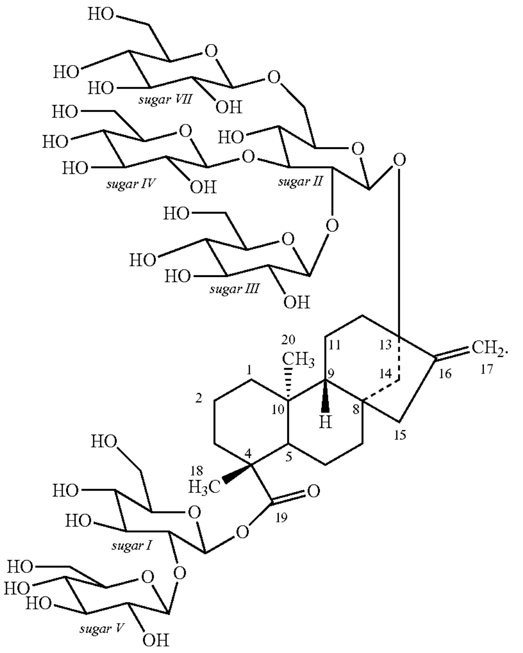

Other aspects of the present disclosure provide methods of producing rebaudioside R7-2, the method comprising:

(I) preparing a reaction mixture comprising:

(i) one or more of rebaudioside D3, rebaudioside R6-2A, and rebaudioside R6-2B;

(ii) one or more substrates selected from the group consisting of sucrose, uridine diphosphate (UDP), uridine diphosphate-glucose (UDP-glucose), and combinations thereof; and (iii) an enzyme selected from the group consisting of:

(a) a UDP-glycosyltransferase (UGT);

(b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain; and (II) incubating the reaction mixture for a sufficient time to produce rebaudioside R7-2; wherein the rebaudioside D3 has the structure of:

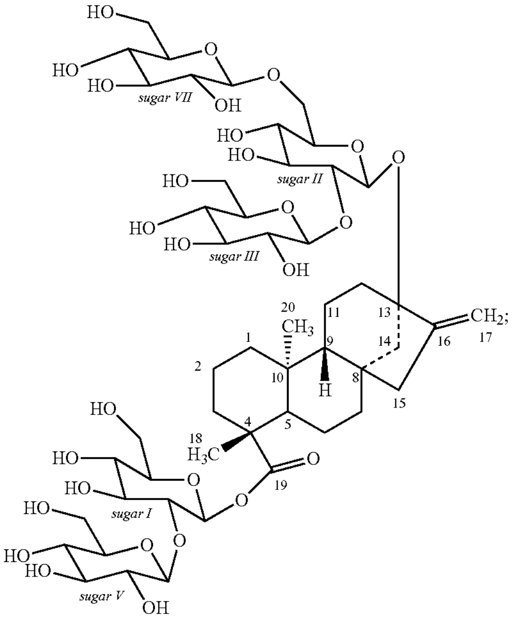

the rebaudioside R6-2A has the structure of:

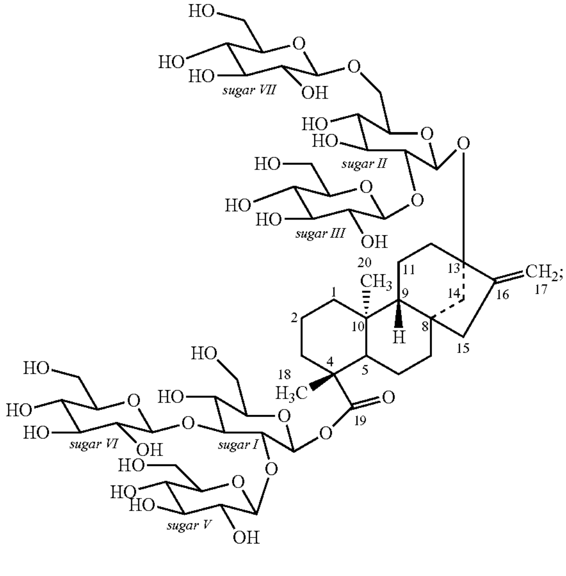

the rebaudioside R6-2B has the structure of:

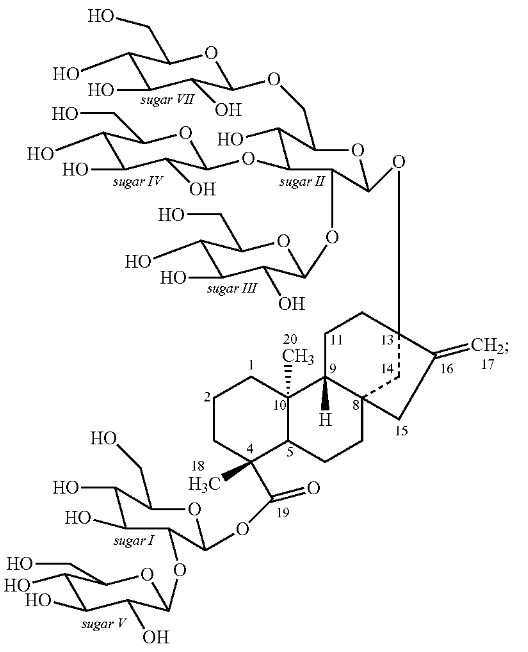

and the rebaudioside R7-2 has the structure of:

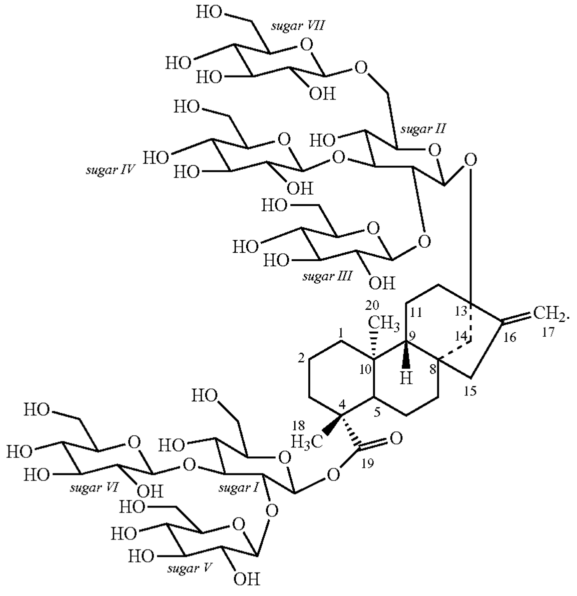

In some embodiments, the sucrose synthase or sucrose synthase domain is selected from the group consisting of an *Arabidopsis* sucrose synthase I, an *Arabidopsis* sucrose synthase 3 and a *Vigna radiate* sucrose synthase. In some embodiments, the sucrose synthase or sucrose synthase domain is an *Arabidopsis thaliana* sucrose synthase I. In some embodiments, the sucrose synthase or sucrose synthase domain is at least 80% identical to the amino acid sequence of SEQ ID NO: 9. In some embodiments, the sucrose synthase or sucrose synthase domain comprises the amino acid sequence of SEQ ID NO: 9.

In some embodiments, a glucose is covalently coupled to the rebaudioside D3 by the enzyme to produce rebaudioside R6-2A and/or R6-2B. In some embodiments, the glucose is covalently coupled to sugar I of rebaudioside D3 by the enzyme to produce rebaudioside R6-2A. In some embodiments, the glucose is covalently coupled to sugar II of rebaudioside D3 by the enzyme to produce rebaudioside R6-2B. In some embodiments, two glucose are covalently coupled to the rebaudioside D3 by the enzyme to produce rebaudioside R7-2. In some embodiments, the two glucose are covalently coupled to sugar I and sugar II of rebaudioside D3 by the enzyme to produce rebaudioside R7-2.

the UDP-glycosyltransferase is at least 80% identical to the amino acid sequence of SEQ ID NO: 1. In some embodiments, the UDP-glycosyltransferase comprises the amino acid sequence of SEQ ID NO: 1. In some embodiments, the UDP-glycosyltransferase fusion enzyme is at least 80% identical to the amino acid sequence of SEQ ID NO: 5. In some embodiments, the UDP-glycosyltransferase fusion enzyme comprises the amino acid sequence of SEQ ID NO: 5.

In some embodiments, the methods further comprise producing rebaudioside D3 by incubating rebaudioside E with a UDP-glycosyltransferase and a substrate selected from the group consisting of sucrose, UDP, UDP-glucose, and combinations thereof.

Further provided herein are methods of producing rebaudioside R6-4A and/or rebaudioside R6-4B, the method comprising:

(I) preparing a reaction mixture comprising:

(i) at least one of rebaudioside Z1 and rebaudioside Z2;

(ii) one or more substrates selected from the group consisting of sucrose, uridine diphosphate (UDP), uridine diphosphate-glucose (UDP-glucose), and combinations thereof; and (iii) an enzyme selected from the group consisting of:

(a) a UDP-glycosyltransferase (UGT);

(b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain; and (II) incubating the reaction mixture for a sufficient time to produce rebaudioside R6-4A and/or rebaudioside R6-4B; wherein the rebaudioside Z1 has the structure of:

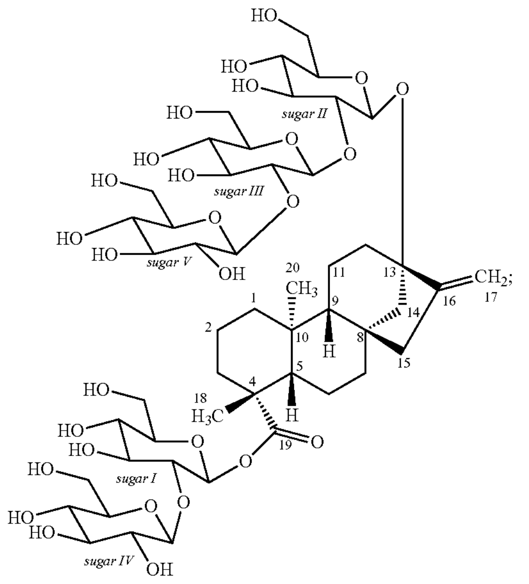

the rebaudioside Z2 has the structure of:

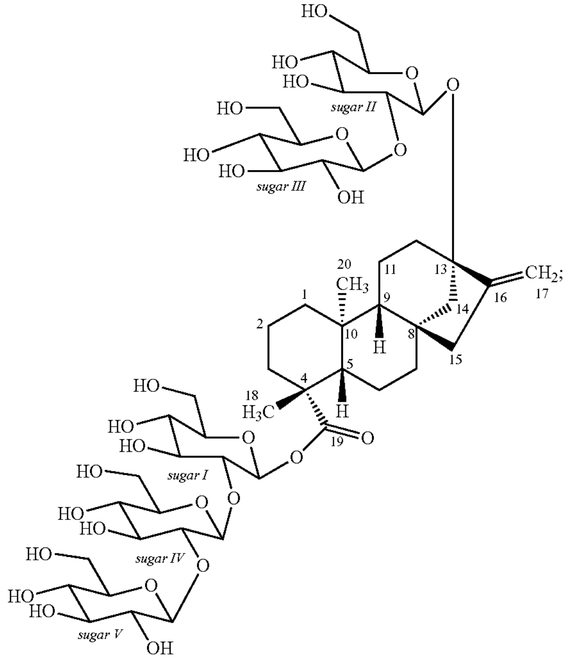

the rebaudioside R6-4A has the structure of:

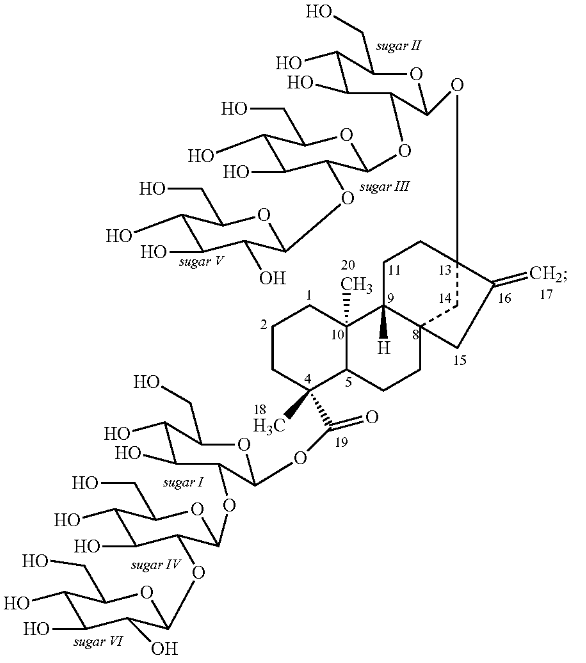

and the rebaudioside R6-4B has the structure of:

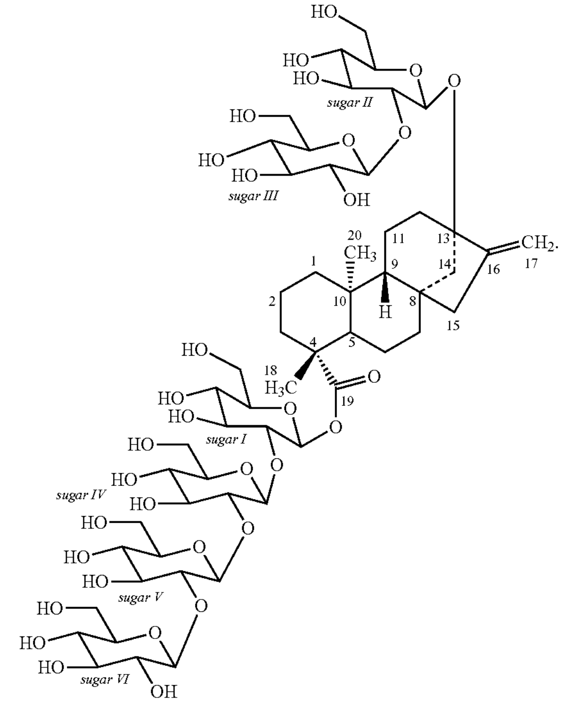

In some embodiments of any one of the methods or compositions provided herein, the sucrose synthase or sucrose synthase domain is selected from the group consisting of an *Arabidopsis* sucrose synthase I, an *Arabidopsis* sucrose synthase 3 and a *Vigna radiate* sucrose synthase. In some embodiments of any one of the methods or compositions provided herein, the sucrose synthase or sucrose synthase domain is an *Arabidopsis thaliana* sucrose synthase I. In some embodiments of any one of the methods or compositions provided herein, the sucrose synthase or sucrose synthase domain is at least 80% identical to the amino acid sequence of SEQ ID NO: 9. In some embodiments of any one of the methods or compositions provided herein, the sucrose synthase or sucrose synthase domain comprises the amino acid sequence of SEQ ID NO: 9.

In some embodiments of any one of the methods or compositions provided herein, a glucose is covalently coupled to the rebaudioside Z1 or rebaudioside Z2 by the enzyme to produce rebaudioside R6-4A. In some embodiments of any one of the methods or compositions provided herein, the glucose is covalently coupled to sugar IV of rebaudioside Z1 by the enzyme to produce rebaudioside R6-4A. In some embodiments of any one of the methods or compositions provided herein, the glucose is covalently coupled to sugar III of rebaudioside Z2 by the enzyme to produce rebaudioside R6-4A. In some embodiments of any one of the methods or compositions provided herein, the glucose is covalently coupled to the rebaudioside Z2 by the enzyme to produce rebaudioside R6-4B. In some embodiments of any one of the methods or compositions provided herein, the glucose is covalently coupled to sugar V of rebaudioside Z2 by the enzyme to produce rebaudioside R6-4B.

In some embodiments of any one of the methods or compositions provided herein, the UDP-glycosyltransferase is at least 80% identical to the amino acid sequence of SEQ ID NO: 3. In some embodiments of any one of the methods or compositions provided herein, the UDP-glycosyltransferase comprises the amino acid sequence of SEQ ID NO: 3. In some embodiments of any one of the methods or compositions provided herein, the UDP-glycosyltransferase fusion enzyme is at least 80% identical to the amino acid sequence of SEQ ID NO: 7. In some embodiments of any one of the methods or compositions provided herein, the UDP-glycosyltransferase fusion enzyme comprises the amino acid sequence of SEQ ID NO: 7.

In some embodiments of any one of the methods or compositions provided herein, the method further comprises producing rebaudioside Z1 or rebaudioside Z2 by incubating rebaudioside E with a UDP-glycosyltransferase and a substrate selected from the group consisting of sucrose, UDP, UDP-glucose, and combinations thereof.

Other aspects of the present disclosure provide methods of producing rebaudioside R6-1, the method comprising:

(I) preparing a reaction mixture comprising:

(i) rebaudioside D;

(ii) one or more substrates selected from the group consisting of sucrose, uridine diphosphate (UDP), uridine diphosphate-glucose (UDP-glucose), and combinations thereof; and (iii) an enzyme selected from the group consisting of:

(a) a UDP-glycosyltransferase (UGT);

(b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain; and (II) incubating the reaction mixture for a sufficient time to produce rebaudioside R6-1; wherein the rebaudioside D has the structure of:

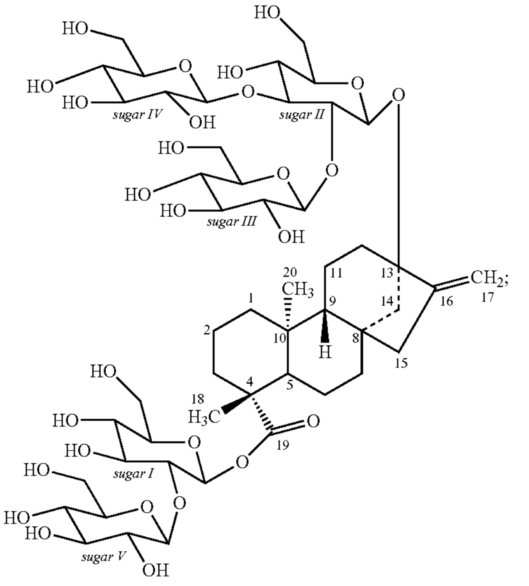

and the rebaudioside R6-1 has the structure of:

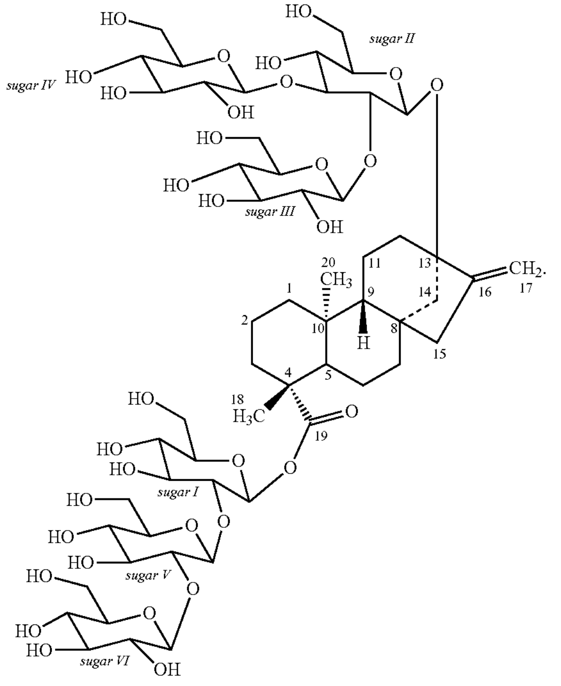

In some embodiments of any one of the methods or compositions provided herein, the sucrose synthase or sucrose synthase domain is selected from the group consisting of an *Arabidopsis* sucrose synthase I, an *Arabidopsis* sucrose synthase 3 and a *Vigna radiate* sucrose synthase. In some embodiments, the sucrose synthase or sucrose synthase domain is an *Arabidopsis thaliana* sucrose synthase I. In some embodiments of any one of the methods or compositions provided herein, the sucrose synthase or sucrose synthase domain is at least 80% identical to the amino acid sequence of SEQ ID NO: 9. In some embodiments, the sucrose synthase or sucrose synthase domain comprises the amino acid sequence of SEQ ID NO: 9. In some embodiments of any one of the methods or compositions provided herein, a glucose is covalently coupled to the rebaudioside D by the enzyme to produce rebaudioside R6-1. In some embodiments of any one of the methods or compositions provided herein, the glucose is covalently coupled to sugar V of rebaudioside D by the enzyme to produce rebaudioside R6-1. In some embodiments of any one of the methods or compositions provided herein, the UDP-glycosyltransferase is at least 80% identical to the amino acid sequence of SEQ ID NO: 3. In some embodiments of any one of the methods or compositions provided herein, the UDP-glycosyltransferase comprises the amino acid sequence of SEQ ID NO: 3. In some embodiments of any one of the methods or compositions provided herein, the UDP-glycosyltransferase fusion enzyme is at least 80% identical to the amino acid sequence of SEQ ID NO: 7. In some embodiments of any one of the methods or compositions provided herein, the UDP-glycosyltransferase fusion enzyme comprises the amino acid sequence of SEQ ID NO: 7.

In some embodiments of any one of the methods or compositions provided herein, the method further comprises producing rebaudioside D by incubating rebaudioside E with a UDP-glycosyltransferase and a substrate selected from the group consisting of sucrose, UDP, UDP-glucose, and combinations thereof. In some embodiments of any one of the methods or compositions provided herein, the method further comprises producing rebaudioside D by incubating rebaudioside A with a UDP-glycosyltransferase and a substrate selected from the group consisting of sucrose, UDP, UDP-glucose, and combinations thereof.

In some embodiments of any one of the methods or compositions provided herein, the reaction mixture is in vitro. In some embodiments of any one of the methods or compositions provided herein, the reaction mixture is a cell-based reaction mixture. In some embodiments of any one of the methods or compositions provided herein, the cell is selected from the group consisting of a yeast, a non-steviol glycoside producing plant, an alga, a fungus, and a bacterium.

Other aspects of the present disclosure provide rebaudiosides (e.g., synthetic rebaudiosides) selected from:

(i) rebaudioside R6-2A having the structure:

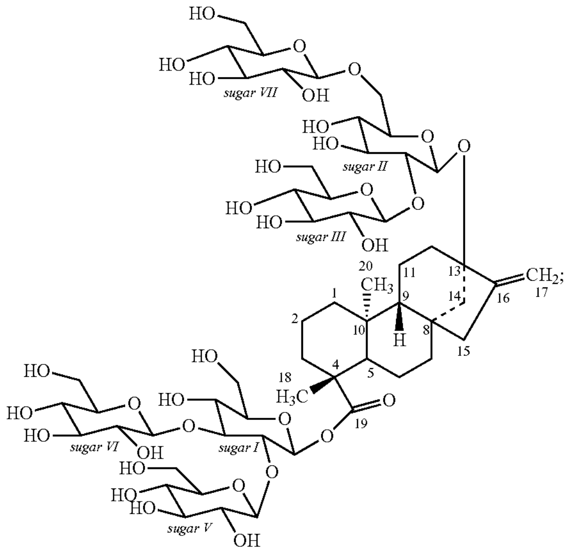

(ii) rebaudioside R6-2B having the structure:

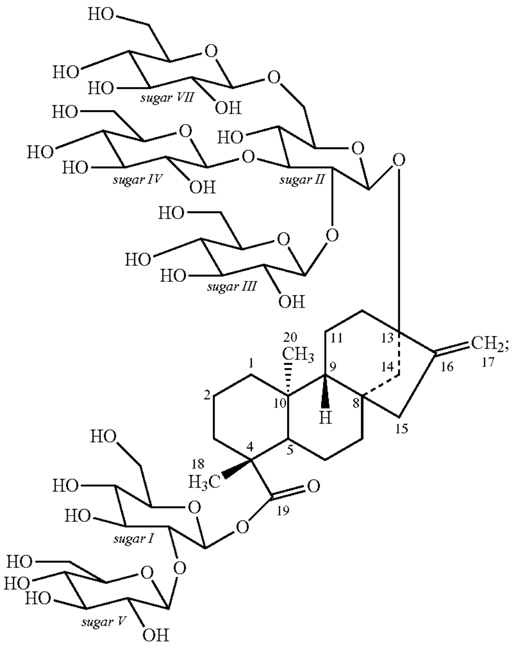

(iii) rebaudioside R7-2 having the structure:

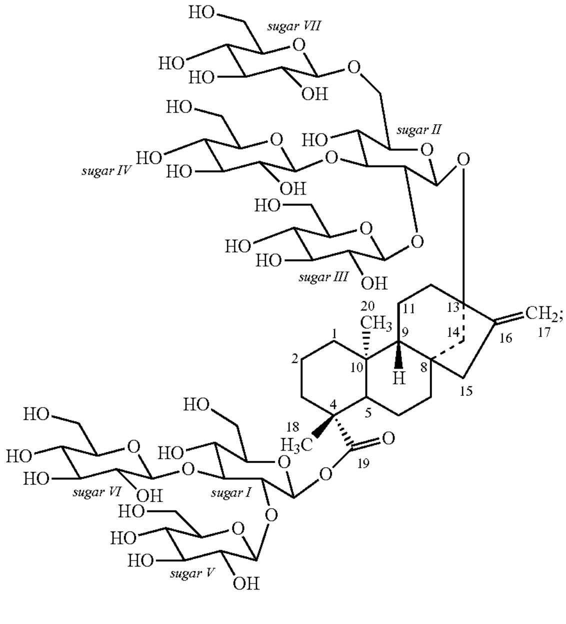

(iv) rebaudioside R6-4A having the structure:

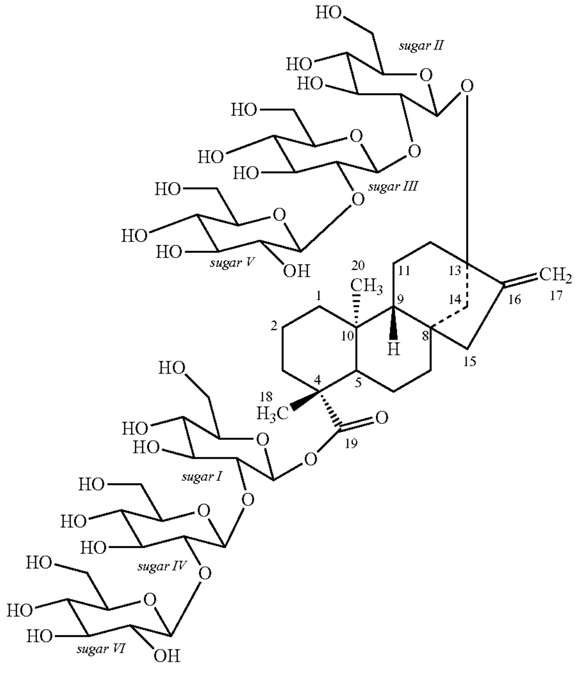

(v) rebaudioside R6-4B having the structure:

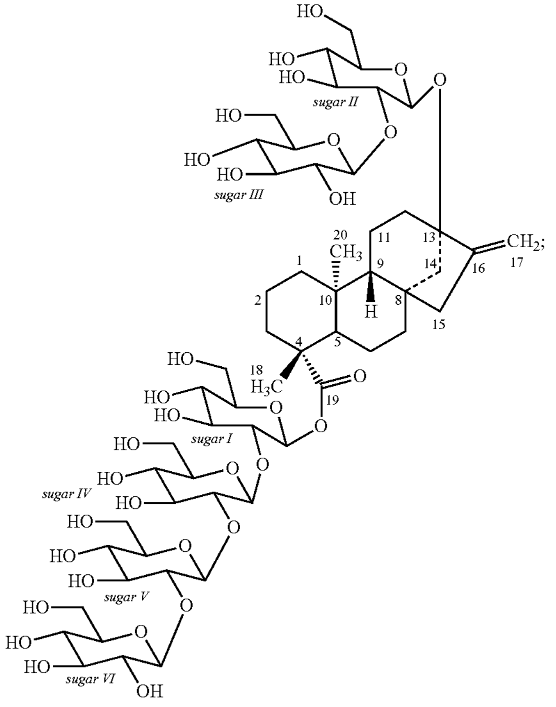

and (vi) rebaudioside R6-1 having the structure:

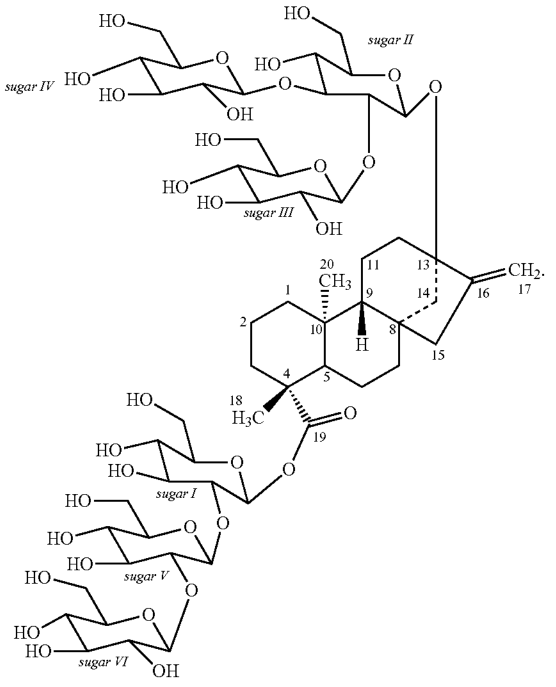

Composition comprising any one of the rebaudiosides (e.g., synthetic rebaudiosides) provided herein are also provided.

Further provided herein are the use of any one of the rebaudiosides (e.g., synthetic rebaudiosides) described herein as a sweetener.

Other aspects of the present disclosure provide an orally consumable product comprising a sweetening amount of any one of the sweeteners provided herein, such as selected from the group consisting of rebaudioside R6-2A, R6-2B, R7-2, R6-4A, R6-4B, and/or R6-1, such as wherein the orally consumable product is selected from the group consisting of a beverage product and a consumable product.

In some embodiments of any one of the methods or compositions provided herein, the sweetener is the only sweetener. In some embodiments of any one of the methods or compositions provided herein, the orally consumable product comprises from about 5 ppm to 100 ppm of the rebaudioside. In some embodiments of any one of the methods or compositions provided herein, the orally consumable product has a sweetness intensity equivalent to about 1% (w/v-%) to about 4% (w/v-%) sucrose solution.

In some embodiments of any one of the methods or compositions provided herein, the orally comsumable product further comprises at least one additional sweetener. In some embodiments of any one of the methods or compositions provided herein, the at least one additional sweetener is selected from the group consisting of a stevia extract, a steviol glycoside, stevioside, rebaudioside A, rebaudioside B, rebaudioside C, rebaudioside D, rebaudioside E derived from recombinant microbial biosynthesis, rebaudioside F, dulcoside A, rebaudioside M, rebaudioside V, rebaudioside W, rebaudioside D3, rebaudioside Z1, rebaudioside Z2, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof.

In some embodiments of any one of the methods or compositions provided herein, the orally comsumable product further comprises at least one additive, such as selected from the group consisting of a carbohydrate, a polyol, an amino acid or salt thereof, a polyamino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof.

In some embodiments of any one of the methods or compositions provided herein, the consumable product is selected from the group consisting of a food product, a nutraceutical, a pharmaceutical, a dietary supplement, a dental hygienic composition, an edible gel composition, a cosmetic product and a tabletop flavoring. In some embodiments of any one of the methods or compositions provided herein, the beverage product is selected from the group consisting of a carbonated beverage product and a non-carbonated beverage product. In some embodiments of any one of the methods or compositions provided herein, the beverage product is selected from the group consisting of a soft drink, a fountain beverage, a frozen beverage; a ready-to-drink beverage; a frozen and ready-to-drink beverage, coffee, tea, a dairy beverage, a powdered soft drink, a liquid concentrate, flavored water, enhanced water, fruit juice, a fruit juice flavored drink, a sport drink, and an energy drink.

Any one of the rebaudiosides or compositions provided herein, can be used in an analgesics, pest repellents, food or dietary supplement. Any one of such compositions are also provided herein. Any one of the compositions provided herein can be in an aerosol, liquid, gel or granular form.

In any one of the methods or compositions provided herein, the cellular system is selected from the group consisting of bacteria, yeast, and a combination thereof, or any cellular system that would allow the genetic transformation with selected genes and thereafter the biosynthetic production of the desired steviol glycoside. In any one of the methods or compositions provided herein, the cellular system is a microbial system, such as *E. coli.*

In one aspect, a rebaudioside or composition thereof, produced by any one of the methods provided herein, is provided.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiments disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DEFINITIONS

Figure 1:
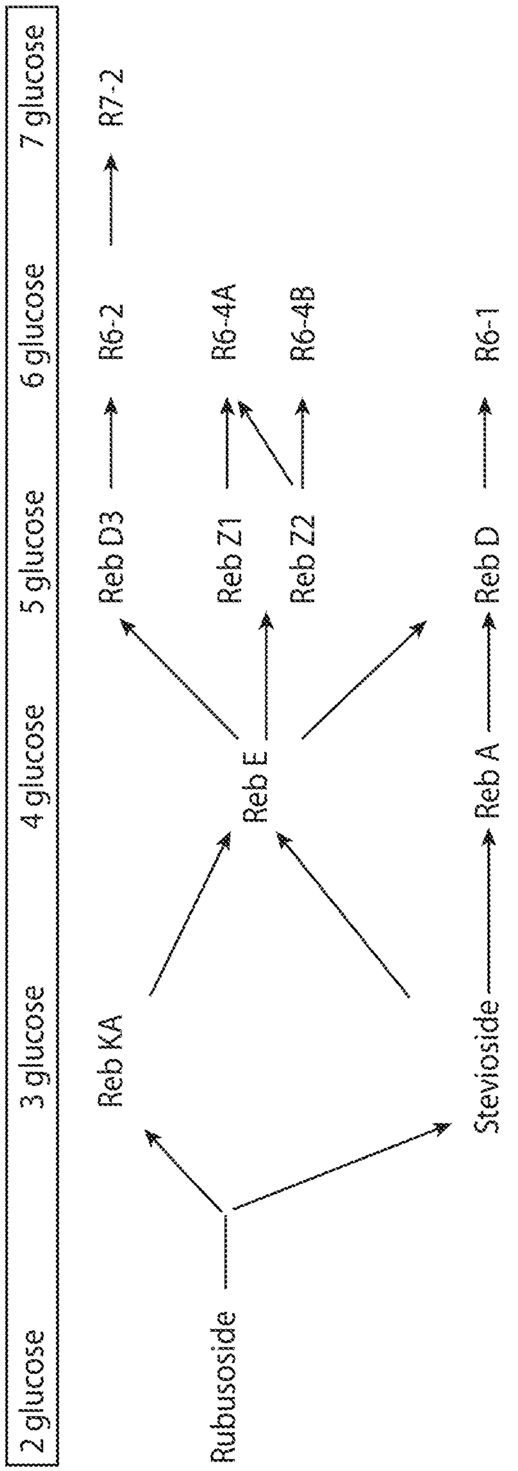
FIG. 1. Biosynthetic pathway of R6-1, R7-2, R6-4A and R6-4B.

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

The term "complementary" is used according to its ordinary and customary meaning as understood by a person of ordinary skill in the art, and is used without limitation to describe the relationship between nucleotide bases that are capable to hybridizing to one another. For example, with respect to DNA, adenosine is complementary to thymine and cytosine is complementary to guanine. Accordingly, the subject technology also includes isolated nucleic acid fragments that are complementary to the complete sequences as reported in the accompanying Sequence Listing as well as those substantially similar nucleic acid sequences.

The terms "nucleic acid" and "nucleotide" are used according to their respective ordinary and customary meanings as understood by a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is used according to its ordinary and customary meaning as understood by a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein refers to a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are used according to their respective ordinary and customary meanings as understood by a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are used according to their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full length polypeptide or protein, and has substantially the same biological activity, or carries out substantially the same function as the full length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from superfamilies and homologous polynucleotides or proteins from different species (Reeck et al., Cell 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical.

"Percent (%) amino acid sequence identity" with respect to the variant polypeptide sequences of the subject technology refers to the percentage of amino acid residues in a candidate sequence that are identical with the amino acid residues of a reference polypeptide after aligning the sequences and introducing gaps, if necessary, to achieve the maximum percent sequence identity.

Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, the % amino acid sequence identity may be determined using the sequence comparison program NCBI-BLAST2. The NCBI-BLAST2 sequence comparison program may be downloaded from ncbi.nlm.nih.gov. NCBI BLAST2 uses several search parameters, wherein all of those search parameters are set to default values including, for example, unmask yes, strand=all, expected occurrences 10, minimum low complexity length=15/5, multi-pass e-value=0.01, constant for multi-pass=25, dropoff for final gapped alignment=25 and scoring matrix=BLOSUM62. In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In this sense, techniques for determining amino acid sequence "similarity" are well known in the art. In general, "similarity" refers to the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known by those skilled in the art.

An amino acid position "corresponding to" a reference position refers to a position that aligns with a reference sequence, as identified by aligning the amino acid sequences. Such alignments can be done by hand or by using well-known sequence alignment programs such as ClustalW2, Blast 2, etc.

Unless specified otherwise, the percent identity of two polypeptide or polynucleotide sequences refers to the percentage of identical amino acid residues or nucleotides across the entire length of the shorter of the two sequences.

"Coding sequence" is used according to its ordinary and customary meaning as understood by a person of ordinary skill in the art, and is used without limitation to refer to a DNA sequence that encodes for a specific amino acid sequence.

"Suitable regulatory sequences" is used according to its ordinary and customary meaning as understood by a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is used according to its ordinary and customary meaning as understood by a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is used according to its ordinary and customary meaning as understood by a person of ordinary skill in the art, and is used without limitation to refer to the transcription and stable accumulation of sense (mRNA) or antisense RNA derived from the nucleic acid fragment of the subject technology. "Overexpression" refers to the production of a gene product in transgenic or recombinant organisms that exceeds levels of production in normal or non-transformed organisms.

"Transformation" is used according to its ordinary and customary meaning as understood by a person of ordinary skill in the art, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "transformed," "transgenic," and "recombinant," when used herein in connection with host cells, are used according to their ordinary and customary meanings as understood by a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are used according to their ordinary and customary meanings as understood by a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are used according to their ordinary and customary meanings as understood by a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used herein are well known in the art and are described, for example, by Sambrook, J., Fritsch, E. F. and Maniatis, T. Molecular Cloning: A Laboratory Manual, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. Experiments with Gene Fusions; Cold Spring Harbor Laboratory: Cold Spring Harbor, N.Y., 1984; and by Ausubel, F. M. et al., In Current Protocols in Molecular Biology, published by Greene Publishing and Wiley-Interscience, 1987; the entireties of each of which are hereby incorporated herein by reference to the extent they are consistent herewith.

As used herein, "synthetic" or "organically synthesized" or "chemically synthesized" or "organically synthesizing" or "chemically synthesizing" or "organic synthesis" or "chemical synthesis" are used to refer to preparing the compounds through a series of chemical reactions; this does not include extracting the compound, for example, from a natural source.

The term "orally consumable product" as used herein refers to any beverage, food product, dietary supplement, nutraceutical, pharmaceutical composition, dental hygienic composition and cosmetic product which are contacted with the mouth of man or animal, including substances that are taken into and subsequently ejected from the mouth and substances which are drunk, eaten, swallowed, or otherwise ingested; and that are safe for human or animal consumption when used in a generally acceptable range of concentrations.

The term "food product" as used herein refers to fruits, vegetables, juices, meat products such as ham, bacon and sausage; egg products, fruit concentrates, gelatins and gelatin-like products such as jams, jellies, preserves, and the like; milk products such as ice cream, sour cream, yogurt, and sherbet; icings, syrups including molasses; corn, wheat, rye, soybean, oat, rice and barley products, cereal products, nut meats and nut products, cakes, cookies, confectionaries such as candies, gums, fruit flavored drops, and chocolates, chewing gum, mints, creams, icing, ice cream, pies and breads. "Food product" also refers to condiments such as herbs, spices and seasonings, flavor enhancers, such as monosodium glutamate. "Food product" further refers to also includes prepared packaged products, such as dietetic sweeteners, liquid sweeteners, tabletop flavorings, granulated flavor mixes which upon reconstitution with water provide non-carbonated drinks, instant pudding mixes, instant coffee and tea, coffee whiteners, malted milk mixes, pet foods, livestock feed, tobacco, and materials for baking applications, such as powdered baking mixes for the preparation of breads, cookies, cakes, pancakes, donuts and the like. "Food product" also refers to diet or low-calorie food and beverages containing little or no sucrose.

As used herein, the term "stereoisomer" is a general term for all isomers of individual molecules that differ only in the orientation of their atoms in space. "Stereoisomer" includes enantiomers and isomers of compounds with more than one chiral center that are not mirror images of one another (diastereomers).

As used herein, the term "sweetness intensity" refers to the relative strength of sweet sensation as observed or experienced by an individual, e.g., a human, or a degree or amount of sweetness detected by a taster, for example on a Brix scale.

As used herein, the term "enhancing the sweetness" refers to the effect of rebaudiosides in increasing, augmenting, intensifying, accentuating, magnifying, and/or potentiating the sensory perception of one or more sweetness characteristics of a beverage product or a consumable product of the present disclosure without changing the nature or quality thereof, as compared to a corresponding orally consumable product that does not contain a rebaudioside of the present disclosure.

As used herein, the term "off-taste(s)" refers to an amount or degree of taste that is not characteristically or usually found in a beverage product or a consumable product of the present disclosure. For example, an off-taste is an undesirable taste of a sweetened consumable to consumers, such as, a bitter taste, a licorice-like taste, a metallic taste, an aversive taste, an astringent taste, a delayed sweetness onset, a lingering sweet aftertaste, and the like, etc.

As used herein, the term "w/v-%" refers to the weight of a compound, such as a sugar, (in grams) for every 100 ml of a liquid orally consumable product of the present disclosure containing such compound. As used herein, the term "w/w-%" refers to the weight of a compound, such as a sugar, (in grams) for every gram of an orally consumable product of the present disclosure containing such compound.

As used herein, the term "ppm" refers to part(s) per million by weight, for example, the weight of a compound, such as a rebaudioside of the present disclosure (in milligrams) per kilogram of an orally consumable product of the present disclosure containing such compound (i.e., mg/kg) or the weight of a compound, such as a rebaudioside of the present disclosure (in milligrams) per liter of an orally consumable product of the present disclosure containing such compound (i.e., mg/L); or by volume, for example the volume of a compound, such as a rebaudioside of the present disclosure (in milliliters) per liter of an orally consumable product of the present disclosure containing such compound (i.e., ml/L).

Steviol Glycosides are a class of chemical compounds responsible for the sweet taste of the leaves of the South American plant *Stevia rebaudiana* (Asteraceae), and can be used as sweeteners in food, feed and beverages alone, in combination with one another or in combination with other sweeteners and taste modifiers.

Cellular system is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.

Growing the Cellular System. Growing includes providing an appropriate medium that would allow cells to multiply and divide. It also includes providing resources so that cells or cellular components can translate and make recombinant proteins.

Protein Expression. Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration". Any embodiment described herein as "exemplary" is not necessarily to be construed as preferred or advantageous over other embodiments.

DETAILED DESCRIPTION

The present invention relates, at least in part, to novel steviol glycosides, R7-2, R6-2A, R6-2B, R6-1, R6-4A and R6-4B and methods of producing these novel steviol glycosides, such as through enzymatic conversion. The chemical structures can be confirmed by LC MS and NMR analysis. R6-1, R6-2A, R6-62B, R6-4A and R6-4B contain 6 glucosyl groups and R7-2 contains 7 glucosyl groups.

Precursor Synthesis

As previously stated steviol glycosides are the chemical compounds responsible for the sweet taste of the leaves of the South American plant *Stevia rebaudiana* (Asteraceae) and in the plant *Rubus chingii* (Rosaceae). These compounds are glycosylated diterpenes. Specifically, their molecules can be viewed as a steviol molecule, with its hydroxyl hydrogen atom replaced by a glucose molecule to form an ester, and a hydroxyl hydrogen with combinations of glucose and rhamnose to form an acetal.

One method of making the compounds of interest in the current invention is to take common or inexpensive precursors, such as steviol, stevioside, Reb E, Reb D or rubusoside, such as derived chemically or produced via biosynthesis in engineered microbes, such as bacteria and/or yeast, and to synthesize target steviol glycosides, such as through known or inexpensive methods, such as Reb D3 and Z.

Aspects of the present invention relate to methods involving recombinantly expressing enzymes in a microbial system capable of producing steviol. In general, such enzymes may include: a copalyl diphosphate synthase (CPS), a kaurene synthase (KS) and a geranylgeranyl diphosphate to synthase (GGPPS) enzyme. Preferably, in some embodiments, this occurs in a microbial strain that expresses an endogenous isoprenoid synthesis pathway, such as the non-mevalonate (MEP) pathway or the mevalonic acid pathway (MVA). In some embodiments of any one of the methods or compositions provided herein, the cell is a bacterial cell, such as *E. coli*, or a yeast cell, such as a *Saccharomyces* cell, *Pichia* cell, or a *Yarrowia* cell. In some embodiments of any one of the methods or compositions provided herein. the cell is an algal cell or a plant cell.

Thereafter, the precursor can be recovered from the fermentation culture and used in chemical synthesis. Typically, this is steviol though it can be kaurene, or a steviol glycoside from the cell culture. In some embodiments of any one of the methods or compositions provided herein, the steviol, kaurene and/or steviol glycosides is recovered from the gas phase while in other embodiments, an organic layer or polymeric resin is added to the cell culture, and the kaurene, steviol and/or steviol glycosides is recovered from the organic layer or polymeric resin. In some embodiments of any one of the methods or compositions provided herein, the steviol glycoside is selected from rebaudioside A, rebaudioside B, rebaudioside C, rebaudioside E, rebaudioside F, or dulcoside A. In some embodiments of any one of the methods or compositions provided herein, the terpenoid produced is steviobioside or stevioside. It should also be appreciated that in some embodiments, at least one enzymatic step, such as one or more glycosylation steps, are performed ex vivo.

As described herein, the enzymes used in the methods described herein have UDP-glycosyltransferase activities and are useful for developing biosynthetic methods for preparing steviol glycosides that are either not present in nature or typically of low abundance in natural sources, such as rebaudioside R6-1, R2-2A, R6-2B, R6-4A, R6-4B and R7-2, respectively.

The substrate can be any natural or synthetic compound capable of being converted into a steviol glycoside compound in a reaction catalyzed by one or more UDP-glucosyltransferases. For example, the substrate can be natural stevia extract, steviol, steviol-13-O-glucoside, steviol-19-O-glucoside, 2-bioside, rubusoside, stevioside, rebaudioside A, rebaudioside D, rebaudioside D3, rebaudioside Z1, rebaudioside Z2, or rebaudioside E. The substrate can be a pure compound or a mixture of different compounds.

Also described herein is a coupling reaction system in which the enzymes (e.g., UDP transferases) described herein can function in combination with one or more additional enzymes (e.g., sucrose synthase) to improve the efficiency or modify the outcome of the overall biosynthesis of steviol glycoside compounds. For example, the additional enzyme may regenerate the UDP-glucose needed for the glycosylation reaction by converting the UDP produced from the glycosylation reaction back to UDP-glucose (using, for example, sucrose as a donor of the glucose residue), thus improving the efficiency of the glycosylation reaction.

Sucrose synthase catalyzes the chemical reaction between UDP-glucose and D-fructose to produce UDP and sucrose. Sucrose synthase is a glycosyltransferase. The systematic name of this enzyme class is UDP-glucose:D-fructose 2-alpha-D-glucosyltransferase. Other names in common use include UDP glucose-fructose glucosyltransferase, sucrose synthetase, sucrose-UDP glucosyltransferase, sucrose-uridine diphosphate glucosyltransferase, and uridine diphosphoglucose-fructose glucosyltransferase. Addition of the sucrose synthase to the reaction mixture that includes a uridine diphospho glycosyltransferase creates a "UGT-SUS coupling system". In the UGT-SUS coupling system, UDP-glucose can be regenerated from UDP and sucrose, which allows for omitting the addition of extra UDP-glucose to the reaction mixture or using UDP in the reaction mixture.

Suitable sucrose synthase for use in the methods described herein include *Arabidopsis* sucrose synthase I, an *Arabidopsis* sucrose synthase 3 and a *Vigna radiate* sucrose synthase. In some embodiments of any one of the methods or compositions provided herein, the sucrose synthase or sucrose synthase domain is an *Arabidopsis thaliana* sucrose synthase I.

Suitable UDP-glycosyltransferase includes any UGT known in the art as capable of catalyzing one or more reactions in the biosynthesis of steviol glycoside compounds, such as UGT85C2, UGT74G1, HV1, UGT76G1, or the functional homologs thereof. In some embodiments, the UDP-glycotransferase used in any one of the methods described herein is UGT76G1. In some embodiments, the UDP-glycotransferase used in any one of the methods described herein is a UGT76G1-sucrose synthase fusion enzyme. In some embodiments, the UDP-glycotransferase used in any one of the methods described herein is HV1 UTG. In some embodiments, the UDP-glycotransferase used in any one of the methods described herein is a HV1 UGT-sucrose synthase fusion enzyme.

Standard recombinant DNA and molecular cloning techniques used here are well known in the art and are described, for example, by Sambrook, J., Fritsch, E. F. and Maniatis, T. Molecular Cloning: A Laboratory Manual, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. Experiments with Gene Fusions; Cold Spring Harbor Laboratory: Cold Spring Harbor, N.Y., 1984; and by Ausubel, F. M. et al., In Current Protocols in Molecular Biology, published by Greene Publishing and Wiley-Interscience, 1987; (the entirety of each of which is hereby incorporated herein by reference).

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described herein.

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

Glycosylation is often considered a ubiquitous reaction controlling the bioactivity and storage of plant natural products. Glycosylation of small molecules is catalyzed by a superfamily of transferases in most plant species that have been studied to date. These glycosyltransferases (GTs) have been classified into over 60 families. Of these, the family 1 GT enzymes, also known as the UDP glycosyltransferases (UGTs) and UDP-rhamnosyltransferase, transfer sugar moieties to specific acceptor molecules. These are the molecules that transfer such sugar moieties in the steviol glycosides to help create various rebaudiosides. Each of these enzymes have their own activity profile and preferred structure locations where they transfer their activated sugar moieties.

Synthetic Rebaudioside R6-2A and R6-2B and Methods of Producing

Some aspects of the present disclosure provide a sweetener (e.g., non-caloric and/or synthetic) that has been given the name "Rebaudioside R6-2A (Reb R6-2A)." Rebaudioside R6-2A has the molecular formula of $C_{56}H_{90}O_{33}$ and has the structure of:

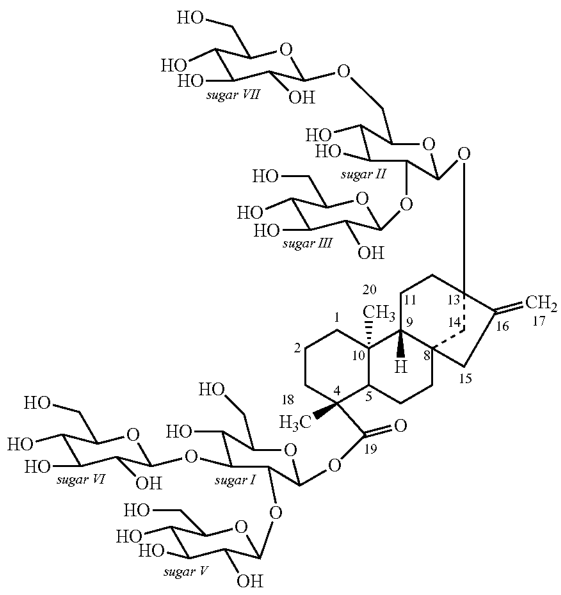

Some aspects of the present disclosure provide a sweetener (e.g., non-caloric and/or synthetic) that has been given the name "Rebaudioside R6-2B (Reb R6-2B)." Rebaudioside R6-2B has the molecular formula of $C_{56}H_{90}O_{33}$ and has the structure of:

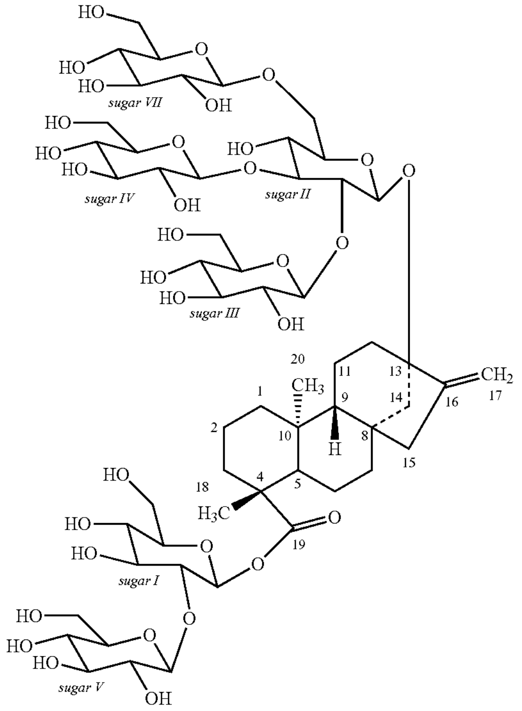

Some aspects of the present disclosure provide methods of producing rebaudioside R6-2A and/or rebaudioside R6-2B. In some embodiments of any one of the methods or compositions provided herein, the rebaudioside R6-2A and/or rebaudioside R6-2B is produced from rebaudioside D3. For example, in some embodiments, the method comprises (I) preparing a reaction mixture comprising: (i) rebaudioside D3; (ii) one or more substrates selected from the group consisting of sucrose, uridine diphosphate (UDP), uridine diphosphate-glucose (UDP-glucose), and combinations thereof; and (iii) an enzyme selected from the group consisting of: (a) a UDP-glycosyltransferase (UGT); (b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain; and (II) incubating the reaction mixture for a sufficient time to produce rebaudioside R6-2A and/or R6-2B.

Figure 2:
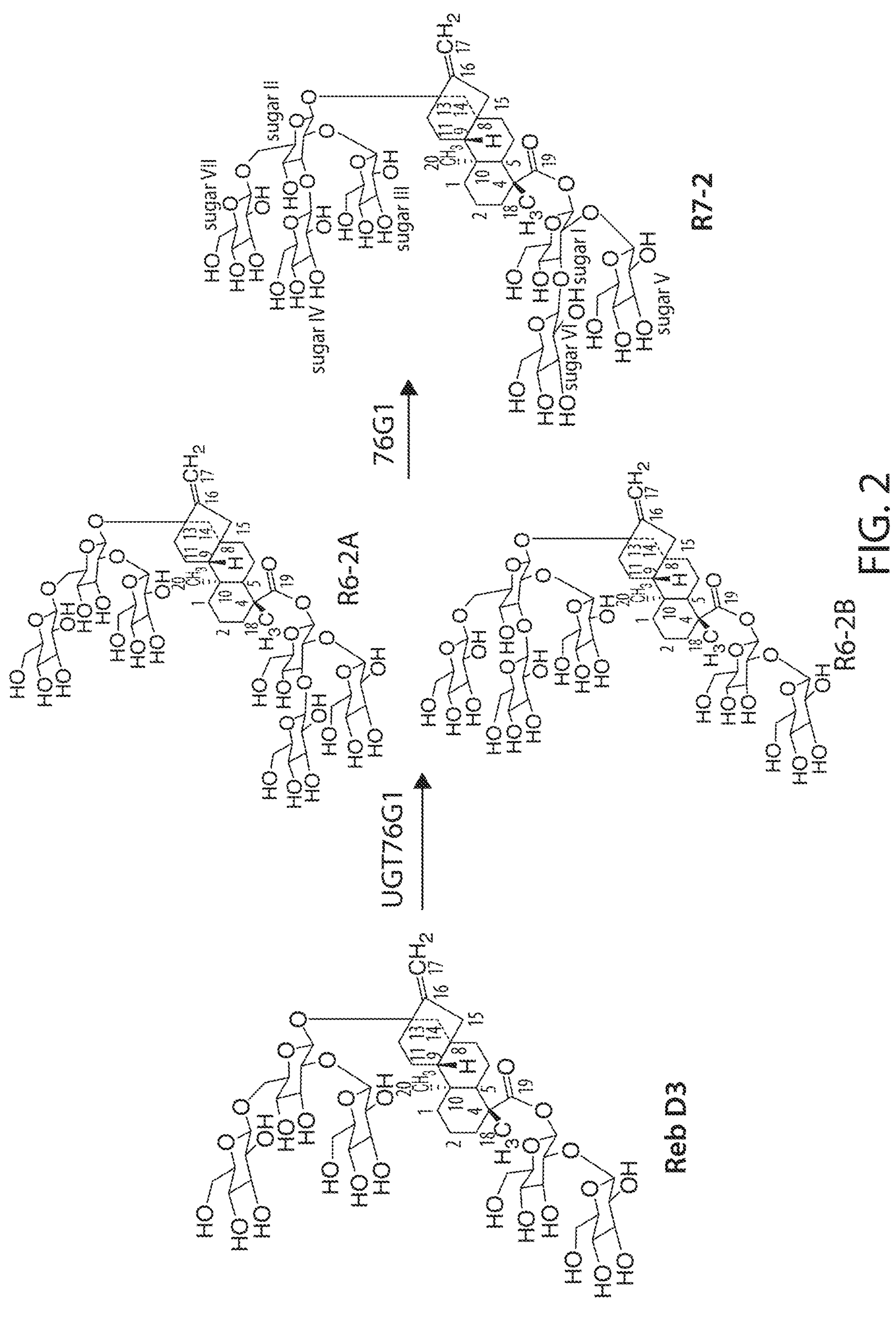
FIG. 2. Biosynthetic pathway of R6-2 and R7-2.

In some embodiments of any one of the methods or compositions provided herein, a glucose is covalently coupled to the rebaudioside D3 by the enzyme to produce rebaudioside R6-2A and/or R6-2B. In some embodiments of any one of the methods or compositions provided herein, the glucose is covalently coupled to sugar I of rebaudioside D3 by the enzyme to produce rebaudioside R6-2A. In some embodiments of any one of the methods or compositions provided herein, the glucose is covalently coupled to sugar II of rebaudioside D3 by the enzyme to produce rebaudioside R6-2B. FIG. 2 illustrates the numbering of sugars in rebaudioside D3, R6-2A, and R6-2B.

In some embodiments of any one of the methods or compositions provided herein, the enzyme for producing a rebaudioside R6-2A and/or R6-2B from rebaudioside D3 comprises a UDP-glycosyltransferase (UGT). In some embodiments of any one of the methods or compositions provided herein, the UGT is a uridine diphospho glycosyltransferase (e.g., UGT76G1 or a functional variant thereof). UGT76G1 is a UGT with a 1,3-13-O-glucose glycosylation activity. It has also been shown that UGT76G1 has 1,3-19-O-glucose glycosylation activity. In some embodiments of any one of the methods or compositions provided herein, the UGT76G1 is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 1. In some embodiments, the UGT76G1 is at least? 70%, 75%, 80%, 85%, 90%, 95%, or 99% identical to the amino acid sequence of SEQ ID NO: 1. In some embodiments, the UGT76G1 comprises the amino acid sequence of SEQ ID NO: 1. In some embodiments, the UGT76G1 consists essentially of or consists of the amino acid sequence of SEQ ID NO: 1.

In some embodiments of any one of the methods or compositions provided herein, the enzyme for producing a rebaudioside R6-2A and/or R6-2B from rebaudioside D3 comprises a UDP-glycosyltransferase (UGT) and a sucrose synthase separately added to the reaction mixture. In some embodiments of any one of the methods or compositions provided herein, the UGT is UGT76G1 and variants as described herein, and the sucrose synthase is selected from the group consisting of an *Arabidopsis* sucrose synthase I, an *Arabidopsis* sucrose synthase 3 and a *Vigna radiate* sucrose synthase. In some embodiments of any one of the methods or compositions provided herein, the sucrose synthase or sucrose synthase domain is an *Arabidopsis thaliana* sucrose synthase I. In some embodiments, the *Arabidopsis thaliana* sucrose synthase I is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 9. In some embodiments, the *Arabidopsis thaliana* sucrose synthase I is at least? 70%, 75%, 80%, 85%, 90%, 95%, or 99% identical to the amino acid sequence of SEQ ID NO: 9. In some embodiments of any one of the methods or compositions provided herein, the *Arabidopsis thaliana* sucrose synthase I comprises the amino acid sequence of SEQ ID NO: 9. In some embodiments of any one of the methods or compositions provided herein, the *Arabidopsis thaliana* sucrose synthase I consists essentially of or consists of the amino acid sequence of SEQ ID NO: 9.

In some embodiments of any one of the methods or compositions provided herein, the enzyme for producing a rebaudioside R6-2A and/or R6-2B from rebaudioside D3 comprises a UDP-glycosyltransferase fusion enzyme comprising a UDP-glycosyltransferase domain coupled to a sucrose synthase domain. The fusion enzyme has the activity of the UDP-glycosyltransferase and sucrose synthase activity. In some embodiments of any one of the methods or compositions provided herein, the UDP-glycosyltransferase domain in the fusion enzyme is any one of the UGT76G1 and variants as described herein, and the sucrose synthase domain is any one of the sucrose synthase (e.g., an *Arabidopsis* sucrose synthase I, an *Arabidopsis* sucrose synthase 3, or a *Vigna radiate* sucrose synthase) and variants as described herein. In some embodiments of any one of the methods or compositions provided herein, the fusion enzyme is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 5. In some embodiments of any one of the methods or compositions provided herein, the fusion enzyme is at least? 70%, 75%, 80%, 85%, 90%, 95%, or 99% identical to the amino acid sequence of SEQ ID NO: 5. In some embodiments of any one of the methods or compositions provided herein, the fusion enzyme comprises the amino acid sequence of SEQ ID NO: 5. In some embodiments of any one of the methods or compositions provided herein, the fusion enzyme consists essentially of or consists of the amino acid sequence of SEQ ID NO: 5.

In some embodiments, any one of the methods of producing rebaudioside R6-2A and/or R6-2B described herein further comprises a step of producing rebaudioside D3. In some embodiments of any one of the methods provided herein, Rebaudioside D3 can be produced by incubating rebaudioside E with a UDP-glycotransferase with and a substrate selected from the group consisting of sucrose, UDP, UDP-glucose, and combinations thereof. In some embodiments of any one of the methods provided herein, the UDP-glycotransferase used to produce rebaudioside D3 from rebaudioside E is EUGT11. Methods of producing rebaudioside D3 from rebaudioside E is described in U.S. Pat. No. 9,765,104, and such methods are incorporated herein by reference. Rebaudioside D3 has the structure of:

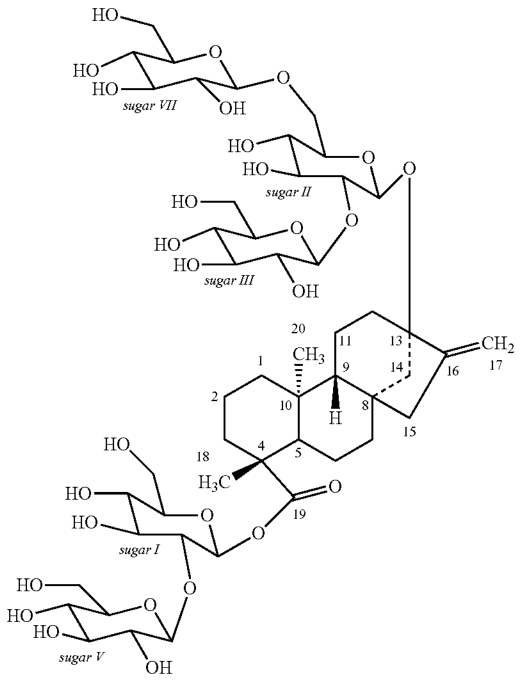

In some embodiments, any one the methods of producing rebaudioside R6-2A and/or R6-2B described herein further comprises isolating the produced rebaudioside R6-2A and/or R6-2B.

Synthetic Rebaudioside R7-2 and Methods of Producing

Some aspects of the present disclosure provide a sweetener (e.g., non-caloric and/or synthetic) that has been given the name "Rebaudioside R7-2 (Reb R7-2)." The Reb R7-2 compound is a steviol glycoside with four glucosyl moieties attached at the C-13 hydroxyl of which three are attached in the form of an ether as a 2,3-branched glucotriosyl substituent; and another 2,3-branched glucotriosyl moiety at C-19 as an ester.

Rebaudioside R7-2 has the molecular formula of $C_{62}H_{100}O_{38}$ and has the structure of:

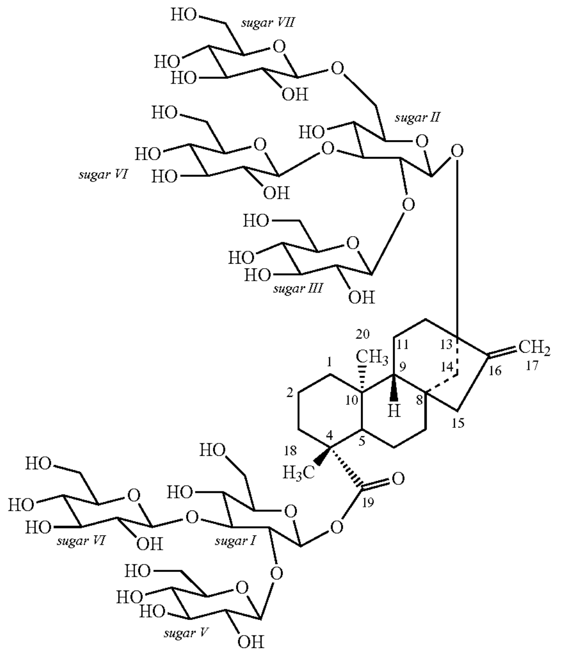

Some aspects of the present disclosure provide methods of producing rebaudioside R7-2. In some embodiments of any one of the methods provided, the rebaudioside R7-2 is produced from one or more of rebaudioside D3, rebaudioside R6-2A, and rebaudioside R6-2B. The reaction mixture for producing rebaudioside R7-2 can be the same as the reaction mixture for producing rebaudioside R6-2A and/or R6-2B. A glucose can be covalently coupled to the rebaudioside D3 by the enzyme to produce rebaudioside R6-2A and/or R6-2B. The enzyme can further covalently couple a second glucose to rebaudioside R6-2A and/or R6-2B, yielding rebaudioside R7-2. In some embodiments of any one of the methods or compositions provided herein, a glucose is covalently coupled to each of sugar I and sugar II of rebaudioside D3 by the enzyme to produce rebaudioside R7-2. FIG. 2 illustrates the numbering of sugars in rebaudioside D3 and rebaudioside R7-2.

In some embodiments of any one of the methods provided, the method comprises (I) preparing a reaction mixture comprising: (i) one or more of rebaudioside D3, rebaudioside R6-2A, and rebaudioside R6-2B; (ii) one or more substrates selected from the group consisting of sucrose, uridine diphosphate (UDP), uridine diphosphate-glucose (UDP-glucose), and combinations thereof; and (iii) an enzyme selected from the group consisting of: (a) a UDP-glycosyltransferase (UGT); (b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain; and (II) incubating the reaction mixture for a sufficient time to produce rebaudioside R7-2.

In some embodiments of any one of the methods or compositions provided herein, the enzyme for producing a rebaudioside R7-2 from rebaudioside D3 comprises a UDP-glycosyltransferase (UGT). In some embodiments of any one of the methods or compositions provided herein, the UGT is a uridine diphospho glycosyltransferase (e.g., UGT76G1 or a functional variant thereof). UGT76G1 is a UGT with a 1,3-13-O-glucose glycosylation activity. It has also been shown that UGT76G1 has 1,3-19-O-glucose glycosylation activity. In some embodiments of any one of the methods or compositions provided herein, the UGT76G1 is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 1. In some embodiments of any one of the methods or compositions provided herein, the UGT76G1 is at least? 70%, 75%, 80%, 85%, 90%, 95%, or 99% identical to the amino acid sequence of SEQ ID NO: 1. In some embodiments of any one of the methods or compositions provided herein, the UGT76G1 comprises the amino acid sequence of SEQ ID NO: 1. In some embodiments of any one of the methods or compositions provided herein, the UGT76G1 consists essentially of or consists of the amino acid sequence of SEQ ID NO: 1.

In some embodiments of any one of the methods or compositions provided herein, the enzyme for producing a rebaudioside R7-2 from rebaudioside D3 comprises a UDP-glycosyltransferase (UGT) and a sucrose synthase separately added to the reaction mixture. In some embodiments of any one of the methods or compositions provided herein, the UGT is UGT76G1 and variants as described herein, and the sucrose synthase is selected from the group consisting of an *Arabidopsis* sucrose synthase I, an *Arabidopsis* sucrose synthase 3 and a *Vigna radiate* sucrose synthase. In some embodiments of any one of the methods or compositions provided herein, the sucrose synthase or sucrose synthase domain is an *Arabidopsis thaliana* sucrose synthase I. In some embodiments of any one of the methods or compositions provided herein, the *Arabidopsis thaliana* sucrose synthase I is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 9. In some embodiments of any one of the methods or compositions provided herein, the *Arabidopsis thaliana* sucrose synthase I is at least? 70%, 75%, 80%, 85%, 90%, 95%, or 99% identical to the amino acid sequence of SEQ ID NO: 9. In some embodiments of any one of the methods or compositions provided herein, the *Arabidopsis thaliana* sucrose synthase I comprises the amino acid sequence of SEQ ID NO: 9. In some embodiments of any one of the methods or compositions provided herein, the *Arabidopsis thaliana* sucrose synthase I consists essentially of or consists of the amino acid sequence of SEQ ID NO: 9.

In some embodiments of any one of the methods or compositions provided herein, the enzyme for producing a rebaudioside R7-2 from rebaudioside D3 comprises a UDP-glycosyltransferase fusion enzyme comprising a UDP-glycosyltransferase domain coupled to a sucrose synthase domain. The fusion enzyme has the activity of the UDP-glycosyltransferase and sucrose synthase activity. In some embodiments of any one of the methods or compositions provided herein, the UDP-glycosyltransferase domain in the fusion enzyme is any one of the UGT76G1 and variants as described herein, and the sucrose synthase domain is any one of the sucrose synthase (e.g., an *Arabidopsis* sucrose synthase I, an *Arabidopsis* sucrose synthase 3, or a *Vigna radiate* sucrose synthase) and variants as described herein. In some embodiments of any one of the methods or compositions provided herein, the fusion enzyme is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 5. In some embodiments of any one of the methods or compositions provided herein, the fusion enzyme is at least? 70%, 75%, 80%, 85%, 90%, 95%, or 99% identical to the amino acid sequence of SEQ ID NO: 5. In some embodiments of any one of the methods or compositions provided herein, the fusion enzyme comprises the amino acid sequence of SEQ ID NO: 5. In some embodiments of any one of the methods or compositions provided herein, the fusion enzyme consists essentially of or consists of the amino acid sequence of SEQ ID NO: 5.

In some embodiments of any one of the methods or compositions provided herein, the methods of producing rebaudioside R7-2 described herein further comprises a step of producing rebaudioside D3. In some embodiments, Rebaudioside D3 can be produced by incubating rebaudioside E with a UDP-glycotransferase with and a substrate selected from the group consisting of sucrose, UDP, UDP-glucose, and combinations thereof. In some embodiments of any one of the methods or compositions provided herein, the UDP-glycotransferase used to produce rebaudioside D3 from rebaudioside E is EUGT11. Methods of producing rebaudioside D3 from rebaudioside E is described in U.S. Pat. No. 9,765,104, such methods are incorporated herein by reference. Rebaudioside D3 has the structure of:

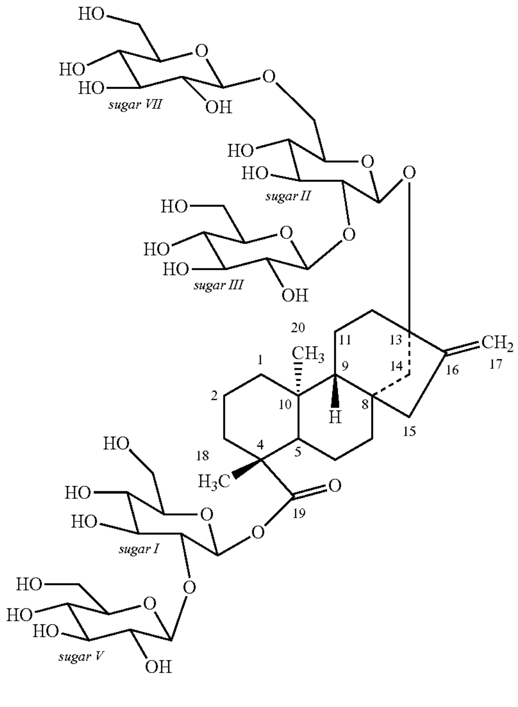

In some embodiments, any one of the methods of producing rebaudioside R7-2 described herein further comprises isolating the produced rebaudioside R7-2.

Synthetic Rebaudioside R6-4A and R6-4B and Methods of Producing

Some aspects of the present disclosure provide a sweetener (e.g., non-caloric and/or synthetic) that has been given the name "Rebaudioside R6-4A (Reb R6-4A)." Rebaudioside R6-4A has the molecular formula of $C_{56}H_9O_{33}$ and has the structure of:

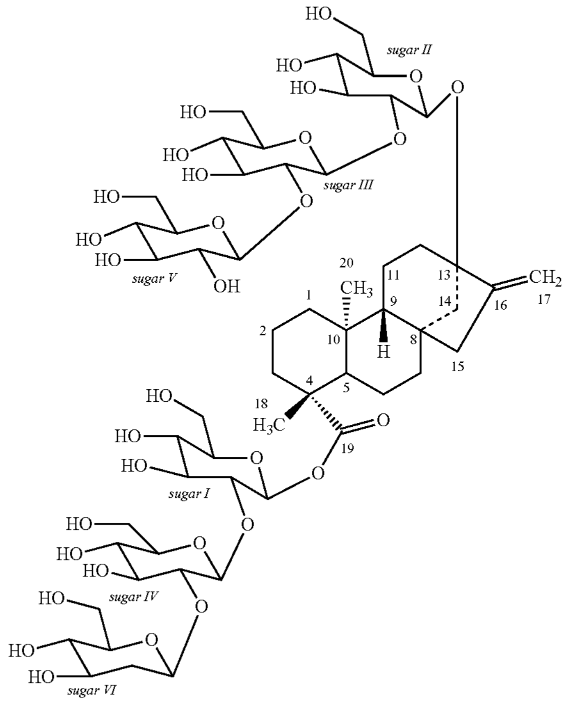

Some aspects of the present disclosure provide a sweetener (e.g., non-caloric and/or synthetic) that has been given the name "Rebaudioside R6-4B (Reb R6-4B)." Rebaudioside R6-4B has the molecular formula of $C_{56}H_{90}O_{33}$ and has the structure of:

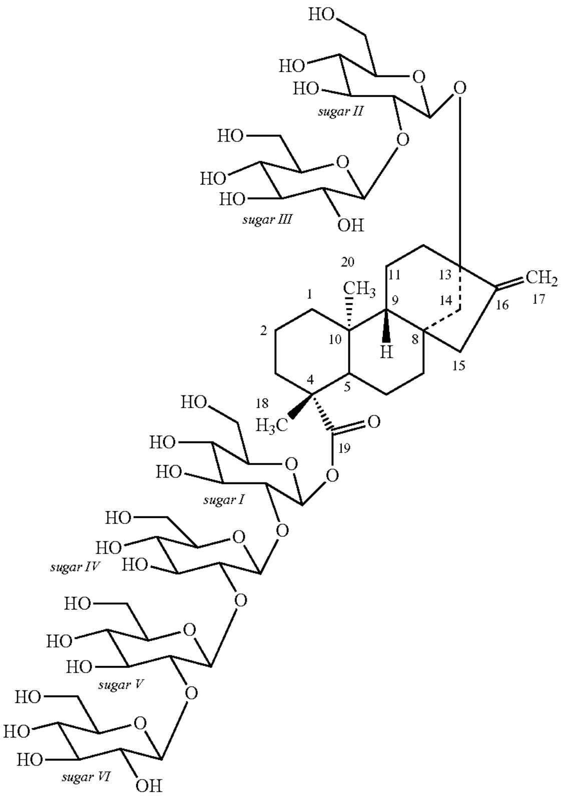

Some aspects of the present disclosure provide methods of producing rebaudioside R6-4A. In some embodiments of any one of the methods provided, the rebaudioside R6-4A is produced from rebaudioside Z1 or rebaudioside Z2. For example, in some embodiments, the method comprises (I) preparing a reaction mixture comprising: (i) rebaudioside Z1 or rebaudioside Z2; (ii) one or more substrates selected from the group consisting of sucrose, uridine diphosphate (UDP), uridine diphosphate-glucose (UDP-glucose), and combinations thereof; and (iii) an enzyme selected from the group consisting of: (a) a UDP-glycosyltransferase (UGT); (b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain; and (II) incubating the reaction mixture for a sufficient time to produce rebaudioside R6-4A.

Figure 14:
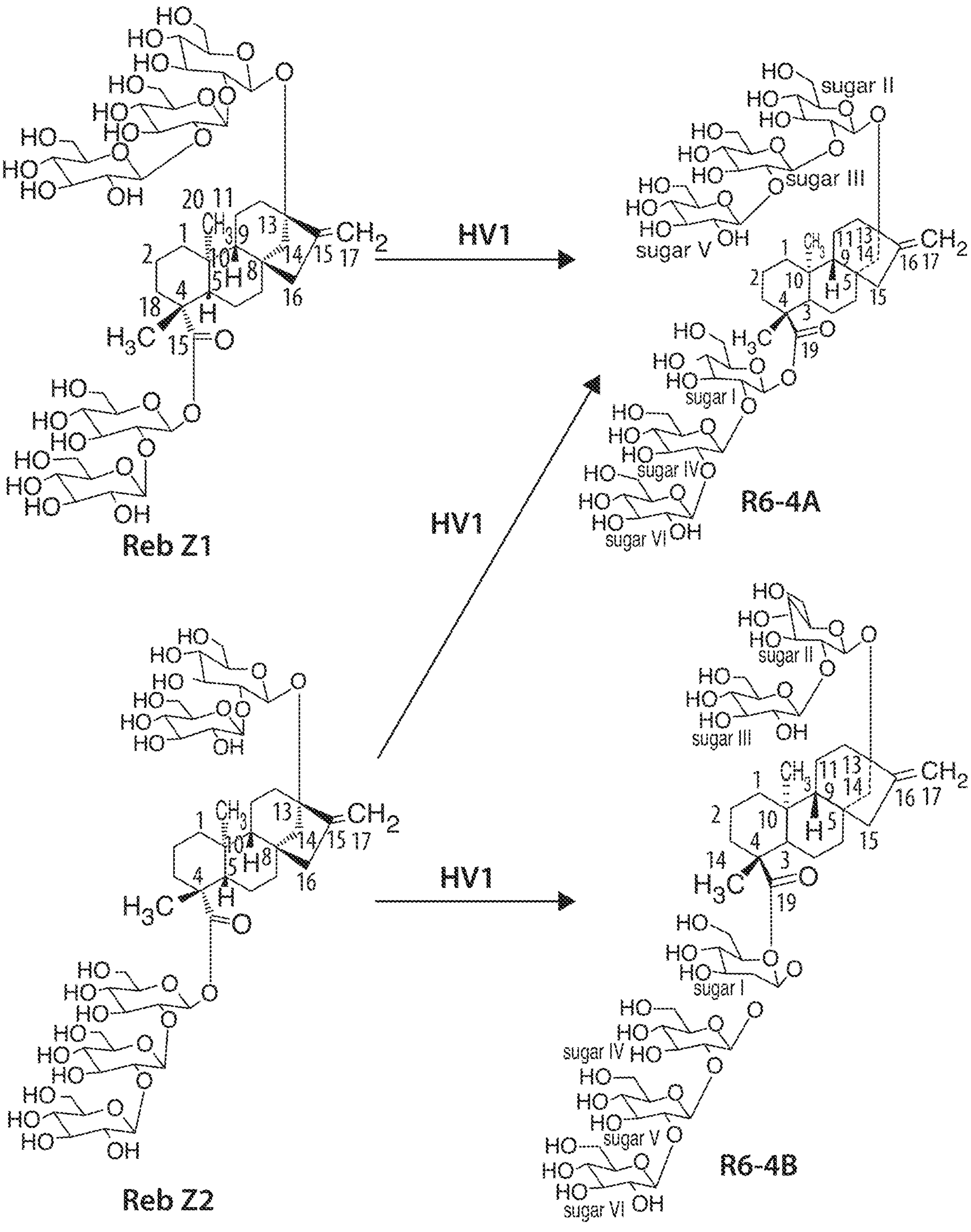
FIG. 14. The biosynthesis pathway of R6-4A and R6-4B compound.

In some embodiments of any one of the methods or compositions provided herein, a glucose is covalently coupled to the rebaudioside Z1 or rebaudioside Z2 by the enzyme to produce rebaudioside R6-4A. In some embodiments of any one of the methods or compositions provided herein, the glucose is covalently coupled to sugar IV of rebaudioside Z1 by the enzyme to produce rebaudioside R6-4A. In some embodiments of any one of the methods or compositions provided herein, the glucose is covalently coupled to sugar III of rebaudioside Z2 by the enzyme to produce rebaudioside R6-4A. FIG. 14 illustrates the numbering of sugars in rebaudioside Z1, Z2, and R6-4A.

Some aspects of the present disclosure provide methods of producing rebaudioside R6-4B. In some embodiments of any one of the methods provided, the rebaudioside R6-4B is produced from rebaudioside Z2. For example, in some embodiments, the method comprises (I) preparing a reaction mixture comprising: (i) rebaudioside Z2; (ii) one or more substrates selected from the group consisting of sucrose, uridine diphosphate (UDP), uridine diphosphate-glucose (UDP-glucose), and combinations thereof; and (iii) an enzyme selected from the group consisting of: (a) a UDP-glycosyltransferase (UGT); (b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain; and (II) incubating the reaction mixture for a sufficient time to produce rebaudioside R6-4B.

In some embodiments of any one of the methods or compositions provided herein, a glucose is covalently coupled to the rebaudioside Z2 by the enzyme to produce rebaudioside R6-4B. In some embodiments of any one of the methods or compositions provided herein, the glucose is covalently coupled to sugar V of rebaudioside Z2 by the enzyme to produce rebaudioside R6-4B. FIG. 14 illustrates the numbering of sugars in rebaudioside Z2 and R6-4B.

In some embodiments of any one of the methods or compositions provided herein, the enzyme for producing a rebaudioside R6-4A or R6-4B from rebaudioside Z1 or Z2 comprises a UDP-glycosyltransferase (UGT). In some embodiments of any one of the methods or compositions provided herein, the UGT is a HV1 glycosyltransferase. HV1 is a UGT with a 1 a 1,2-19-O-glucose glycosylation activity. It has also been shown that HV1 UGT has 1,2-19-O-glucose glycosylation activity. In some embodiments of any one of the methods or compositions provided herein, the HV1 UGT is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 3. In some embodiments of any one of the methods or compositions provided herein, the HV1 UGT is at least? 70%, 75%, 80%, 85%, 90%, 95%, or 99% identical to the amino acid sequence of SEQ ID NO: 3. In some embodiments of any one of the methods or compositions provided herein, the HV1 UGT comprises the amino acid sequence of SEQ ID NO: 3. In some embodiments of any one of the methods or compositions provided herein, the HV1 UGT consists essentially of or consists of the amino acid sequence of SEQ ID NO: 3.

In some embodiments of any one of the methods provided herein, the enzyme for producing a rebaudioside R6-4A and/or R6-4B from rebaudioside Z1 or Z2 comprises a UDP-glycosyltransferase (UGT) and a sucrose synthase separately added to the reaction mixture. In some embodiments of any one of the methods or compositions provided herein, the UGT is HV1 UGT and variants as described herein, and the sucrose synthase is selected from the group consisting of an *Arabidopsis* sucrose synthase I, an *Arabidopsis* sucrose synthase 3 and a *Vigna radiate* sucrose synthase. In some embodiments of any one of the methods or compositions provided herein, the sucrose synthase or sucrose synthase domain is an *Arabidopsis thaliana* sucrose synthase I. In some embodiments, the *Arabidopsis thaliana* sucrose synthase I is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 9. In some embodiments of any one of the methods or compositions provided herein, the *Arabidopsis thaliana* sucrose synthase I is at least? 70%, 75%, 80%, 85%, 90%, 95%, or 99% identical to the amino acid sequence of SEQ ID NO: 9. In some embodiments of any one of the methods or compositions provided herein, the *Arabidopsis thaliana* sucrose synthase I comprises the amino acid sequence of SEQ ID NO: 9. In some embodiments of any one of the methods or compositions provided herein, the *Arabidopsis thaliana* sucrose synthase I consists essentially of or consists of the amino acid sequence of SEQ ID NO: 9.

In some embodiments of any one of the methods provided herein, the enzyme for producing a rebaudioside R6-4A or R6-4B from rebaudioside Z1 or Z2 comprises a UDP-glycosyltransferase fusion enzyme comprising a UDP-glycosyltransferase domain coupled to a sucrose synthase domain. The fusion enzyme has the activity of the UDP-glycosyltransferase and sucrose synthase activity. In some embodiments of any one of the methods or compositions provided herein, the UDP-glycosyltransferase domain in the fusion enzyme is any one of the HV1 UGT and variants as described herein, and the sucrose synthase domain is any one of the sucrose synthase (e.g., an *Arabidopsis* sucrose synthase I, an *Arabidopsis* sucrose synthase 3, or a *Vigna radiate* sucrose synthase) and variants as described herein. In some embodiments of any one of the methods or compositions provided herein, the fusion enzyme is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 7. In some embodiments of any one of the methods or compositions provided herein, the fusion enzyme is at least? 70%, 75%, 80%, 85%, 90%, 95%, or 99% identical to the amino acid sequence of SEQ ID NO: 7. In some embodiments of any one of the methods or compositions provided herein, the fusion enzyme comprises the amino acid sequence of SEQ ID NO: 7. In some embodiments of any one of the methods or compositions provided herein, the fusion enzyme consists essentially of or consists of the amino acid sequence of SEQ ID NO: 7.

In some embodiments, any one of the methods of producing rebaudioside R6-4A and/or R6-4B described herein further comprises a step of producing rebaudioside Z1 and/or Z2. In some embodiments of any one of the methods provided herein, rebaudioside Z1 and/or Z2 can be produced by incubating rebaudioside E with a UDP-glycosyltransferase with and a substrate selected from the group consisting of sucrose, UDP, UDP-glucose, and combinations thereof. In some embodiments of any one of the methods or compositions provided herein, the UDP-glycotransferase used to produce rebaudioside Z1 and/or Z2 from rebaudioside E is UGT76G1. Methods of producing rebaudioside D3 from rebaudioside E is described in U.S. Pat. No. 10,081,826, such methods incorporated herein by reference.

Rebaudioside Z1 has the structure of:

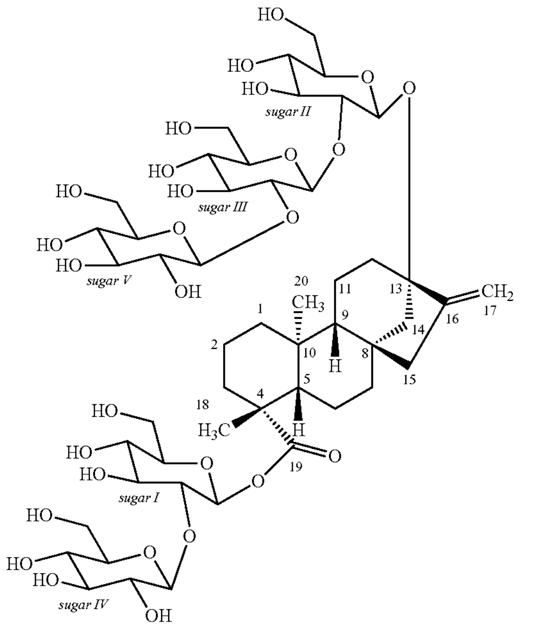

Rebaudioside Z2 has the structure of:

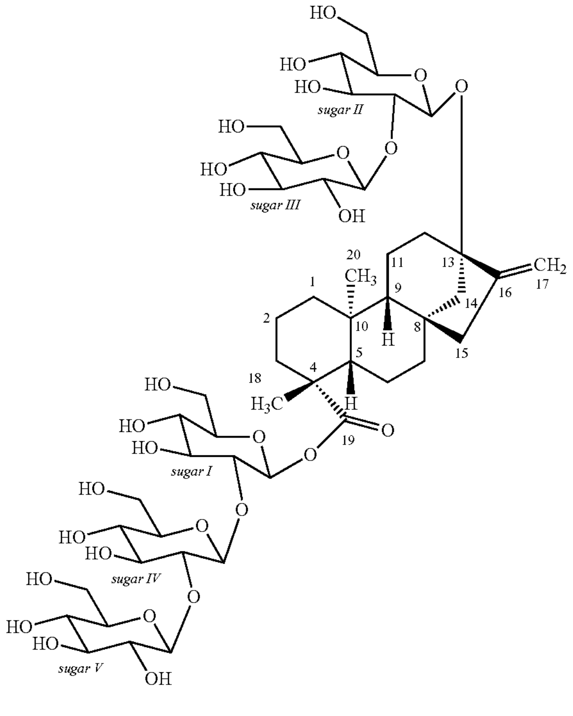

In some embodiments, any one of the methods of producing rebaudioside R6-4A and/or R6-4B described herein further comprises isolating the produced rebaudioside R6-4A and/or R6-4B.

Synthetic Rebaudioside R6-1 and Methods of Producing

Some aspects of the present disclosure provide a sweetener (e.g., non-caloric and/or synthetic) that has been given the name "Rebaudioside R6-1 (Reb R6-1)." Rebaudioside R6-1 has the molecular formula of $C_{56}H_{90}O_{33}$ and has the structure of:

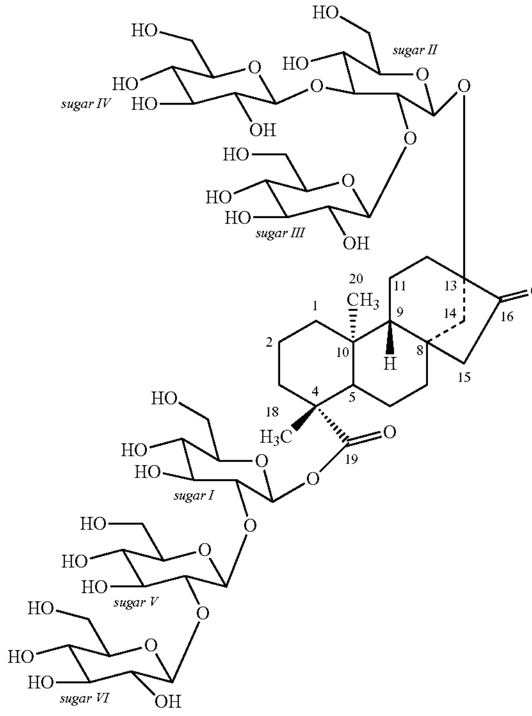

Some aspects of the present disclosure provide methods of producing rebaudioside R6-1. In some embodiments of any one of the methods provided herein, the rebaudioside R6-1 is produced from rebaudioside D. For example, in some embodiments, the method comprises (I) preparing a reaction mixture comprising: (i) rebaudioside D; (ii) one or more substrates selected from the group consisting of sucrose, uridine diphosphate (UDP), uridine diphosphate-glucose (UDP-glucose), and combinations thereof; and (iii) an enzyme selected from the group consisting of: (a) a UDP-glycosyltransferase (UGT); (b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain; and (II) incubating the reaction mixture for a sufficient time to produce rebaudioside R6-1.

Figure 9:
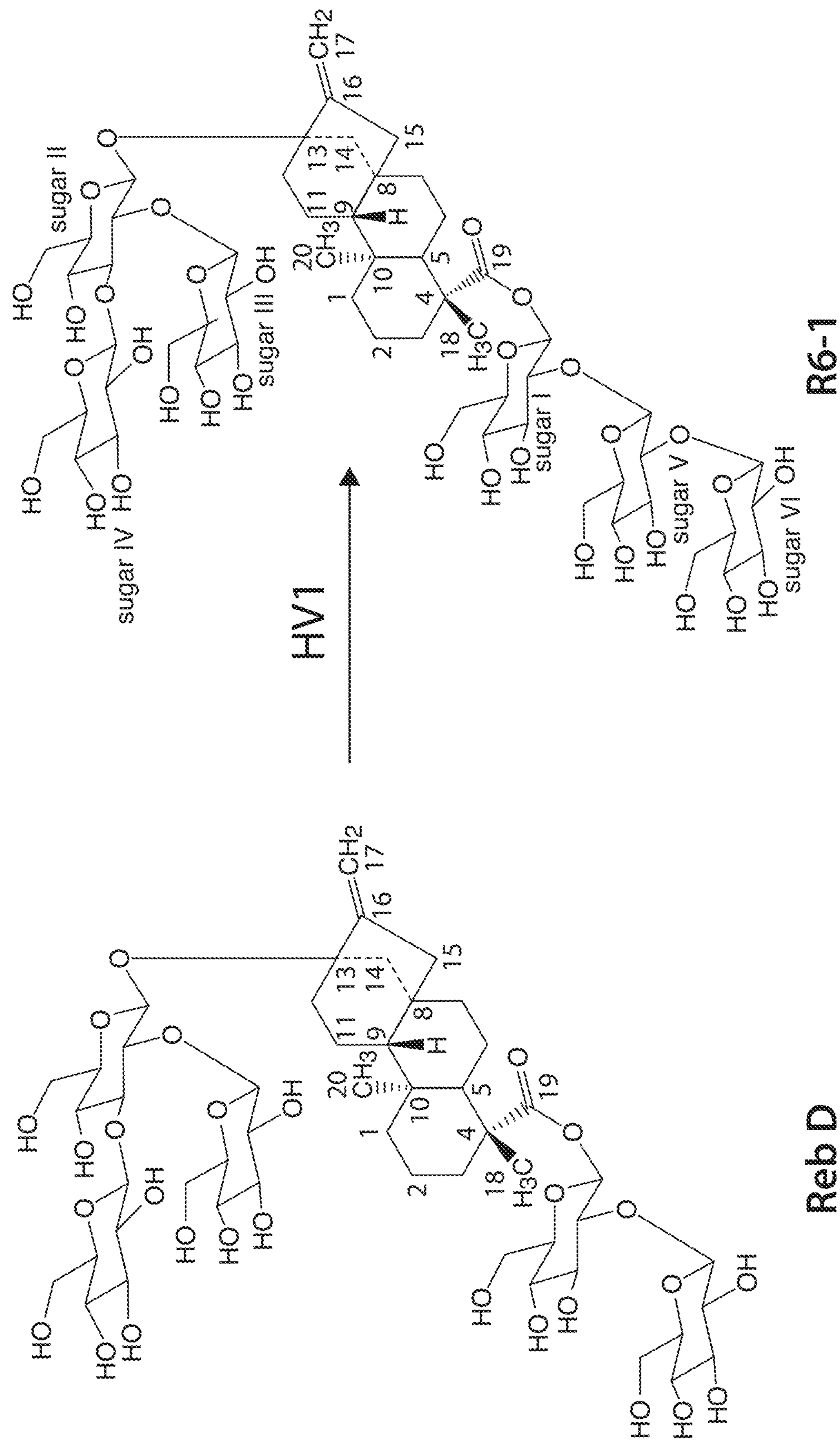
FIG. 9. The biosynthesis pathway of R6-1 compound.

In some embodiments of any one of the methods or compositions provided herein, a glucose is covalently coupled to the rebaudioside D by the enzyme to produce rebaudioside R6-1. In some embodiments of any one of the methods or compositions provided herein, the glucose is covalently coupled to sugar V of rebaudioside D by the enzyme to produce rebaudioside R6-1. FIG. 9 illustrates the numbering of sugars in rebaudioside D and R6-1.

In some embodiments of any one of the methods provided herein, the enzyme for producing a rebaudioside R6-1 from rebaudioside D comprises a UDP-glycosyltransferase (UGT). In some embodiments of any one of the methods or compositions provided herein, the UGT is a HV1 glycosyltransferase. HV1 is a UGT with a 1 a 1,2-19-O-glucose glycosylation activity. It has also been shown that HV1 UGT has 1,2-19-O-glucose glycosylation activity. In some embodiments of any one of the methods or compositions provided herein, the HV1 UGT is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 3. In some embodiments of any one of the methods or compositions provided herein, the HV1 UGT is at least? 70%, 75%, 80%, 85%, 90%, 95%, or 99% identical to the amino acid sequence of SEQ ID NO: 3. In some embodiments of any one of the methods or compositions provided herein, the HV1 UGT comprises the amino acid sequence of SEQ ID NO: 3. In some embodiments of any one of the methods or compositions provided herein, the HV1 UGT consists essentially of or consists of the amino acid sequence of SEQ ID NO: 3.

In some embodiments of any one of the methods provided herein, the enzyme for producing a rebaudioside R6-1 from rebaudioside D comprises a UDP-glycosyltransferase (UGT) and a sucrose synthase separately added to the reaction mixture. In some embodiments of any one of the methods or compositions provided herein, the UGT is HV1 UGT and variants as described herein, and the sucrose synthase is selected from the group consisting of an *Arabidopsis* sucrose synthase I, an *Arabidopsis* sucrose synthase 3 and a *Vigna radiate* sucrose synthase. In some embodiments of any one of the methods or compositions provided herein, the sucrose synthase or sucrose synthase domain is an *Arabidopsis thaliana* sucrose synthase I. In some embodiments of any one of the methods or compositions provided herein, the *Arabidopsis thaliana* sucrose synthase I is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 9. In some embodiments of any one of the methods or compositions provided herein, the *Arabidopsis thaliana* sucrose synthase I is at least? 70%, 75%, 80%, 85%, 90%, 95%, or 99% identical to the amino acid sequence of SEQ ID NO: 9. In some embodiments of any one of the methods or compositions provided herein, the *Arabidopsis thaliana* sucrose synthase I comprises the amino acid sequence of SEQ ID NO: 9. In some embodiments of any one of the methods or compositions provided herein, the *Arabidopsis thaliana* sucrose synthase I consists essentially of or consists of the amino acid sequence of SEQ ID NO: 9.

In some embodiments of any one of the methods provided herein, the enzyme for producing a rebaudioside R6-1 from rebaudioside D comprises a UDP-glycosyltransferase fusion enzyme comprising a UDP-glycosyltransferase domain coupled to a sucrose synthase domain. The fusion enzyme has the activity of the UDP-glycosyltransferase and sucrose synthase activity. In some embodiments of any one of the methods or compositions provided herein, the UDP-glycosyltransferase domain in the fusion enzyme is any one of the HV1 UGT and variants as described herein, and the sucrose synthase domain is any one of the sucrose synthase (e.g., an *Arabidopsis* sucrose synthase I, an *Arabidopsis* sucrose synthase 3, or a *Vigna radiate* sucrose synthase) and variants as described herein. In some embodiments of any one of the methods or compositions provided herein, the fusion enzyme is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the amino acid sequence of SEQ ID NO: 7. In some embodiments of any one of the methods or compositions provided herein, the fusion enzyme is at least? 70%, 75%, 80%, 85%, 90%, 95%, or 99% identical to the amino acid sequence of SEQ ID NO: 7. In some embodiments of any one of the methods or compositions provided herein, the fusion enzyme comprises the amino acid sequence of SEQ ID NO: 7. In some embodiments of any one of the methods or compositions provided herein, the fusion enzyme consists essentially of or consists of the amino acid sequence of SEQ ID NO: 7.

In some embodiments, any one of the methods of producing rebaudioside R6-1 described herein further comprises a step of producing rebaudioside D. In some embodiments of any one of the methods provided, rebaudioside D can be produced by incubating rebaudioside A with a UDP-glycotransferase with and a substrate selected from the group consisting of sucrose, UDP, UDP-glucose, and combinations thereof. In some embodiments of any one of the methods provided, the UDP-glycotransferase used to produce rebaudioside D from rebaudioside A is EUGT11. Methods of producing rebaudioside D from rebaudioside A is described in US Patent Application Publication No. US20180037600, such methods are incorporated herein by reference.

In some embodiments of any one of the methods provided herein, rebaudioside D can be produced by incubating rebaudioside E with a UDP-glycotransferase with and a substrate selected from the group consisting of sucrose, UDP, UDP-glucose, and combinations thereof. In some embodiments of any one of the methods provided, the UDP-glycotransferase used to produce rebaudioside D from rebaudioside E is HV1 UGT or UGT76G1. Methods of producing rebaudioside D from rebaudioside E is described in US Patent Application Publication No. U.S. Pat. No. 10,253,344, such methods are incorporated herein by reference.

Rebaudioside D has the structure of:

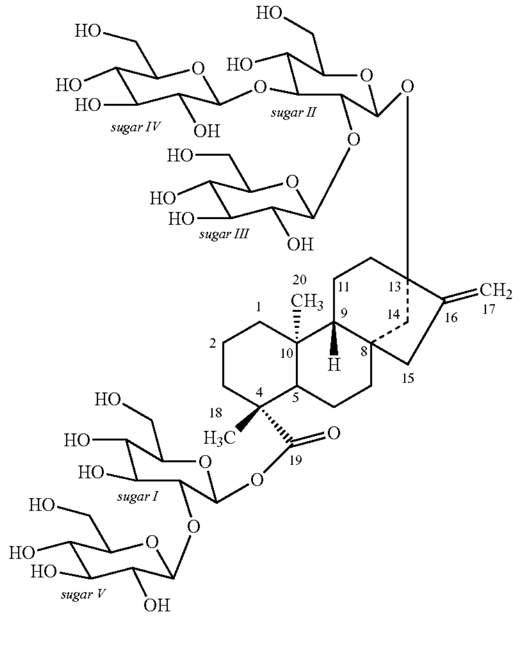

In some embodiments, any one of the methods of producing rebaudioside R6-1 described herein further comprises isolating the producing rebaudioside R6-1.

Reaction Mixtures, Nucleic Acids and Cellular Systems

In some embodiments of any one of the methods provided, the reaction mixture is in vitro, i.e., the method described herein is performed in vitro. For in vitro reactions, isolated enzymes (e.g., UDP-glycosyltransferase, the sucrose synthase, and/or the UDP-glycosyltransferase fusion enzymes) can be added to the in vitro reaction mixture.

In some embodiments of any one of the methods provided, the reaction mixture is a cell-based reaction mixture, i.e., the reaction is performed in a cell. For cell-based reactions, the enzymes (e.g., UDP-glycosyltransferase, the sucrose synthase, and/or the UDP-glycosyltransferase fusion enzymes) are expressed in a host cell.

In some embodiments of any one of the methods provided, the enzymes (e.g., UDP-glycosyltransferase, the sucrose synthase, and/or the UDP-glycosyltransferase fusion enzymes) are expressed from nucleotide sequences encoding them, respectively. As such, nucleic acids encoding any one of the enzymes described herein are provided. The present disclosure further provides host cells comprising a nucleotide sequence having at least 80% (e.g., at least 80%, at least 85%, at least 90%, at least 95%, at least 96%, at least 97%, at least 98%, at least 99% or 100%) identity to any one of SEQ ID NOs: 2, 4, 6, 8, and 10. In some embodiments of any one of the methods provided, the host cell comprises a nucleotide sequence having at least 80% (e.g., at least 80%, at least 85%, at least 90%, at least 95%, at least 96%, at least 97%, at least 98%, at least 99% or 100%) identity to SEQ ID NO: 2 and a nucleotide sequence having at least 80% (e.g., at least 80%, at least 85%, at least 90%, at least 95%, at least 96%, at least 97%, at least 98%, at least 99% or 100%) identity to SEQ ID NO: 10. In some embodiments of any one of the methods provided, the host cell comprises a nucleotide sequence having at least 80% (e.g., at least 80%, at least 85%, at least 90%, at least 95%, at least 96%, at least 97%, at least 98%, at least 99% or 100%) identity to SEQ ID NO: 4 and a nucleotide sequence having at least 80% (e.g., at least 80%, at least 85%, at least 90%, at least 95%, at least 96%, at least 97%, at least 98%, at least 99% or 100%) identity to SEQ ID NO: 10.

In some embodiments of any one of the methods provided, the host cell is selected from the group consisting of a yeast, a non-steviol glycoside producing plant, an alga, a fungus, and a bacterium.

In some embodiments of any one of the methods provided, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea*; and *Clostridium*. In some embodiments of any one of the methods provided, the host cell is a bacterial cell (e.g., an *E. coli* cell). In some embodiments of any one of the methods provided, the host cell is a yeast cell (e.g., a *Saccharomyces cerevisiae* cell).

In some embodiments of any one of the methods provided, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees;

forage grasses; *Arabidopsis thaliana*; rice (*Oryza sativa*); *Hordeum yulgare*; switchgrass (*Panicum vigratum*); *Brachypodium* spp.; *Brassica* spp.; and *Crambe abyssinica.*

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and, 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR).

Several molecular biology techniques can be developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or *E. coli* DNA polymerase I, enzymes that remove protruding, 3'-single-stranded termini with their 3'-5'-exonucleolytic activities and fill in recessed 3'-ends with their polymerizing activities, thereby generating blunt ended DNA segments. The blunt-ended segments are then incubated with a large molar excess of linker molecules in the presence of an enzyme that can catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, Nucl. Acid. Res. 18 6069-74, (1990), Haun, et al, Biotechniques 13, 515-18 (1992), which is incorporated herein by reference to the extent it is consistent herewith).

In an embodiment, to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared using PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector, In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a petunia plant cell.

Microbial host cell expression systems and expression vectors containing regulatory sequences that direct high-level expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically, the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. In some embodiments, it is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYCI, HIS3, GALI, GALIO, ADHI, PGK, PH05, GAPDH, ADCI, TRPI, URA3, LEU2, ENO, TPI (useful for expression in *Saccharomyces*); AOXI (useful for expression in *Pichia*); and lac, trp, JPL, IPR, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with an expression vector of the subject technology should be capable of promoting the expression of the vector. High level plant promoters that may be used in the subject technology include the promoter of the small subunit (ss) of the ribulose-1,5-bisphosphate carboxylase for example from soybean (Berry-Lowe et al., J. MOLECULAR AND APP. GEN., 1:483 498 (1982), the entirety of which is hereby incorporated herein to the extent it is consistent herewith), and the promoter of the chlorophyll a/b binding protein. These two promoters are known to be light-induced in plant cells (see, for example, GENETIC ENGINEERING OF PLANTS, AN AGRICULTURAL PERSPECTIVE, A. Cashmore, Plenum, N.Y. (1983), pages 29-38; Coruzzi, G. et al., THE JOURNAL OF BIOLOGICAL CHEMISTRY, 258: 1399 (1983), and Dunsmuir, P. et al., JOURNAL OF MOLEC. APPL. GEN., 2:285 (1983), each of which is hereby incorporated herein by reference to the extent they are consistent herewith).

Orally Consumable Products

The rebaudiosides produced using any one of the methods described herein (e.g., rebaudiosides R6-1, R6-2A, R6-2B, R6-4A, R6-4B, and R7-2) can be used as sweeteners. Other aspects of the present disclosure provide an orally consumable product having a sweetening amount of rebaudioside R6-1, rebaudioside R6-2A, rebaudioside R6-2B, rebaudioside R6-4A, rebaudioside R6-4B, and/or rebaudioside R7-2, such as selected from the group consisting of a beverage product and a consumable product.

Any one of the orally consumable products can have a sweetness intensity equivalent to about 1% (w/v-%) to about 4% (w/v-%) sucrose solution.

Any one of the orally consumable products can have from about 5 ppm to about 100 ppm rebaudioside R6-1. Any one of the orally consumable products can have from about 5 ppm to about 100 ppm rebaudioside R6-2A. Any one of the orally consumable products can have from about 5 ppm to about 100 ppm rebaudioside R6-2B. Any one of the orally consumable products can have from about 5 ppm to about 100 ppm rebaudioside R6-4A. Any one of the orally consumable products can have from about 5 ppm to about 100 ppm rebaudioside R6-4B. Any one of the orally consumable products can have from about 5 ppm to about 100 ppm rebaudioside R7-2.

The rebaudioside R6-1 can be the only sweetener in the orally consumable product. The rebaudioside R6-2A can be the only sweetener in the orally consumable product. The rebaudioside R6-2B can be the only sweetener in the orally consumable product. The rebaudioside R6-4A can be the only sweetener in the orally consumable product. The rebaudioside R6-4B can be the only sweetener in the orally consumable product. The rebaudioside R7-2 can be the only sweetener in the orally consumable product.

Any one of the orally consumable products can also have at least one additional sweetener. The at least one additional sweetener can be a natural high intensity sweetener, for example. The additional sweetener can be selected from a stevia extract, a steviol glycoside, stevioside, rebaudioside A, rebaudioside B, rebaudioside C, rebaudioside D, rebaudioside D2, rebaudioside E, rebaudioside F, rebaudioside M, rebaudioside V, rebaudioside W, rebaudioside Z1, rebaudioside Z2, rebaudioside D3, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof.

Any one of the orally consumable products can also have at least one additive. The additive can be, for example, a carbohydrate, a polyol, an amino acid or salt thereof, a polyamino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof.

In some embodiments, the present disclosure provides a beverage product comprising a sweetening amount of rebaudioside R6-1. In some embodiments, the present disclosure provides a beverage product comprising a sweetening amount of rebaudioside R6-2A. In some embodiments, the present disclosure provides a beverage product comprising a sweetening amount of rebaudioside R6-2B. In some embodiments, the present disclosure provides a beverage product comprising a sweetening amount of rebaudioside R6-4A. In some embodiments, the present disclosure provides a beverage product comprising a sweetening amount of rebaudioside R6-4B. In some embodiments, the present disclosure provides a beverage product comprising a sweetening amount of rebaudioside R7-2.

Any one of the beverage products can be, for example, a carbonated beverage product and a non-carbonated beverage product. Any one of the beverage products can also be, for example, a soft drink, a fountain beverage, a frozen beverage; a ready-to-drink beverage; a frozen and ready-to-drink beverage, coffee, tea, a dairy beverage, a powdered soft drink, a liquid concentrate, flavored water, enhanced water, fruit juice, a fruit juice flavored drink, a sport drink, and an energy drink.

In some embodiments, any one of the beverage products of the present disclosure can include one or more beverage ingredients such as, for example, acidulants, fruit juices and/or vegetable juices, pulp, etc., flavorings, coloring, preservatives, vitamins, minerals, electrolytes, erythritol, tagatose, glycerine, and carbon dioxide. Such beverage products may be provided in any suitable form, such as a beverage concentrate and a carbonated, ready-to-drink beverage.

In certain embodiments, any one of the beverage products of the present disclosure can have any of numerous different specific formulations or constitutions. The formulation of a beverage product of the present disclosure can vary to a certain extent, depending upon such factors as the product's intended market segment, its desired nutritional characteristics, flavor profile, and the like. For example, in certain embodiments, it can generally be an option to add further ingredients to the formulation of a particular beverage product. For example, additional (i.e., more and/or other) sweeteners can be added, flavorings, electrolytes, vitamins, fruit juices or other fruit products, tastents, masking agents and the like, flavor enhancers, and/or carbonation typically may be added to any such formulations to vary the taste, mouthfeel, nutritional characteristics, etc. In embodiments, any one of the beverage products can be a cola beverage that contains water, about 5 ppm to about 100 ppm rebaudioside R6-1, an acidulant, and flavoring. In embodiments, any one of the beverage products can be a cola beverage that contains water, about 5 ppm to about 100 ppm rebaudioside R6-2A, an acidulant, and flavoring. In embodiments, any one of the beverage products can be a cola beverage that contains water, about 5 ppm to about 100 ppm rebaudioside R6-2B, an acidulant, and flavoring. In embodiments, any one of the beverage products can be a cola beverage that contains water, about 5 ppm to about 100 ppm rebaudioside R6-4A, an acidulant, and flavoring. In embodiments, any one of the beverage products can be a cola beverage that contains water, about 5 ppm to about 100 ppm rebaudioside R6-4B, an acidulant, and flavoring. In embodiments, any one of the beverage products can be a cola beverage that contains water, about 5 ppm to about 100 ppm rebaudioside R7-2, an acidulant, and flavoring.

Exemplary flavorings can be, for example, cola flavoring, citrus flavoring, and spice flavorings. In some embodiments, carbonation in the form of carbon dioxide can be added for effervescence. In other embodiments, preservatives can be added, depending upon the other ingredients, production technique, desired shelf life, etc. In certain embodiments, caffeine can be added. In some embodiments, the beverage product can be a cola-flavored carbonated beverage, characteristically containing carbonated water, sweetener, kola nut extract and/or other flavoring, caramel coloring, one or more acids, and optionally other ingredients.

Suitable amounts of rebaudioside R6-1, rebaudioside R6-2A, rebaudioside R6-2B, rebaudioside R6-4A, rebaudioside R6-4B, or rebaudioside R7-2 present in the beverage product can be, for example, from about 5 ppm to about 100 ppm. In some embodiments, low concentrations of rebaudioside R6-1, rebaudioside R6-2A, rebaudioside R6-2B, rebaudioside R6-4A, rebaudioside R6-4B, or rebaudioside R7-2, for example, less than 100 ppm, and has an equivalent sweetness to sucrose solutions having concentrations between 10,000 ppm to 30,000 ppm. The final concentration that ranges from about 5 ppm to about 100 ppm, from about 5 ppm to about 95 ppm, from about 5 ppm to about 90 ppm, from about 5 ppm to about 85 ppm, from about 5 ppm to about 80 ppm, from about 5 ppm to about 75 ppm, from about 5 ppm to about 70 ppm, from about 5 ppm to about 65 ppm, from about 5 ppm to about 60 ppm, from about 5 ppm to about 55 ppm, from about 5 ppm to about 50 ppm, from about 5 ppm to about 45 ppm, from about 5 ppm to about 40 ppm, from about 5 ppm to about 35 ppm, from about 5 ppm to about 30 ppm, from about 5 ppm to about 25 ppm, from about 5 ppm to about 20 ppm, from about 5 ppm to about 15 ppm, or from about 5 ppm to about 10 ppm. Alternatively, rebaudioside R6-1, rebaudioside R6-2A, rebaudioside R6-2B, rebaudioside R6-4A, rebaudioside R6-4B, or rebaudioside R7-2 can be present in beverage products of the present disclosure at a final concentration that ranges from about 5 ppm to about 100 ppm, from about 10 ppm to about 100 ppm, from about 15 ppm to about 100 ppm, from about 20 ppm to about 100 ppm, from about 25 ppm to about 100 ppm, from about 30 ppm to about 100 ppm, from about 35 ppm to about 100 ppm, from about 40 ppm to about 100 ppm, from about 45 ppm to about 100 ppm, from about 50 ppm to about 100 ppm, from about 55 ppm to about 100 ppm, from about 60 ppm to about 100 ppm, from about 65 ppm to about 100 ppm, from about 70 ppm to about 100 ppm, from about 75 ppm to about 100 ppm, from about 80 ppm to about 100 ppm, from about 85 ppm to about 100 ppm, from about 90 ppm to about 100 ppm, or from about 95 ppm to about 100 ppm.

In some embodiments, the present disclosure provides a consumable comprising a sweetening amount of rebaudioside R6-1. In some embodiments, the present disclosure provides a consumable comprising a sweetening amount of rebaudioside R6-2A. In some embodiments, the present disclosure provides a consumable comprising a sweetening amount of rebaudioside R6-2B. In some embodiments, the present disclosure provides a consumable comprising a sweetening amount of rebaudioside R6-4A. In some embodiments, the present disclosure provides a consumable comprising a sweetening amount of rebaudioside R6-4B. In some embodiments, the present disclosure provides a consumable comprising a sweetening amount of rebaudioside R7-2. The consumable can be, for example, a food product, a nutraceutical, a pharmaceutical, a dietary supplement, a dental hygienic composition, an edible gel composition, a cosmetic product and a tabletop flavoring.

As used herein, "dietary supplement(s)" refers to compounds intended to supplement the diet and provide nutrients, such as vitamins, minerals, fiber, fatty acids, amino acids, etc. that may be missing or may not be consumed in sufficient quantities in a diet. Any suitable dietary supplement known in the art may be used. Examples of suitable dietary supplements can be, for example, nutrients, vitamins, minerals, fiber, fatty acids, herbs, botanicals, amino acids, and metabolites.

As used herein, "nutraceutical(s)" refers to compounds, which includes any food or part of a food that may provide medicinal or health benefits, including the prevention and/or treatment of disease or disorder (e.g., fatigue, insomnia, effects of aging, memory loss, mood disorders, cardiovascular disease and high levels of cholesterol in the blood, diabetes, osteoporosis, inflammation, autoimmune disorders, etc.). Any suitable nutraceutical known in the art may be used. In some embodiments, nutraceuticals can be used as supplements to food and beverages and as pharmaceutical formulations for enteral or parenteral applications which may be solid formulations, such as capsules or tablets, or liquid formulations, such as solutions or suspensions.

In some embodiments, dietary supplements and nutraceuticals can further contain protective hydrocolloids (such as gums, proteins, modified starches), binders, film-forming agents, encapsulating agents/materials, wall/shell materials, matrix compounds, coatings, emulsifiers, surface active agents, solubilizing agents (oils, fats, waxes, lecithins, etc.), adsorbents, carriers, fillers, co-compounds, dispersing agents, wetting agents, processing aids (solvents), flowing agents, taste-masking agents, weighting agents, jellyfying agents, gel-forming agents, antioxidants and antimicrobials.

As used herein, a "gel" refers to a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives. Gels that can be eaten are referred to as "edible gel compositions." Edible gel compositions typically are eaten as snacks, as desserts, as a part of staple foods, or along with staple foods. Examples of suitable edible gel compositions can be, for example, gel desserts, puddings, jams, jellies, pastes, trifles, aspics, marshmallows, gummy candies, and the like. In some embodiments, edible gel mixes generally are powdered or granular solids to which a fluid may be added to form an edible gel composition. Examples of suitable fluids can be, for example, water, dairy fluids, dairy analogue fluids, juices, alcohol, alcoholic beverages, and combinations thereof. Examples of suitable dairy fluids can be, for example, milk, cultured milk, cream, fluid whey, and mixtures thereof. Examples of suitable dairy analogue fluids can be, for example, soy milk and non-dairy coffee whitener.

As used herein, the term "gelling ingredient" refers to any material that can form a colloidal system within a liquid medium. Examples of suitable gelling ingredients can be, for example, gelatin, alginate, carageenan, gum, pectin, konjac, agar, food acid, rennet, starch, starch derivatives, and combinations thereof. It is well known to those in the art that the amount of gelling ingredient used in an edible gel mix or an edible gel composition can vary considerably depending on a number of factors such as, for example, the particular gelling ingredient used, the particular fluid base used, and the desired properties of the gel.

Gel mixes and gel compositions of the present disclosure can be prepared by any suitable method known in the art. In some embodiments, edible gel mixes and edible gel compositions of the present disclosure can be prepared using other ingredients in addition to the gelling agent. Examples of other suitable ingredients can be, for example, a food acid, a salt of a food acid, a buffering system, a bulking agent, a sequestrant, a cross-linking agent, one or more flavors, one or more colors, and combinations thereof.

Pharmaceutical compositions are also provided comprising any one of the rebaudiosides provided herein. In certain embodiments, any one of the pharmaceutical compositions of the present disclosure can contain from about 5 ppm to about 100 ppm of rebaudioside R6-1, and one or more pharmaceutically acceptable excipients. In certain embodiments, any one of the pharmaceutical compositions of the present disclosure can contain from about 5 ppm to about 100 ppm of rebaudioside R6-2A, and one or more pharmaceutically acceptable excipients. In certain embodiments, any one of the pharmaceutical compositions of the present disclosure can contain from about 5 ppm to about 100 ppm of rebaudioside R6-2B, and one or more pharmaceutically acceptable excipients. In certain embodiments, any one of the pharmaceutical compositions of the present disclosure can contain from about 5 ppm to about 100 ppm of rebaudioside R6-4A, and one or more pharmaceutically acceptable excipients. In certain embodiments, any one of the pharmaceutical compositions of the present disclosure can contain from about 5 ppm to about 100 ppm of rebaudioside R6-4B, and one or more pharmaceutically acceptable excipients. In certain embodiments, any one of the pharmaceutical compositions of the present disclosure can contain from about 5 ppm to about 100 ppm of rebaudioside R7-2, and one or more pharmaceutically acceptable excipients. In some embodiments, any one of the pharmaceutical compositions of the present disclosure can be used to formulate pharmaceutical drugs containing one or more active agents that exert a biological effect. Accordingly, in some embodiments, any one of the pharmaceutical compositions of the present disclosure can contain one or more active agents that exert a biological effect. Suitable active agents are well known in the art (e.g., The Physician's Desk Reference). Such compositions can be prepared according to procedures well known in the art, for example, as described in Remington's Pharmaceutical Sciences, Mack Publishing Co., Easton, Pa., USA.

Rebaudioside R6-1, rebaudioside R6-2A, rebaudioside R6-2B, rebaudioside R6-4A, rebaudioside R6-4B, or rebaudioside R7-2 can be used with any suitable dental and oral hygiene compositions known in the art. Examples of suitable dental and oral hygiene compositions can be, for example, toothpastes, tooth polishes, dental floss, mouthwashes, mouth rinses, dentrifices, mouth sprays, mouth refreshers, plaque rinses, dental pain relievers, and the like. Dental and oral hygiene compositions comprising any one of the rebaudiosides provided herein are also provided.

Suitable amounts of rebaudioside R6-1, rebaudioside R6-2A, rebaudioside R6-2B, rebaudioside R6-4A, rebaudioside R6-4B, or rebaudioside R7-2 present in any one of the compositions provided herein, such as in the consumable can be, for example, from about 5 parts per million (ppm) to about 100 parts per million (ppm). In some embodiments of any one of the compositions provided, low concentrations of rebaudioside R6-1, rebaudioside R6-2A, rebaudioside R6-2B, rebaudioside R6-4A, rebaudioside R6-4B, or rebaudioside R7-2, for example, less than 100 ppm, has an equivalent sweetness to sucrose solutions having concentrations between 10,000 ppm to 30,000 ppm. The final concentration can range?ranges from about 5 ppm to about 100 ppm, from about 5 ppm to about 95 ppm, from about 5 ppm to about 90 ppm, from about 5 ppm to about 85 ppm, from about 5 ppm to about 80 ppm, from about 5 ppm to about 75 ppm, from about 5 ppm to about 70 ppm, from about 5 ppm to about 65 ppm, from about 5 ppm to about 60 ppm, from about 5 ppm to about 55 ppm, from about 5 ppm to about 50 ppm, from about 5 ppm to about 45 ppm, from about 5 ppm to about 40 ppm, from about 5 ppm to about 35 ppm, from about 5 ppm to about 30 ppm, from about 5 ppm to about 25 ppm, from about 5 ppm to about 20 ppm, from about 5 ppm to about 15 ppm, or from about 5 ppm to about 10 ppm. Alternatively, rebaudioside R6-1, rebaudioside R6-2A, rebaudioside R6-2B, rebaudioside R6-4A, rebaudioside R6-4B, or rebaudioside R7-2 can be present in any one of the compositions provided, such as in any one of the consumable products of the present disclosure, at a final concentration that ranges from about 5 ppm to about 100 ppm, from about 10 ppm to about 100 ppm, from about 15 ppm to about 100 ppm, from about 20 ppm to about 100 ppm, from about 25 ppm to about 100 ppm, from about 30 ppm to about 100 ppm, from about 35 ppm to about 100 ppm, from about 40 ppm to about 100 ppm, from about 45 ppm to about 100 ppm, from about 50 ppm to about 100 ppm, from about 55 ppm to about 100 ppm, from about 60 ppm to about 100 ppm, from about 65 ppm to about 100 ppm, from about 70 ppm to about 100 ppm, from about 75 ppm to about 100 ppm, from about 80 ppm to about 100 ppm, from about 85 ppm to about 100 ppm, from about 90 ppm to about 100 ppm, or from about 95 ppm to about 100 ppm.

In certain embodiments, from about 5 ppm to about 100 ppm of rebaudioside R6-1, rebaudioside R6-2A, rebaudioside R6-2B, rebaudioside R6-4A, rebaudioside R6-4B, or rebaudioside R7-2 is present in a food product compositions. Such compositions are also provided. As used herein, "food product composition(s)" refers to any solid or liquid ingestible material that can, but need not, have a nutritional value and be intended for consumption by humans and animals.

Examples of suitable food product compositions can be, for example, confectionary compositions, such as candies, mints, fruit flavored drops, cocoa products, chocolates, and the like; condiments, such as ketchup, mustard, mayonnaise, and the like; chewing gums; cereal compositions; baked goods, such as breads, cakes, pies, cookies, and the like; dairy products, such as milk, cheese, cream, ice cream, sour cream, yogurt, sherbet, and the like; tabletop sweetener compositions; soups; stews; convenience foods; meats, such as ham, bacon, sausages, jerky, and the like; gelatins and gelatin-like products such as jams, jellies, preserves, and the like; fruits; vegetables; egg products; icings; syrups including molasses; snacks; nut meats and nut products; and animal feed.

Food product compositions can also be herbs, spices and seasonings, natural and synthetic flavors, and flavor enhancers, such as monosodium glutamate. In some embodiments, any one of the food product compositions can be, for example, prepared packaged products, such as dietetic sweeteners, liquid sweeteners, granulated flavor mixes, pet foods, livestock feed, tobacco, and materials for baking applications, such as powdered baking mixes for the preparation of breads, cookies, cakes, pancakes, donuts and the like. In other embodiments, any one of the food product compositions can also be diet and low-calorie food and beverages containing little or no sucrose.

In certain embodiments that may or may not be combined with any one of the preceding embodiments, the rebaudioside R6-1, rebaudioside R6-2A, rebaudioside R6-2B, rebaudioside R6-4A, rebaudioside R6-4B, or rebaudioside R7-2 is the only sweetener, and the product has a sweetness intensity equivalent to about 1% to about 4% (w/v-%) sucrose solution. In certain embodiments that may or may not be combined with any one of the preceding embodiments, the consumable products and beverage products can further include an additional sweetener, where the product has a sweetness intensity equivalent to about 1% to about 10% (w/v-%) sucrose solution. In certain embodiments that may or may not be combined with any one of the preceding embodiments, every sweetening ingredient in the product is a high intensity sweetener. In certain embodiments that may or may not be combined with any one of the preceding embodiments, every sweetening ingredient in the product can a natural high intensity sweetener. In certain embodiments that may or may not be combined with any one of the preceding embodiments, the additional sweetener contains one or more sweeteners selected from a stevia extract, a steviol glycoside, stevioside, rebaudioside A, rebaudioside B, rebaudioside C, rebaudioside D, rebaudioside D2, rebaudioside F, rebaudioside D3, rebaudioside Z1, rebaudioside Z2, rebaudioside M, rebaudioside W, rebaudioside V, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside mogroside IV, siamenoside I, mogroside V, monatin, thaumatin, monellin, brazzein, L-alanine, glycine, Lo Han Guo, hernandulcin, phyllodulcin, trilobtain, and combinations thereof. In certain embodiments that may or may not be combined with any one of the preceding embodiments, the consumable products and beverage products can further include one or more additives selected from a carbohydrate, a polyol, an amino acid or salt thereof, a poly-amino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof. In certain embodiments that may or may not be combined with any one of the preceding embodiments, the rebaudioside R6-1, rebaudioside R6-2A, rebaudioside R6-2B, rebaudioside R6-4A, rebaudioside R6-4B, or rebaudioside R7-2 has a purity of about 50% to about 100% by weight before it is added into the product.

EXAMPLES

Example 1: Production of Novel Steviol Glycosides R6-2 and R7-2 by Enzymatic Bioconversion According to the current invention full-length DNA fragments of all candidate UDP-glucosyltransferase (UGT) genes were commercially synthesized. Almost all codons of the cDNA were changed to those preferred for *E. coli* (Genscript, NJ). The synthesized DNA was cloned into a bacterial expression vector pETite N-His SUMO Kan Vector (Lucigen).

Each expression construct was transformed into *E. coli* BL21 (DE3), which was subsequently grown in LB media containing 50 μg/mL kanamycin at 37° C. until reaching an OD600 of 0.8-1.0. Protein expression was induced by addition of 1 mM isopropyl β-D-1-thiogalactopyranoside (IPTG) and the culture was further grown at 16° C. for 22 hr. Cells were harvested by centrifugation (3,000×g; 10 min; 4° C.). The cell pellets were collected and were either used immediately or stored at −80° C.

The cell pellets typically were re-suspended in lysis buffer (50 mM potassium phosphate buffer, pH 7.2, 25 ug/ml lysozyme, 5 ug/ml DNase I, 20 mM imidazole, 500 mM NaCl, 10% glycerol, and 0.4% Triton X-100). The cells were disrupted by sonication under 4° C., and the cell debris was clarified by centrifugation (18,000×g; 30 min). Supernatant was loaded to an equilibrated (equilibration buffer: 50 mM potassium phosphate buffer, pH 7.2, 20 mM imidazole, 500 mM NaCl, 10% glycerol) Ni-NTA (Qiagen) affinity column. After loading of protein sample, the column was washed with equilibration buffer to remove unbound contaminant proteins. The His-tagged UGT recombinant polypeptides were eluted by equilibration buffer containing 250 mM imidazole.

The purified candidate UGTs recombinant polypeptides were assayed for glycosylation activity by using rebaudioside D3 (Reb D3) as substrate. Typically, the recombinant polypeptide (10-50 μg) was tested in a 200 μl in vitro reaction system. The reaction system contained 50 mM potassium phosphate buffer, pH 7.2, 3 mM $MgCl_2$, 1 mg/ml Reb D3 substrate, 1 mM UDP-glucose or UDP and/or sucrose synthase (SUS) and 250 mM sucrose. The reaction was performed at 30-37° C. and 50 ul reaction was terminated by adding 200 μL 1-butanol at various time points. The samples were extracted three times with 200 μL 1-butanol. The pooled fraction was dried and dissolved in 100 μL 80% methanol for high-performance liquid chromatography (HPLC) analysis.

HPLC analysis was then performed using a Dionex UPLC ultimate 3000 system (Sunnyvale, CA), including a quaternary pump, a temperature-controlled column compartment, an auto sampler and a UV absorbance detector. A Synergi Hydro-RP column (Phenomenex) with guard column was used for the characterization of steviol glycosides in the pooled samples. Acetonitrile in water was used for isocratic elution in the HPLC analysis. The detection wavelength used in the HPLC analysis was 210 nm.

After activity screening, it was found that UGT76G1 (SEQ ID NO: 1) has strong activity to produce R6-2 and R7-2 steviol glycosides (FIG. 2).

Figure 3:
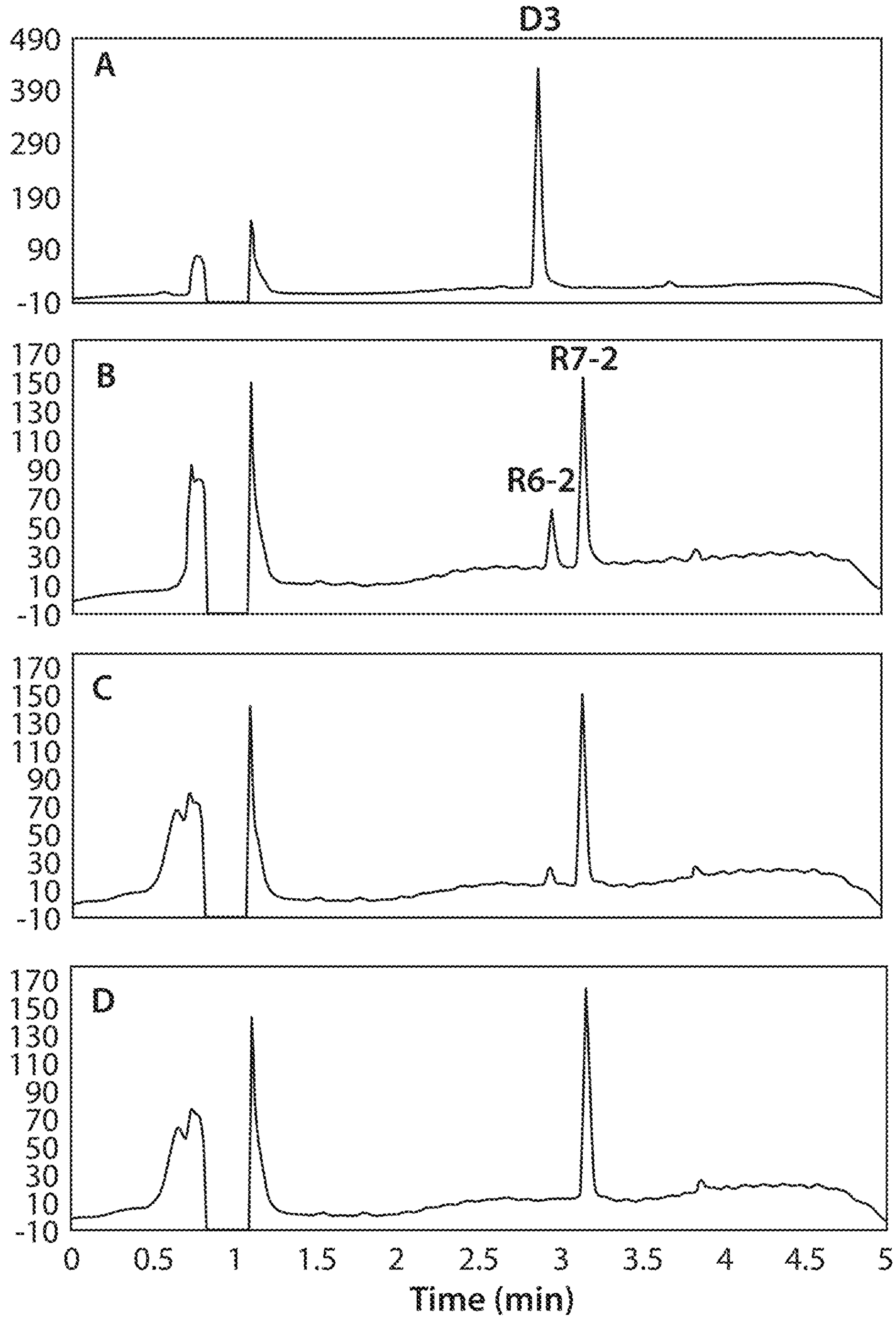
FIG. 3. UGT76G1 catalysis reaction to produce R6-2 and R7-2 from Reb D3. Panel A shows the HPLC retention time of rebaudioside D3 ("D3") standard. Panels B-D show R6-2 and R7-2 enzymatically produced by UGT76G1 at 2 hours (Panel B), 4 hours (Panel C) and 19 hours (Panel D).

As shown in FIG. 3, UGT76G1 can convert Reb D3 to R6-2 and the produced R6-2 can be converted to R7-2 continentally. R6-2 and R7-2 was produced at early reaction time (2 hr, FIG. 3, Panel B). The produced R6-2 can be converted to R7-2 at later time points (4 hr, FIG. 3, Panel C). Eventually, all Reb D3 and produced R6-2 can be fully converted to R7-2 compound (19 hr, FIG. 3, Panel D).

Example 2: Identification of R6-2 and R7-2 Production Via LC-MS Analysis

In order to confirm the produced compounds, the produced compound were analyzed by LC-MS analysis comparing to standards and confirmed their identities.

Same samples from above enzymatic bioconversion were analyzed by LC-MS using the Synergy Hydro-RP column Mobile phase A was 0.1% formic acid in water, and mobile phase B was 0.1% formic acid in acetonitrile. The flow rate was 0.6 ml/minute. Mass spectrometry analysis of the samples was done on the Q Exactive Hybrid Quadrupole-Orbitrap Mass Spectrometer (Thermo Fisher Scientific) with an optimized method in positive ion mode.

Figure 4:
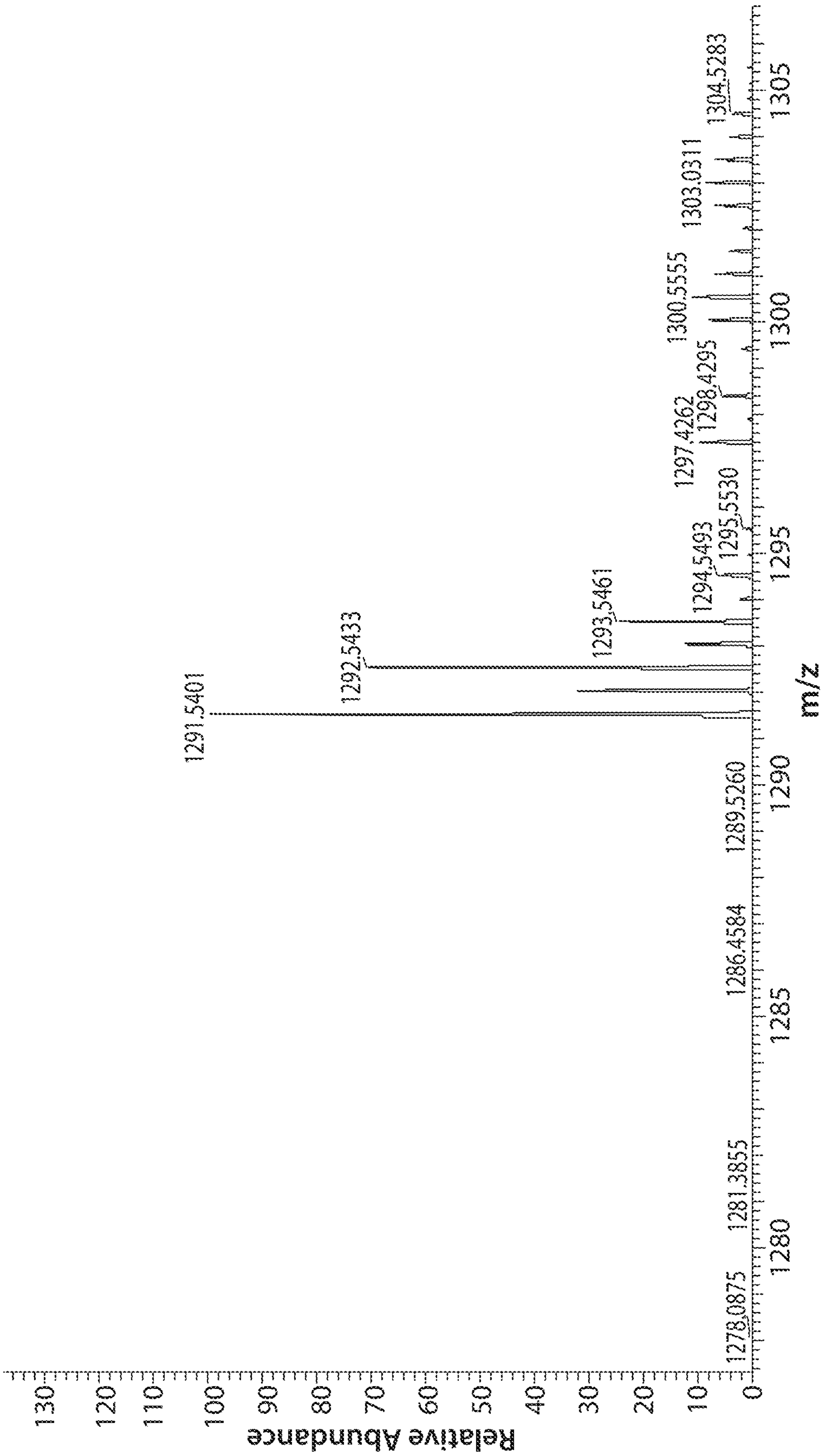
FIG. 4. LC MS analysis of the produced R6-2 compound.

The molecular formula of compound R6-2 has been deduced as $C_{56}H_{90}O_{33}$ on the basis of its positive high resolution (HR) mass spectrum which showed adducts ions corresponding to $[M+H]^+$ at m/z 1291.5401 (FIG. 4). The predicted structure of R6-2 is presented in FIG. 2.

Figure 5:
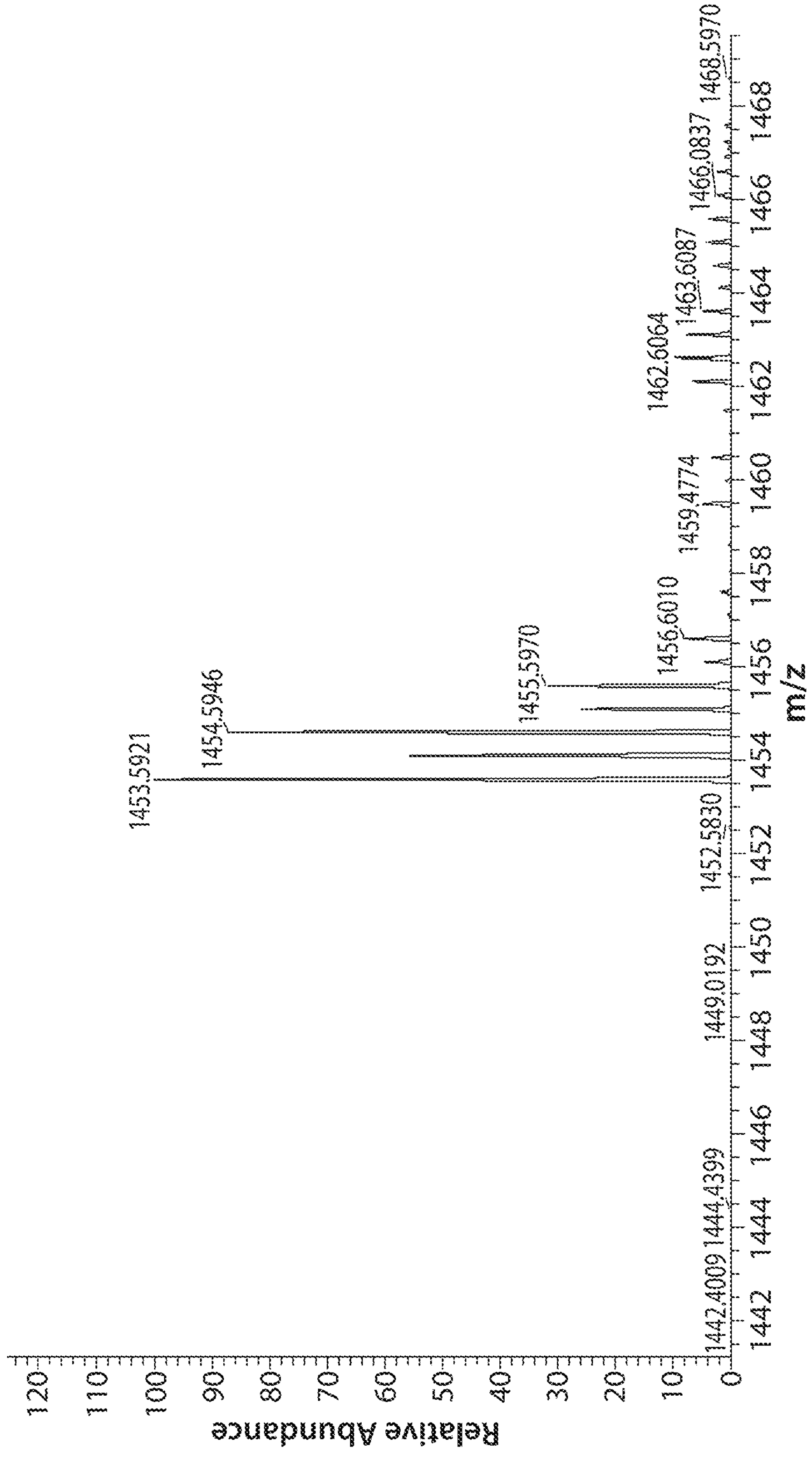
FIG. 5. LC MS analysis of produced R7-2 compound.

The molecular formula of compound R7-2 has been deduced as $C_{62}H_{100}O_{38}$ on the basis of its positive high resolution (HR) mass spectrum which showed adducts ions corresponding to $[M+H]^+$ at m/z 1453.5921 (FIG. 5). The predicted structure of R7-2 is presented in FIGS. 2, 6 and 7.

Example 3: The Structure of R7-2 was Analyzed by NMR

The produced R7-2 compound was purified by semi preparative chromatography as described above.

HRMS data were generated with a LTQ Orbitrap Discovery HRMS instrument, with its resolution set to 30 k. Scanned data from m/z 150 to 1500 in positive ion electrospray mode. The needle voltage was set to 4 kV; the other source conditions were sheath gas=25, aux gas=0, sweep gas=5 (all gas flows in arbitrary units), capillary voltage=30V, capillary temperature=300° C., and tube lens voltage=75. Sample was diluted with pyridine and injected 50 microliters.

NMR spectra were acquired on Bruker Avance DRX 500 MHz or Varian INOVA 600 MHz instrument instruments using standard pulse sequences. The 1D ($^1H$ and $^{13}C$) and 2D (TOCSY, HSQC, ROESY, and HMBC) NMR spectra were performed in $C_5D_5N$.

The molecular formula of compound R7-2 has been deduced as $C_{62}H_{100}O_{38}$ on the basis of its positive high resolution (HR) mass spectrum which showed adducts ions corresponding to $[M+NH_4]^+$ at m/z 1470.6222 and $[M+Na]^+$ at m/z 1475.5774; this composition was supported by $^{13}C$ NMR, and HSQC spectral data. The $^1H$ NMR spectrum of R7-2 showed the presence of two sp3 methyl singlets at δ 1.33 and 1.39; two olefinic protons as singlets at δ 5.00 and 5.74 of an exocyclic double bond; nine sp3 methylene and two sp3 methine protons between δ 0.75-2.74 characteristic for the ent-kaurane diterpenoids isolated earlier from the genus *Stevia*. Enzymatic hydrolysis of R7-2 furnished a compound which was found identical to steviol based on NMR spectral data (Ohtani et al, 1992). The $^1H$ NMR spectrum of R7-2 also showed the presence of anomeric protons resonating at δ 4.99, 5.05, 5.35, 5.38, 5.43, 5.82, and 6.40 suggesting seven sugar units in its molecular structure. Acid hydrolysis of R7-2 with 5% $H_2SO_4$ afforded D-glucose which was identified by direct comparison with authentic sample by TLC suggested the presence of six glucopyranosyl moieties in its molecular structure (Bedir et al., 2001; Chaturvedula et al., 2003; and Huan et al., 1998). Further, configuration of D-glucose was identified by preparing its corresponding thiocarbamoyl-thiazolidine carboxylate derivative with L-cysteine methyl ester and O-tolyl isothiocyanate, and in comparison, of its retention time with the standard sugars as described in the literature comparison (Tanaka et al., 2007). Based on the results from NMR spectral data of R7-2, it was concluded that there are seven D-glucosyl units in its structure attached to the steviol moiety. The basic skeleton of steviol in R7-2 was supported by TOCSY (H-1/H-2; H-2/H-3; H-5/H-6; H-6/H-7; H-9/H-11; H-11/H-12) and HMBC (H-1/C-2, C-10; H-3/C-1, C-2, C-4, C-5, C-18, C-19; H-5/C-4, C-6, C-7, C-9, C-10, C-18, C-19, C-20; H-9/C-8, C-10, C-11, C-12, C-14, C-15; H-14/C-8, C-9, C-13, C-15, C-16 and H-17/C-13, C-15, C-16) correlations.

The $^1H$ and $^{13}C$ NMR values for all protons and carbons in R7-2 were assigned on the basis of TOCSY, HMQC and HMBC correlations and are given in Table 1.

Figure 8:
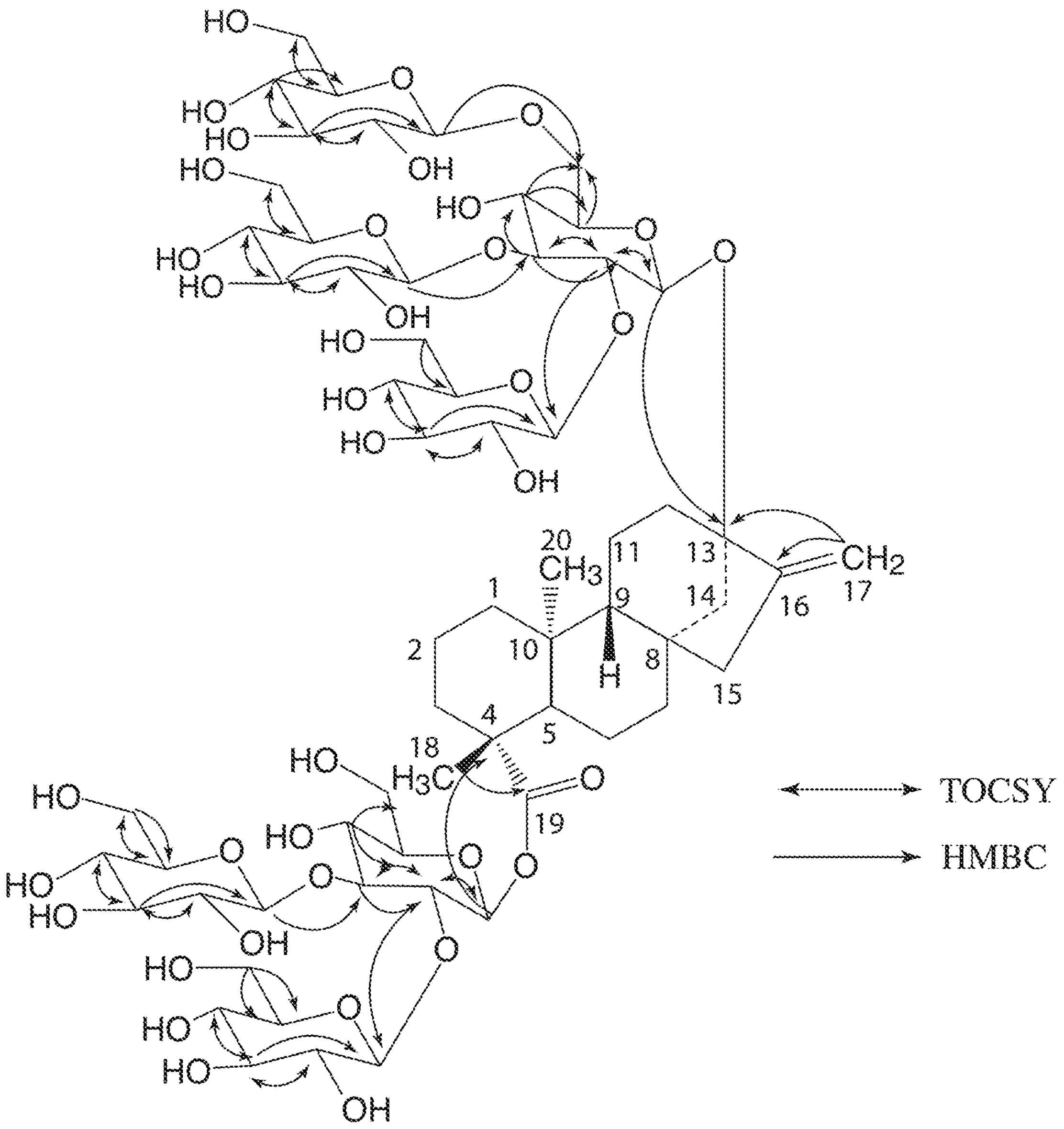
FIG. 8. Key TOCSY and HMBC correlations of R7-2.

A close comparison of the $^1H$ and $^{13}C$ NMR spectrum of R7-2 with rebaudioside D3 (Mao et al. 2017) suggested that this compound is also a steviol glycoside with four glucosyl moieties attached at the C-13 hydroxyl of which three are attached in the form of an ether as a 2,3-branched glucotriosyl substituent; and another 2,3-branched glucotriosyl moiety at C-19 as an ester. The above data accounted for six glucosyl units in the molecular structure of R7-2 leaving an identification of the additional glucosyl moiety on the 2,3-branched glucotriosyl substituent at C-13 position. Based on the key TOCSY and HMBC correlations shown in FIG. 8, the placement of the seventh glucosyl moiety has been assigned at C-6 position of Sugar II as in rebaudioside D3.

The large coupling constants observed for all the seven anomeric protons of the glucosyl moieties at δ 4.99 (d, J=7.6 Hz), 5.05 (d, J=7.4 Hz), 5.35 (d, J=8.1 Hz), 5.38 (d, J=7.7 Hz), 5.43 (d, J=7.7 Hz), 5.82 (d, J=6.6 Hz), and 6.40 (d, J=8.1 Hz), suggested their (3-orientation as reported for steviol glycosides.

Based on the NMR and HR mass spectral data as well as hydrolysis studies, structure of R7-2 produced by the enzymatic conversion of Rebaudioside D3 was deduced as 13-[(2-O-β-D-glucopyranosyl-3-O-β-D-glucopyranosyl-6-O-β-D-glucopyranosyl-β-D-glucopyranosyl)oxy] ent-kaur- 16-en-19-oic acid-R2-O-β-D-glucopyranosyl-3-O-β-D-glucopyranosyl-β-D-glucopyranosyl)ester.

R7-2 (500 μg) was dissolved in 5.0 ml of 0.1 M sodium acetate buffer by maintaining pH at 4.5 and 100 uL of crude pectinase from *Aspergillus niger* (Sigma-Aldrich) was added. The mixture was stirred at 50° C. for 96 hr and the product precipitated out during the reaction was filtered and then solidified. The resulting product obtained was identified as steviol by comparison of their $^1$H NMR spectral data.

R7-2 (1 mg) is dissolved in MeOH (8 ml) and added 5% $H_2SO_4$ (25 mL). The mixture was refluxed for 16 hours, cooled to room temperature and then neutralized with saturated sodium carbonate. The aqueous phase was extracted with ethyl acetate (EtOAc, 2×25 ml) and the aqueous layer was concentrated and compared with standard sugars using the TLC system EtOAc/n-butanol/water (2:7:1) and $CH_2Cl_2$/MeOH/water (10:6:1) (Bedir et al., 2001; Chaturvedula et al., 2003; Huan et al., 1998); the sugars in R7-2 were identified as D-glucose.

R7-2 (1 mg) was hydrolyzed with 0.5 M HCl (1.5 mL) for 1.5 h. After cooling, the mixture was passed through an Amberlite IRA400 column and the eluate was lyophilized. The residue was dissolved in pyridine (0.75 mL) and heated with L-cysteine methyl ester HCl (7.5 mg) at 60° C. for 1.5 h, and then O-tolyl isothiocyanate (30 uL) was added to the mixture and heated at 60° C. for an additional 1.5 h. HPLC analysis of the reaction mixture was performed by a Phenomenex Luna column [C18, 150×4.6 mm (5 u)] using the mobile phase 25% acetonitrile-0.2% TFA water, 1 mL/min under UV detection at 250 nm. The sugar was identified as D-glucose (tR, 12.72) [authentic samples, D-glucose (tR, 12.64) and L-glucose (tR, 11.48 min)] (Tanaka et al., 2007).

Figure 6:
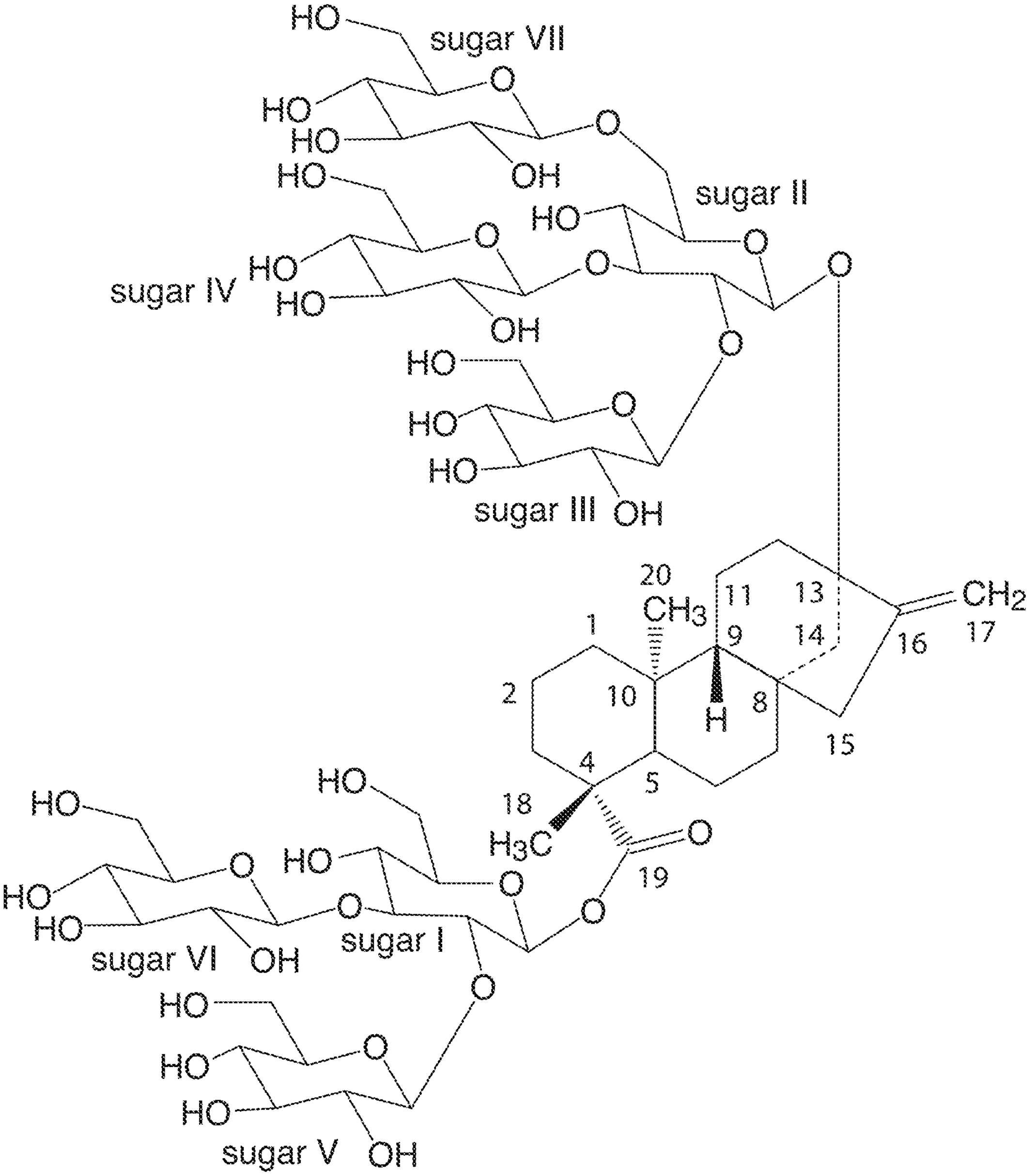
FIG. 6. The structure of R7-2.
Figure 7A:
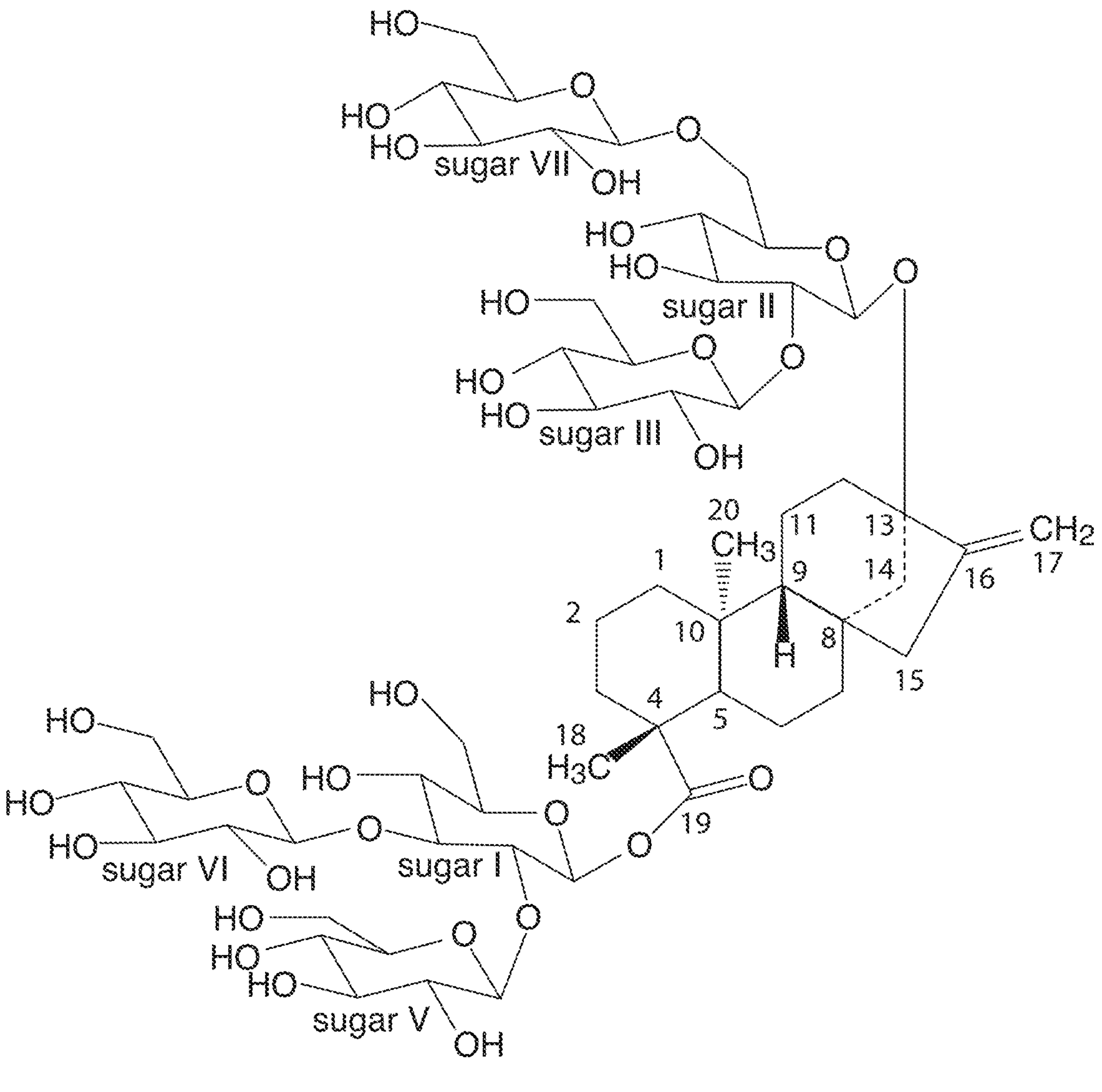
FIGS. 7A and 7B. The structures of R6-2A (FIG. 7A) and R6-2B (FIG. 7B).
Figure 7B:
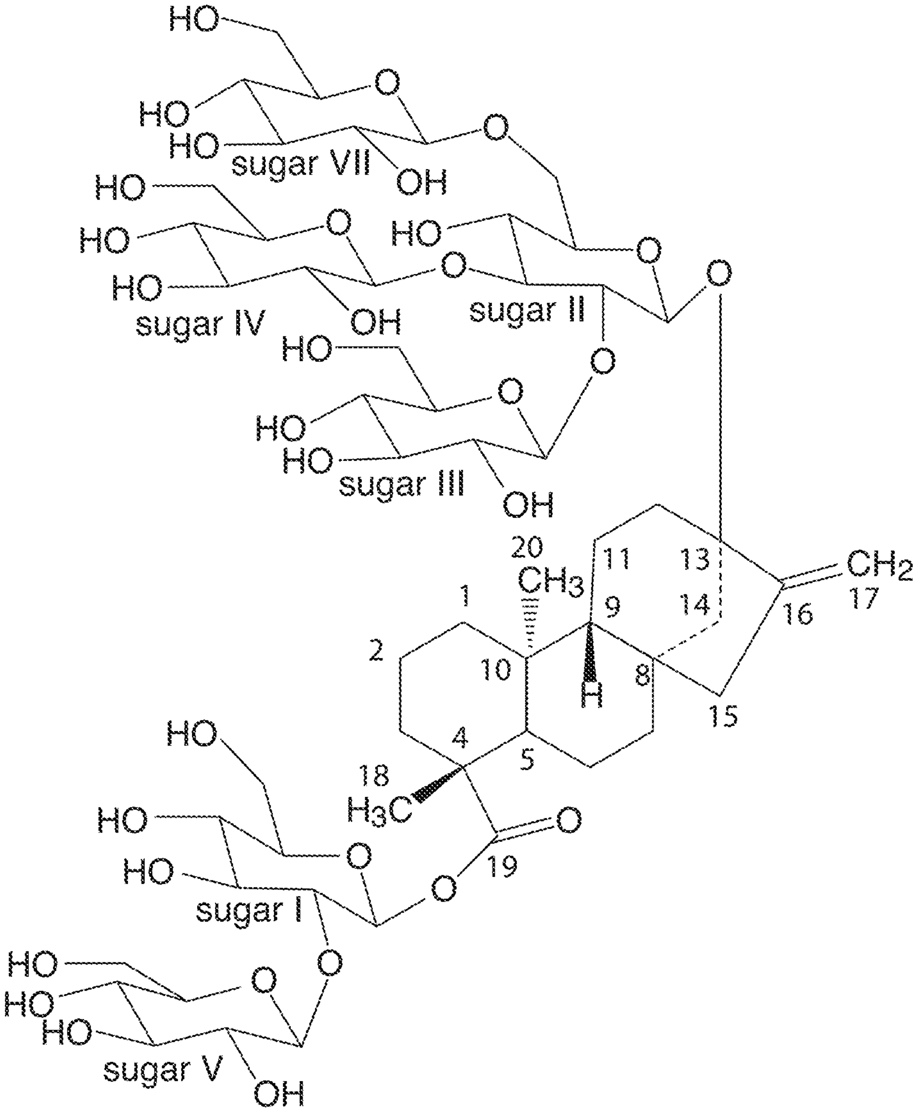

A compound named R7-2 was obtained from enzymatic bioconversion of rebaudioside D3. The structure elucidation, and complete NMR spectral assignments ($^1$H and $^{13}$C) for R7-2 were made on the basis of extensive 1D and 2D NMR as well as high resolution mass spectral data and hydrolysis studies, which suggested the structure as 13-[(2-O-β-D-glucopyranosyl-3-O-β-D-glucopyranosyl-6-O-β-D-glucopyranosyl-β-D-glucopyranosyl)oxy] ent-kaur-16-en-19-oic acid-R2-O-β-D-glucopyranosyl-3-O-β-D-glucopyranosyl glucopyranosyl)ester (FIG. 6).

Example 5: Production of Novel Steviol Glycoside R6-1 by Enzymatic Bioconversion Full-length DNA fragments of all candidate UDP-glucosyltransferase (UGT) genes were commercially synthesized. Almost all codons of the cDNA were changed to those preferred for *E. coli* (Genscript, NJ). The synthesized DNA was cloned into a bacterial expression vector pETite N-His SUMO Kan Vector (Lucigen).

Each expression construct was transformed into *E. coli* BL21 (DE3), which was subsequently grown in LB media containing 50 μg/mL kanamycin at 37° C. until reaching an $OD_{600}$ of 0.8-1.0. Protein expression was induced by addition of 1 mM isopropyl β-D-1-thiogalactopyranoside (IPTG) and the culture was further grown at 16° C. for 22 hr. Cells were harvested by centrifugation (3,000×g; 10 min; 4° C.). The cell pellets were collected and were either used immediately or stored at −80° C.

The cell pellets typically were re-suspended in lysis buffer (50 mM potassium phosphate buffer, pH 7.2, 25 ug/ml lysozyme, 5 ug/ml DNase I, 20 mM imidazole, 500 mM NaCl, 10% glycerol, and 0.4% Triton X-100). The cells were disrupted by sonication under 4° C., and the cell debris was clarified by centrifugation (18,000×g; 30 min). Supernatant was loaded to an equilibrated (equilibration buffer: 50 mM potassium phosphate buffer, pH 7.2, 20 mM imidazole, 500 mM NaCl, 10% glycerol) Ni-NTA (Qiagen) affinity column. After loading of protein sample, the column was washed with equilibration buffer to remove unbound contaminant proteins. The His-tagged UGT recombinant polypeptides were eluted by equilibration buffer containing 250 mM imidazole.

The purified candidate UGTs recombinant polypeptides were assayed for glycosylation activity by using rebaudioside D (Reb D) as substrate. Typically, the recombinant polypeptide (50-100 μg) was tested in a 200 μl in vitro reaction system. The reaction system contained 50 mM potassium phosphate buffer, pH 7.2, 3 mM $MgCl_2$, 0.5 mg/ml Reb D substrate, 1 mM UDP-glucose or UDP and/or sucrose synthase (SUS) and 250 mM sucrose. The reaction was performed at 30-37° C. and 50 ul reaction was terminated by adding 200 μL 1-butanol at various time points. The samples were extracted three times with 200 μL 1-butanol. The pooled fraction was dried and dissolved in 100 μL 80% methanol for high-performance liquid chromatography (HPLC) analysis.

HPLC analysis was then performed using a Dionex UPLC ultimate 3000 system (Sunnyvale, CA), including a quaternary pump, a temperature-controlled column compartment, an auto sampler and a UV absorbance detector. A Synergi Hydro-RP column (Phenomenex) with guard column was used for the characterization of steviol glycosides in the pooled samples. Mobile phase A is water, and mobile phase B is acetonitrile. The detection wavelength used in the HPLC analysis was 210 nm.

Figure 10:
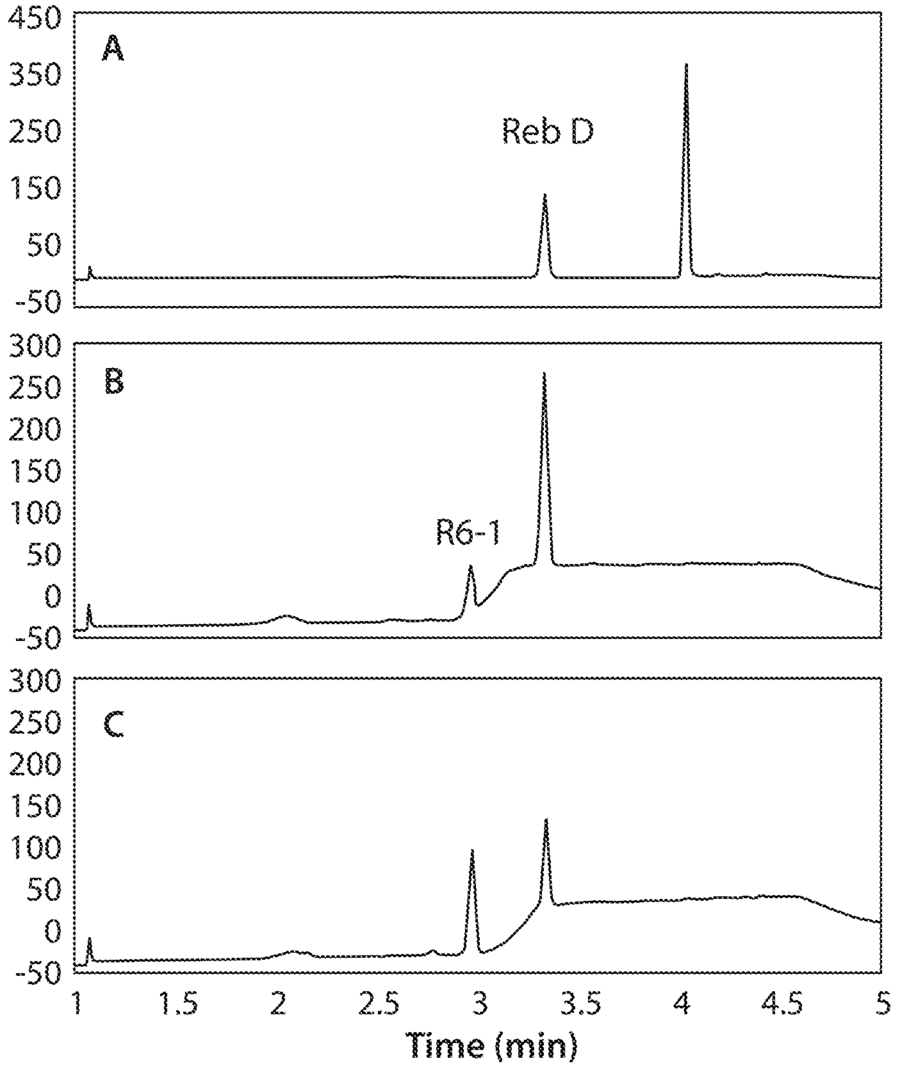
FIG. 10. HV1 catalysis reaction to produce R6-1 from Reb D. Panel A shows the HPLC retention time of rebaudioside D ("Reb D") standard. Panels B and C show R6-1 enzymatically produced by HV1 at 6 hours (Panel B) and 24 hours (Panel C).

After activity screening, HV1 (SEQ ID NO: 3) was found to have strong activity to produce R6-1 steviol glycoside (FIG. 9). As shown in FIG. 10, HV1 can convert Reb D to R6-1. More R6-1 can be produced after longer reaction time (24 hr, FIG. 10, Panel C).

Example 6: Identification of R6-1 Production by LC-MS Analysis

In order to confirm the produced compounds, the produced compound was analyzed by LC-MS analysis comparing to standards and their identities confirmed.

Same samples from above enzymatical bioconversion were analyzed by LC-MS using the Synergy Hydro-RP column Mobile phase A was 0.1% formic acid in water, and mobile phase B was 0.1% formic acid in acetonitrile. The flow rate was 0.6 ml/minute. Mass spectrometry analysis of the samples was done on the Q Exactive Hybrid Quadrupole-Orbitrap Mass Spectrometer (Thermo Fisher Scientific) with an optimized method in positive ion mode.

Figure 11:
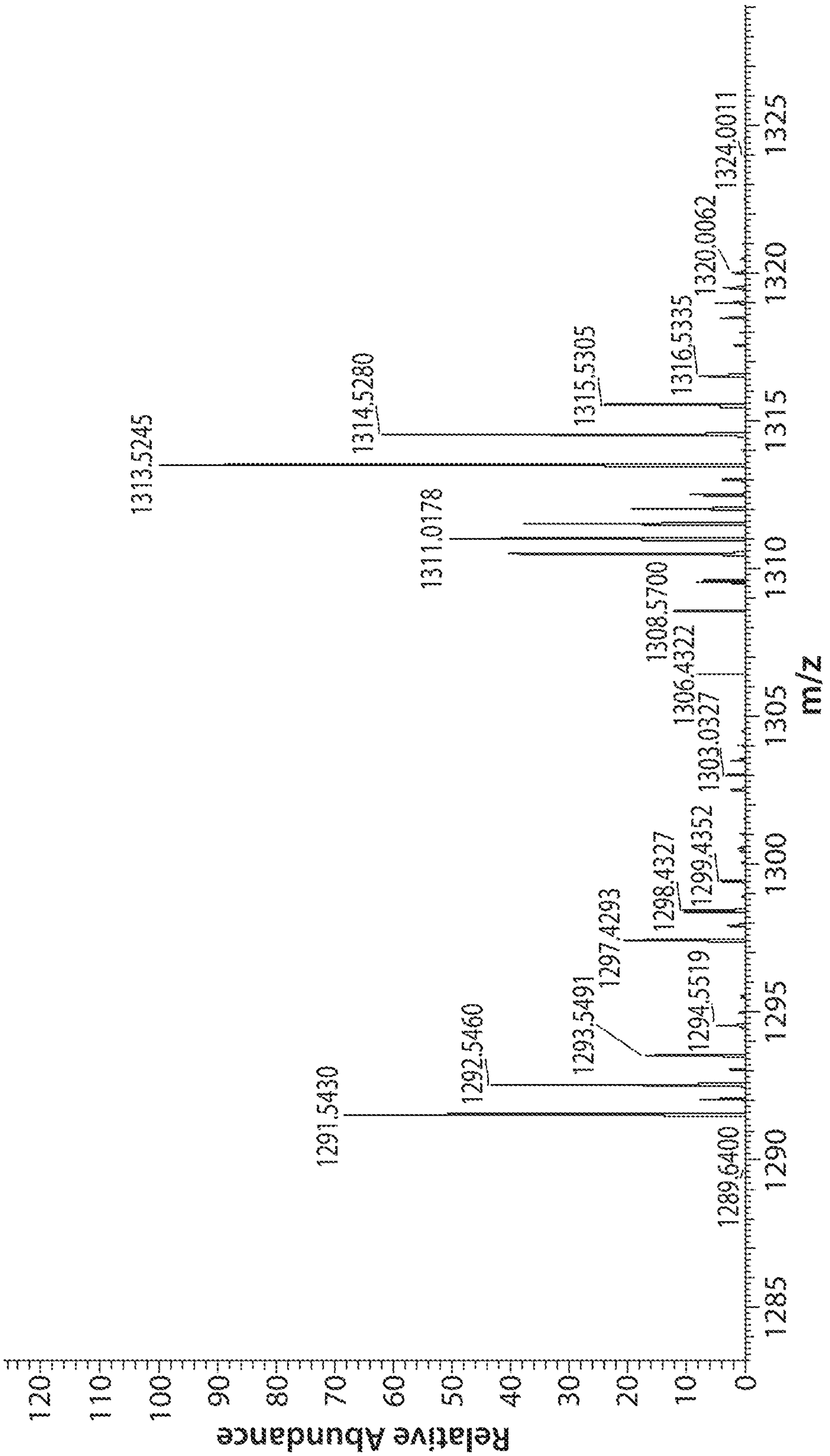
FIG. 11. LC MS analysis of the produced R6-1 compound.

The molecular formula of compound R6-1 has been deduced as $C_{56}H_{90}O_{33}$ on the basis of its positive high resolution (HR) mass spectrum which showed adducts ions corresponding to $[M+M]^+$ at m/z 1291.5430 and $[M+Na]^+$ at m/z 1313.5245 (FIG. 11). The predicted structure of R6-1 is presented in FIG. 9 and FIG. 12.

Example 7: The Structure of R6-1 was Analyzed by NMR

The produced R6-1 compound was purified by semi preparative chromatography as described above.

High resolution mass spectral data were generated with a LTQ Orbitrap Discovery HRMS instrument, with its resolution set to 30 k. Scanned data from m/z 150 to 1500 in positive ion electrospray mode. The needle voltage was set to 4 kV; the other source conditions were sheath gas=25, aux gas=0, sweep gas=5 (all gas flows in arbitrary units), capillary voltage=30V, capillary temperature=300° C., and tube lens voltage=75. Sample was diluted with pyridine and injected 50 microliters.

NMR spectra were acquired on Bruker Avance DRX 500 MHz or Varian INOVA 600 MHz instrument using standard pulse sequences. The 1D ($^1H$ and $^{13}C$) and 2D (TOCSY, HSQC, ROESY, and HMBC) NMR spectra were performed in $C_5D_5N$.

The molecular formula of R6-1 has been deduced as $C_{56}H_{90}O_{33}$ on the basis of its positive high resolution (HR) mass spectrum which showed adducts at m/z 1308.5693 and 1313.5236 corresponding to $[M+NH_4]^+$ and $[M+Na]^+$ ions respectively; this composition was supported by $^{13}C$ NMR spectral data. The $^1H$ NMR spectrum of R6-1 showed the presence of two sp3 methyl singlets at δ 1.12 and 1.48, two olefinic protons as singlets at δ 5.01 and 5.64 of an exocyclic double bond, nine sp3 methylene and two sp3 methine protons between δ 0.74-2.87 characteristic for the ent-kaurane diterpenoids isolated earlier from the genus *Stevia*. The basic skeleton of ent-kaurane diterpenoids was supported by TOCSY (H-1/H-2; H-2/H-3; H-5/H-6; H-6/H-7; H-9/H-11; H-11/H-12) and HMBC (H-1/C-2, C-10; H-3/C-1, C-2, C-4, C-5, C-18, C-19; H-5/C-4, C-6, C-7, C-9, C-10, C-18, C-19, C-20; H-9/C-8, C-10, C-11, C-12, C-14, C-15; H-14/C-8, C-9, C-13, C-15, C-16 and H-17/C-13, C-15, C-16) correlations.

Figure 13:
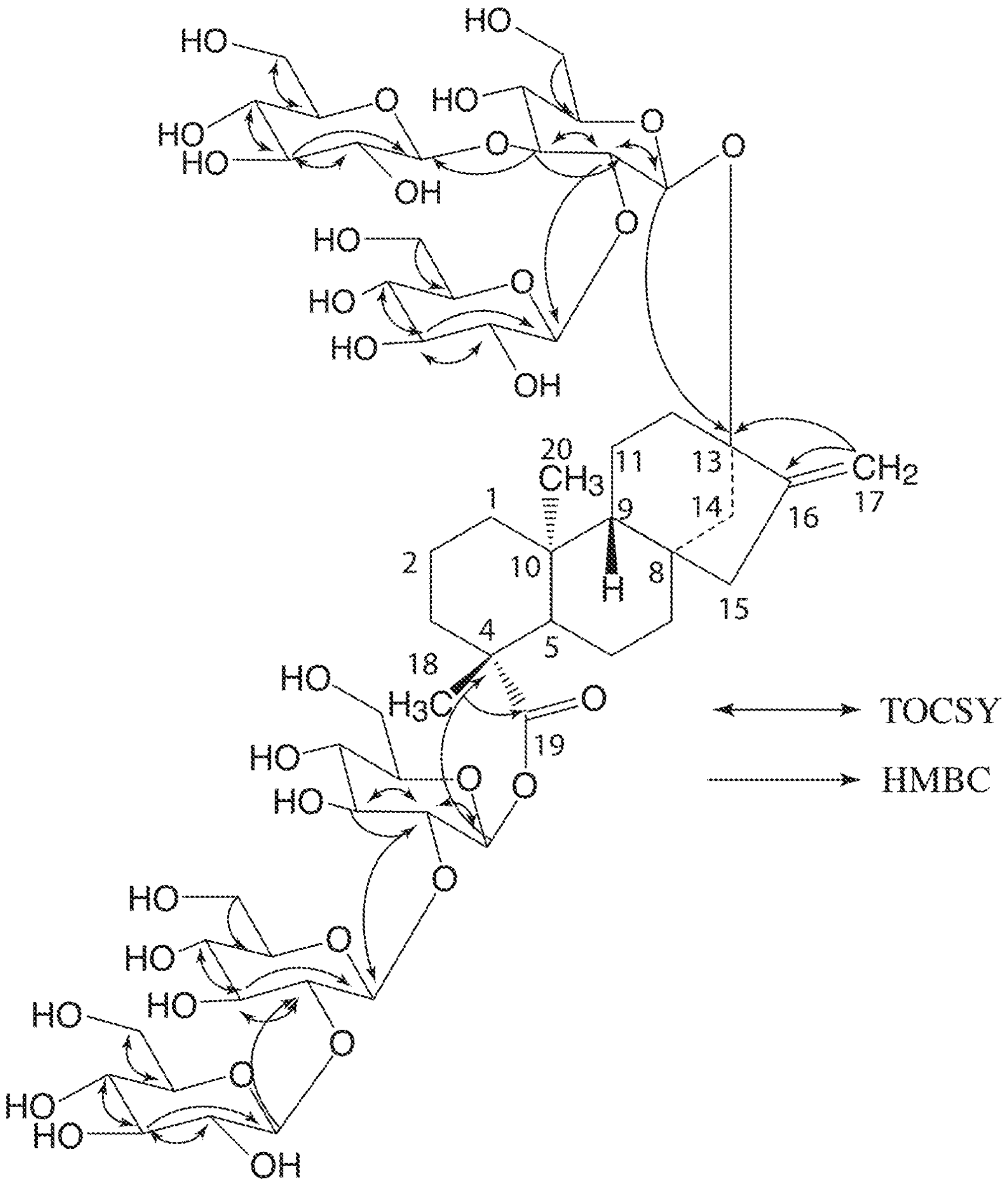
FIG. 13. Key TOCSY and HMBC correlations of R6-1.

Acid hydrolysis of R6-1 with 5% $H_2SO_4$ afforded D-glucose which was identified by direct comparison with authentic sample by TLC suggested the presence of six glucopyranosyl moieties in its molecular structure (Bedir et al., 2001; Chaturvedula et al., 2003; and Huan et al., 1998). Enzymatic hydrolysis of R6-1 furnished a compound which was found identical to steviol based on NMR spectral data (Ohtani et al, 1992). The configuration of D-glucose was identified by preparing its corresponding thiocarbamoyl-thiazolidine carboxylate derivative with L-cysteine methyl ester and O-tolyl isothiocyanate, and in comparison, of its retention time with the standard sugars as described in the literature comparison (Tanaka et al., 2007). Based on the results from NMR spectral data of R6-1, it was concluded that there are six glucosyl units in its structure which was supported by the $^1H$ NMR spectrum of R6-1 that showed the presence of anomeric protons resonating at δ 5.04, 5.05, 5.24, 5.37, 5.57, and 6.36; suggesting six sugar units in its molecular structure. A close comparison of the $^1H$ and $^{13}C$ NMR spectrum with rebaudioside D suggested that compound R6-1 is also a steviol glycoside which has three glucose residues that are attached at the C-13 hydroxyl as a 2,3-branched glucotriosyl substituent as an ether and 2-substituted glucobiosyl moiety at C-19 as an ester leaving the assignment of the additional glucosyl moiety. The key TOCSY and HMBC correlations shown in FIG. 13 suggested the placement of the sixth glucosyl moiety at C-2 position of Sugar V.

The large coupling constants observed for the six anomeric protons of the glucose moieties at δ 5.04 (d, J=7.6 Hz), 5.05 (d, J=7.4 Hz), 5.24 (d, J=7.6 Hz), 5.37 (d, J=7.4 Hz), 5.57 (d, J=7.7 Hz) and 6.36 (d, J=7.6 Hz), suggested their β-orientation as reported for steviol glycosides.

The $^1H$ and $^{13}C$ NMR values for all protons and carbons in R6-1 were assigned on the basis of TOCSY, HMQC and HMBC correlations and are given in Table 2.

Figure 12:
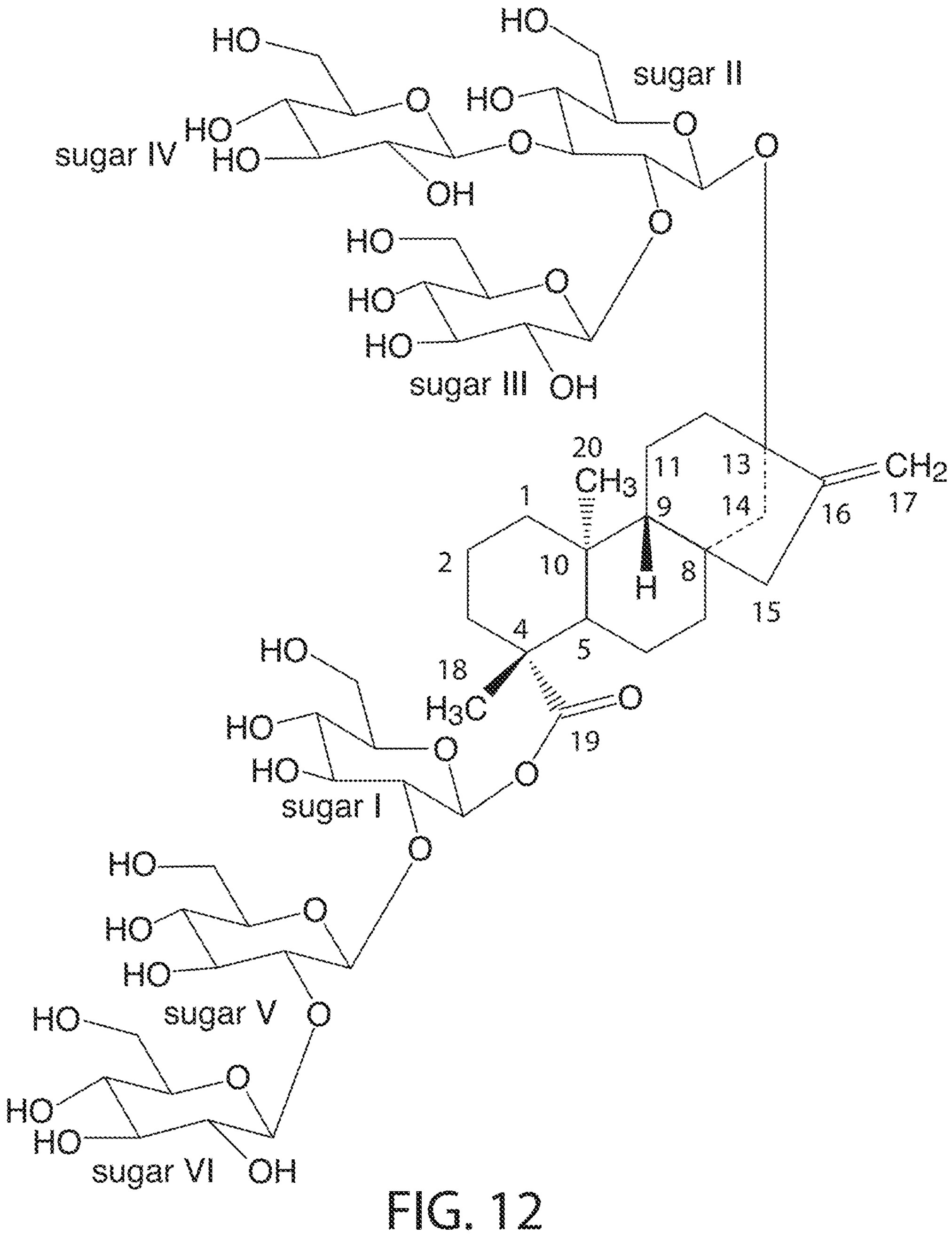
FIG. 12. The structure of R6-1.

Based on the results of NMR and HR mass spectral data as well as hydrolysis studies, the structure of R6-1 produced by the enzymatic conversion of rebaudioside D was deduced as 13-[(2-O-β-D-glucopyranosyl-3-O-β-D-glucopyranosyl-β-D-glucopyranosyl)oxy]ent-kaur-16-en-19-oic acid-[(2-O-{2-O-β-D-glucopyranosyl}-β-D-glucopyranosyl-β-D-glucopyranosyl)ester (FIG. 12).

R6-1 (250 μg) was dissolved in 2.5 ml of 0.1 M sodium acetate buffer by maintaining pH at 4.5 and 50 μL of crude pectinase from *Aspergillus niger* (Sigma-Aldrich) was added. The mixture was stirred at 50° C. for 48 hr and the product precipitated out during the reaction was filtered and then crystallized. The resulting product obtained was identified as steviol by comparison of their $^1H$ NMR spectral data (Ohtani et al., 1992).

R6-1 (500 μg) is dissolved in MeOH (3 ml) and added 5% $H_2SO_4$ (10 mL). The mixture was refluxed for 16 hours, cooled to room temperature and then neutralized with saturated sodium carbonate. The aqueous phase was extracted with ethyl acetate (EtOAc, 2×15 ml) and the aqueous layer was concentrated and compared with standard sugars using the TLC system EtOAc/n-butanol/water (2:7:1) and $CH_2Cl_2$/MeOH/water (10:6:1) (Bedir et al., 2001; Chaturvedula et al., 2003; Huan et al., 1998); the sugars in R6-1 were identified as D-glucose.

R6-1 (500 μg) was hydrolyzed with 0.5 M HCl (0.5 mL) for 1.5 h. After cooling, the mixture was passed through an Amberlite IRA400 column and the eluate was lyophilized. The residue was dissolved in pyridine (0.25 mL) and heated with L-cysteine methyl ester HCl (2.5 mg) at 60° C. for 1.5 h, and then O-tolyl isothiocyanate (12.5 uL) was added to the mixture and heated at 60° C. for an additional 1.5 h. HPLC analysis of the reaction mixture was performed by a Phenomenex Luna column [C18, 150×4.6 mm (5 u)] using the mobile phase 25% acetonitrile-0.2% TFA water, 1 mL/min under UV detection at 250 nm. The sugar was identified as D-glucose (tR, 12.64) [authentic samples, D-glucose (tR, 12.54) and L-glucose (tR, 11.42 min)] (Tanaka et al., 2007).

The complete $^1H$ and $^{13}C$ NMR spectral assignments for R6-1 were made on the basis of extensive 1D and 2D NMR as well as high resolution mass spectral data and hydrolysis, which suggested the structure as 13-[(2-O-β-D-glucopyranosyl-3-O-β-D-glucopyranosyl-β-D-glucopyranosyl)oxy] ent-kaur-16-en-19-oic acid-[(2-O-{2-O-β-D-glucopyranosyl}-β-D-glucopyranosyl-β-D-glucopyranosyl)ester (FIG. 12).

Example 8: Production of Steviol Glycosides Rebaudioside R6-4A and Rebaudioside R6-4B by Enzymatic Bioconversion Full-length DNA fragments of all candidate UDP-glucosyltransferase (UGT) genes were commercially synthesized. Almost all codons of the cDNA were changed to those preferred for *E. coli* (Genscript, NJ). The synthesized DNA was cloned into a bacterial expression vector pETite N-His SUMO Kan Vector (Lucigen).

Each expression construct was transformed into *E. coli* BL21 (DE3), which was subsequently grown in LB media containing 50 μg/mL kanamycin at 37° C. until reaching an $OD_{600}$ of 0.8-1.0. Protein expression was induced by addition of 1 mM isopropyl β-D-1-thiogalactopyranoside (IPTG) and the culture was further grown at 16° C. for 22 hr. Cells were harvested by centrifugation (3,000×g; 10 min; 4° C.). The cell pellets were collected and were either used immediately or stored at −80° C.

The cell pellets typically were re-suspended in lysis buffer (50 mM potassium phosphate buffer, pH 7.2, 25 ug/ml lysozyme, 5 ug/ml DNase I, 20 mM imidazole, 500 mM NaCl, 10% glycerol, and 0.4% Triton X-100). The cells were disrupted by sonication under 4° C., and the cell debris was clarified by centrifugation (18,000×g; 30 min). Supernatant was loaded to an equilibrated (equilibration buffer: 50 mM potassium phosphate buffer, pH 7.2, 20 mM imidazole, 500 mM NaCl, 10% glycerol) Ni-NTA (Qiagen) affinity column. After loading of protein sample, the column was washed with equilibration buffer to remove unbound contaminant proteins. The His-tagged UGT recombinant polypeptides were eluted by equilibration buffer containing 250 mM imidazole.

The purified candidate UGTs recombinant polypeptides were assayed for glycosylation activity by using rebaudioside Z (a mixture of Reb Z1 and Reb Z2) as substrate. Typically, the recombinant polypeptide (10-50 μg) was tested in a 200 μl in vitro reaction system. The reaction system contained 50 mM potassium phosphate buffer, pH 7.2, 3 mM $MgCl_2$, 1 mg/ml Reb Z substrate, 1 mM UDP-glucose or UDP and/or sucrose synthase (SUS) and 250 mM sucrose. The reaction was performed at 30-37° C. and 50 ul reaction was terminated by adding 200 μL 1-butanol at various time points. The samples were extracted three times with 200 μL 1-butanol. The pooled fraction was dried and dissolved in 100 μL 80% methanol for high-performance liquid chromatography (HPLC) analysis.

HPLC analysis was then performed using a Dionex UPLC ultimate 3000 system (Sunnyvale, CA), including a quaternary pump, a temperature-controlled column compartment, an auto sampler and a UV absorbance detector. A Synergi Hydro-RP column (Phenomenex) with guard column was used for the characterization of steviol glycosides in the pooled samples. Acetonitrile and water was used for mobile solution in the HPLC analysis. The detection wavelength used in the HPLC analysis was 210 nm.

Figure 15:
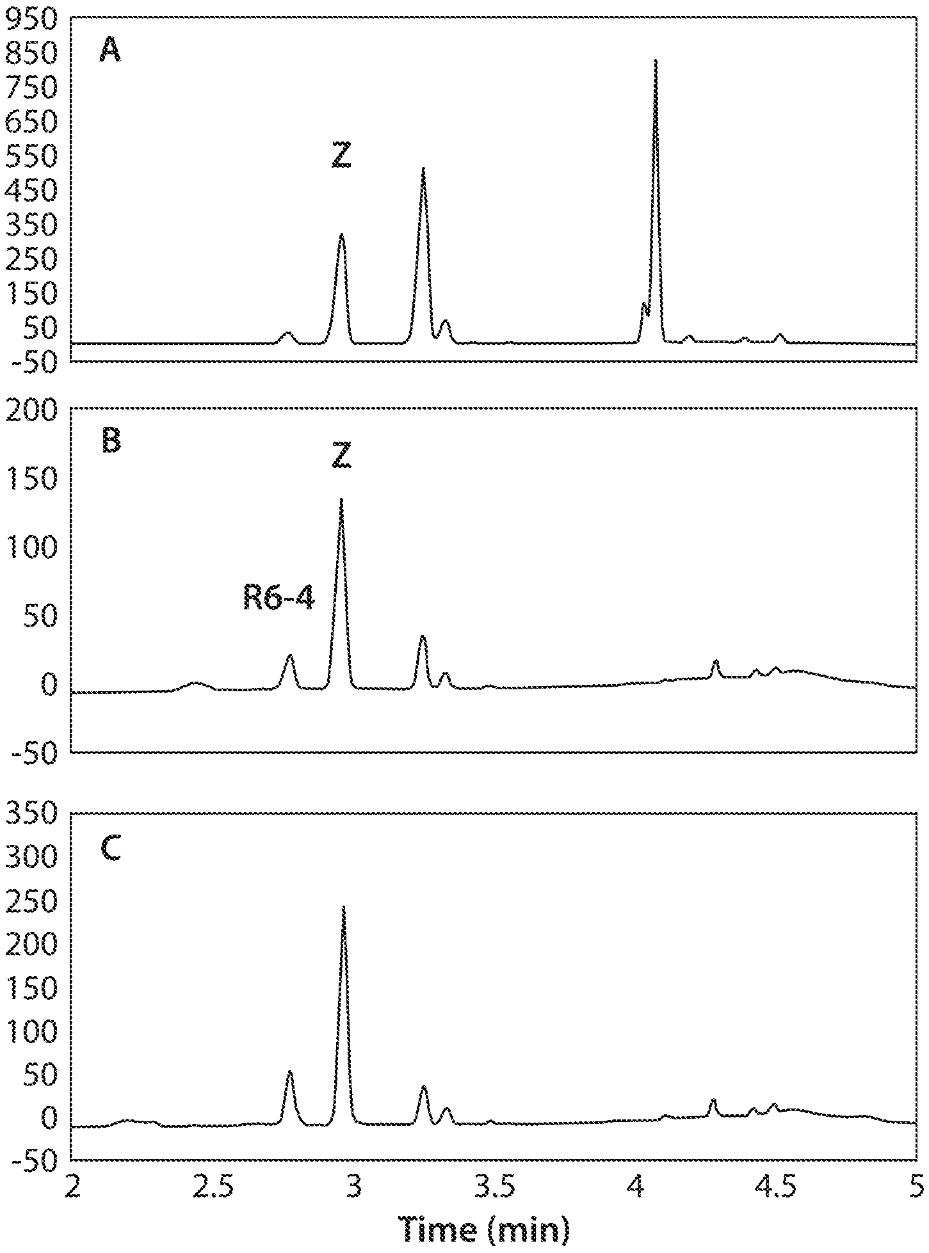
FIG. 15. HV1 catalysis reaction to produce R6-4 from Reb Z. Panel A shows the HPLC retention time of rebaudioside Z ("Z") standard. R6-4 was enzymatically produced by HV1 at 3 hours (Panel B) and 24 hours (Panel C).

After activity screening, HV1 (SEQ ID NO: 3) was found to have strong activity to produce R6-4 steviol glycoside (FIG. 14). As shown in FIG. 15, HV1 can convert Reb Z to R6-4. More R6-4 can be produced at later reaction time (FIG. 15, Panel C).

Example 9: Identification of R6-4 Production by LC-MS Analysis

In order to confirm the produced compounds, the produced compound was analyzed by LC-MS analysis comparing to standards and their identities confirmed.

Same samples from above enzymatical bioconversion were analyzed by LC-MS using the Synergy Hydro-RP column Mobile phase A was 0.1% formic acid in water, and mobile phase B was 0.1% formic acid in acetonitrile. The flow rate was 0.6 ml/minute. Mass spectrometry analysis of the samples was done on the Q Exactive Hybrid Quadrupole-Orbitrap Mass Spectrometer (Thermo Fisher Scientific) with an optimized method in positive ion mode.

Figure 16:
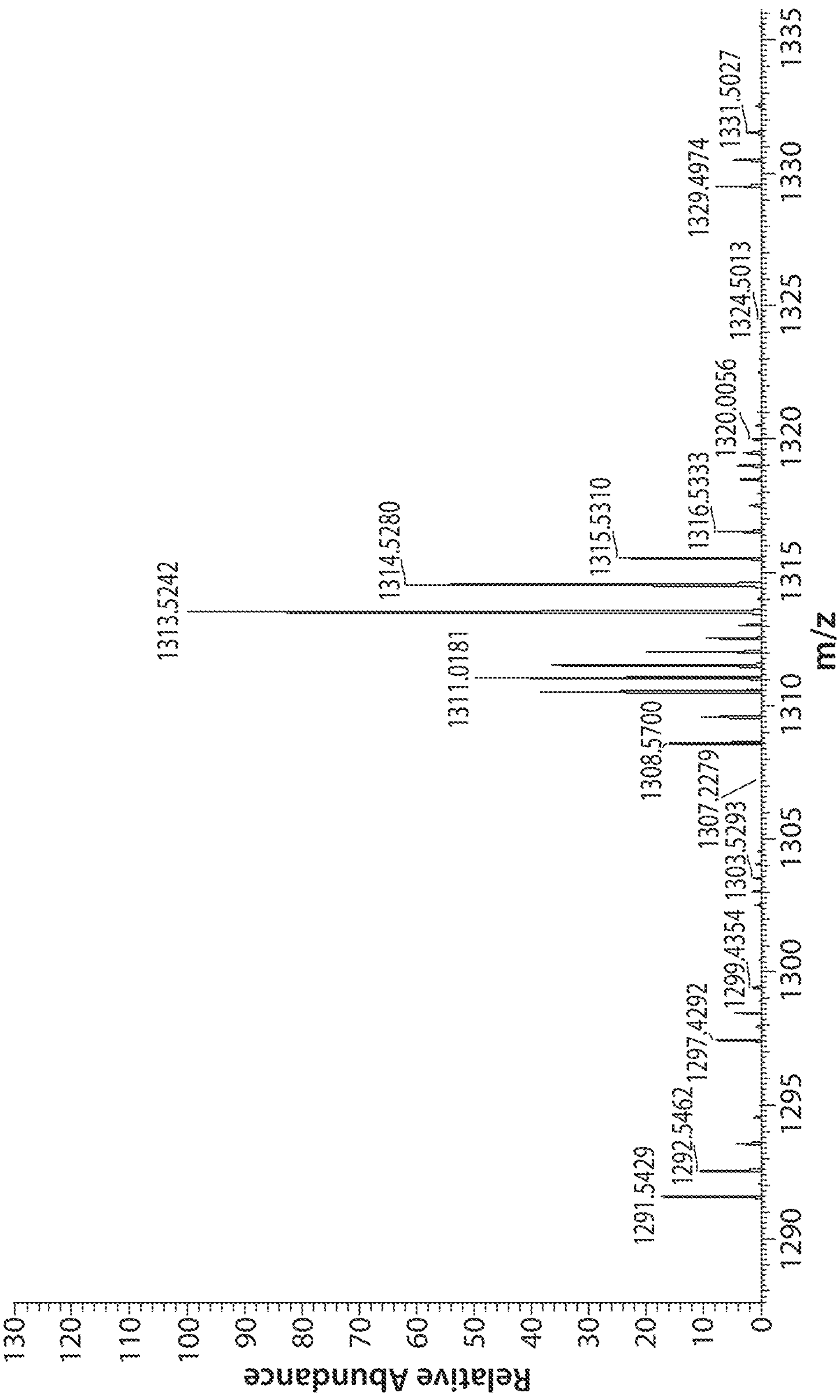
FIG. 16. LC MS analysis of the produced R6-4 compound.

The molecular formula of compound R6-4 has been deduced as $C_{56}H_{9}O_{33}$ on the basis of its positive high resolution (HR) mass spectrum which showed adducts ions corresponding to [M+Na]+ at m/z 1313.5242 (FIG. 16). The predicted structures of R6-4A and R6-4B are presented in FIGS. 14 and 17.

Example 10: The Structure of R6-4 was Analyzed by NMR

The produced R6-4 compound was purified by semi preparative chromatography as described above.

HRMS data were generated with a LTQ Orbitrap Discovery HRMS instrument, with its resolution set to 30 k. Scanned data from m/z 150 to 1500 in positive ion electrospray mode. The needle voltage was set to 4 kV; the other source conditions were sheath gas=25, aux gas=0, sweep gas=5 (all gas flows in arbitrary units), capillary voltage=30V, capillary temperature=300° C., and tube lens voltage=75. Sample was diluted with pyridine and injected 50 microliters.

NMR spectra were acquired on Bruker Avance DRX 500 MHz or Varian INOVA 600 MHz instrument instruments using standard pulse sequences. The 1D ($^{1}H$ and $^{13}C$) and 2D (TOCSY, HSQC, ROESY, and HMBC) NMR spectra were performed in $C_5D_5N$.

The molecular formula of R6-4 compound has been deduced as $C_{56}H_{90}O_{33}$ on the basis of its positive high resolution (HR) mass spectrum which showed adducts at m/z 1308.5692 and 1313.5237 corresponding to $[M+NH_4]^+$ and $[M+Na]^+$ ions respectively, and this composition was supported by $^{13}C$ NMR spectral data. The NMR spectral data and HPLC of R6-4 indicated that this compound is a mixture of two major compounds R6-4A and R6-4B in the ratio of about 70:30, hence the $^{1}H$ and $^{13}C$ NMR spectral data of R6-4 showed two peaks for majority of protons and carbons present in its molecular structure. The $^{1}H$ NMR spectrum of R6-4 showed the presence of two sp3 methyl singlets, two olefinic protons as singlets of an exocyclic double bond, nine sp3 methylene and two sp3 methine protons between characteristic for the ent-kaurane diterpenoids isolated earlier from the genus *Stevia*. Enzymatic hydrolysis of R6-4 furnished a compound which was found identical to steviol based on NMR spectral data (Ohtani et al, 1992). Acid hydrolysis of R6-4 with 5% $H_2SO_4$ afforded D-glucose which was identified by direct comparison with authentic sample by TLC suggested the presence of six glucopyranosyl moieties in its molecular structure (Bedir et al., 2001; Chaturvedula et al., 2003; and Huan et al., 1998). The configuration of D-glucose was identified by preparing its corresponding thiocarbamoyl-thiazolidine carboxylate derivative with L-cysteine methyl ester and O-tolyl isothiocyanate, and in comparison, of its retention time with the standard sugars as described in the literature comparison (Tanaka et al., 2007). Based on the results from NMR spectral data and hydrolysis studies it was concluded that there are six glucosyl units in the molecular structure of R6-4 which was supported by the $^{1}H$ NMR spectrum that showed six anomeric protons resonating between δ 5.03-6.44. Further, the large coupling constants observed for all six anomeric protons of the glucosyl moieties suggested their β-orientation as reported for steviol glycosides.

The $^{1}H$ and $^{13}C$ NMR values for all protons and carbons for compounds R6-4A and R6-4B were assigned on the basis of TOCSY, HMQC, HMBC and ROESY correlations and are given in Table 3.

A close comparison of the $^{1}H$ and $^{13}C$ NMR spectrum with rebaudioside Z (a mixture of Reb Z1 and Reb Z2) as well as from the key TOCSY, ROESY and HMBC correlations suggested that R6-4 compound is a mixture of two steviol glycosides of which the major compound is having three glycosyl units that are attached at the C-13 hydroxyl as an ether and another three glycosyl units at C-19 as an ester as shown in R6-4A whereas the minor compound is having two glycosyl units that are attached at the C-13 hydroxyl as an ether and four glycosyl units at C-19 as an ester that was represented in R6-4B.

Figure 17:
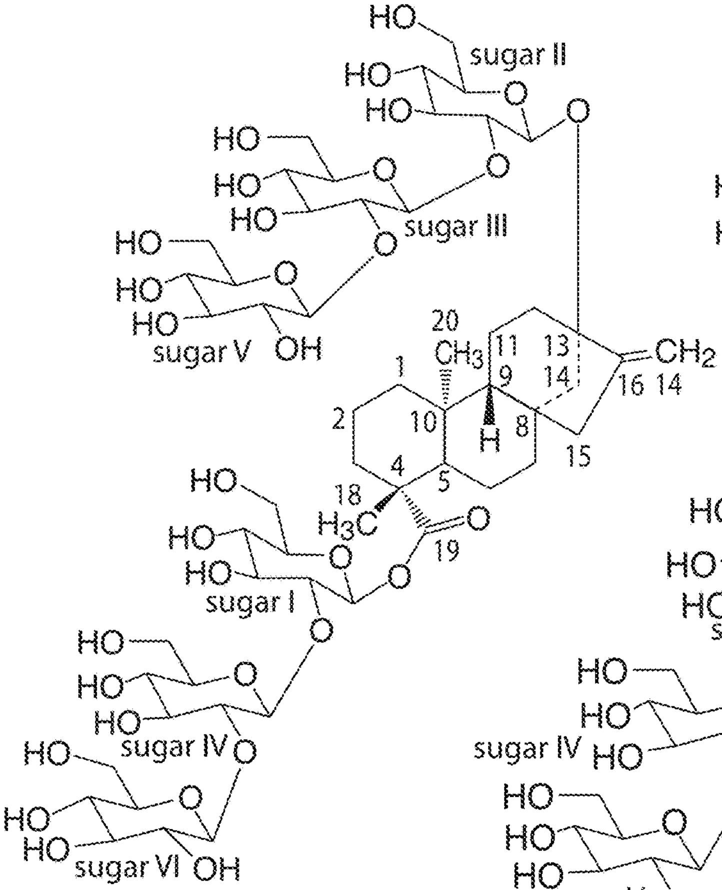
FIG. 17. The structure of R6-4A and R6-4B.
Figure 17:
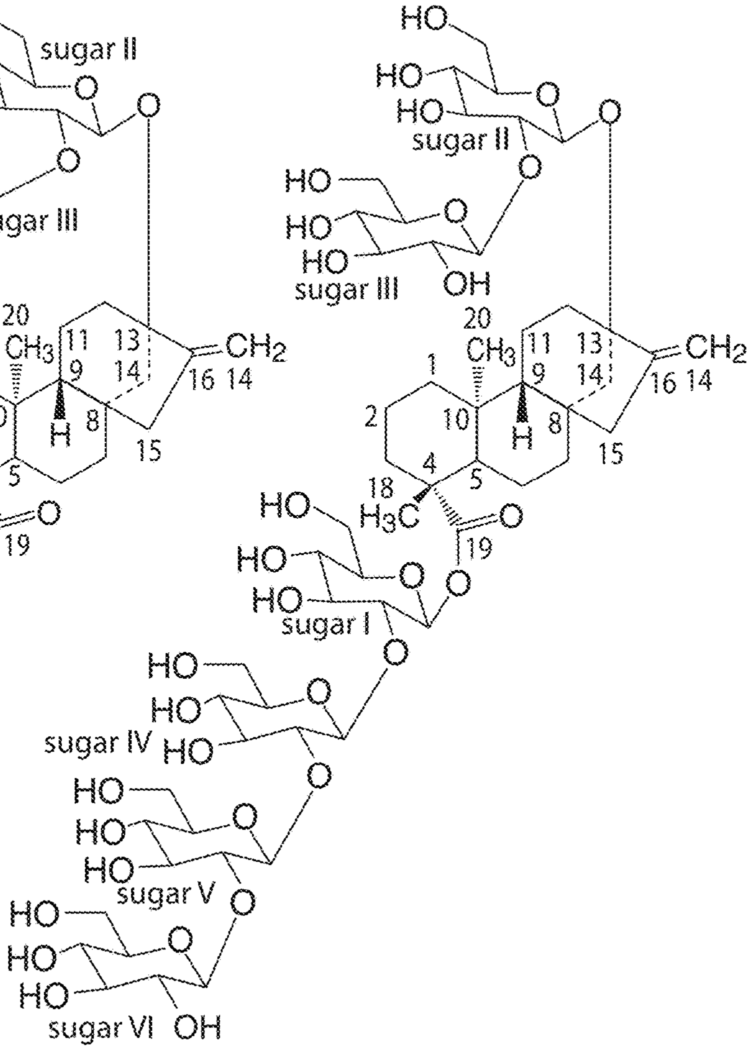

Based on the results of NMR and HR mass spectral data as well as hydrolysis studies, the structure of R6-4 produced by the enzymatic conversion of rebaudioside Z which is a mixture of two major compounds was deduced as 13-[(2-O-{2-O-β-D-glucopyranosyl-β-D-glucopyranosyl}-β-D-glucopyranosyl)oxy] ent-kaur-16-en-19-oic acid-[(2-O-{2-O-β-D-glucopyranosyl}-β-D-glucopyranosyl-β-D-glucopyranosyl)ester (R6-4A) or 13-[(2-O-β-D-glucopyranosyl-β-D-glucopyranosyl)oxy] ent-kaur-16-en-19-oic acid-R2-O-[(2-O-{2-O-β-D-glucopyranosyl-β-D-glucopyranosyl}-β-D-glucopyranosyl)-β-D-glucopyranosyl) ester (R6-4B) (FIG. 17).

R6-4 compound (1 mg) was dissolved in 10 ml of 0.1 M sodium acetate buffer by maintaining pH at 4.5 and 250 uL of crude pectinase from *Aspergillus niger* (Sigma-Aldrich) was added. The mixture was stirred at 50° C. for 48 hr and the product precipitated out during the reaction was filtered and then solidified. The resulting product obtained was identified as steviol by comparison of their 1H NMR spectral data and co-TLC (Ohtani et al., 1992).

R6-4 compound (500 μg) is dissolved in MeOH (5 ml) and added 5% $H_2SO_4$ (15 mL). The mixture was refluxed for 24 hours, cooled to room temperature and then neutralized with saturated sodium carbonate. The aqueous phase was extracted with ethyl acetate (EtOAc, 2×25 ml) and the aqueous layer was concentrated and compared with standard sugars using the TLC system EtOAc/n-butanol/water (2:7:1) and $CH_2Cl_2$/MeOH/water (10:6:1) (Bedir et al., 2001; Chaturvedula et al., 2003; Huan et al., 1998); the sugars in R6-4 were identified as D-glucose.

R6-4 compound (1 mg) was hydrolyzed with 0.5 M HCl (2 mL) for 1.5 h. After cooling, the mixture was passed through an Amberlite IRA400 column and the eluate was lyophilized. The residue was dissolved in pyridine (0.75 mL) and heated with L-cysteine methyl ester HCl (5 mg) at 60° C. for 1.5 h, and then O-tolyl isothiocyanate (30 μL) was added to the mixture and heated at 60° C. for an additional 1.5 h. HPLC analysis of the reaction mixture was performed by a Phenomenex Luna column [C18, 150×4.6 mm (5 u)] using the mobile phase 25% acetonitrile-0.2% TFA water, 1 mL/min under UV detection at 250 nm. The sugar was identified as D-glucose (tR, 12.38) [authentic samples, D-glucose (tR, 12.44) and L-glucose (tR, 11.30 min)] (Tanaka et al., 2007).

Sequences:
UGT76G1: Amino Acid Sequence
(SEQ ID NO: 1)

MENKTETTVRRRRRIILFPVPFQGHINPILQLANVLYSKGFSITIFHTNFNKPKTSNYPHF

TFRFILDNDPQDERISNLPTHGPLAGMRIPIINEHGADELRRELELLMLASEEDEEVSCLI

TDALWYFAQSVADSLNLRRLVLMTSSLFNFHAHVSLPQFDELGYLDPDDKTRLEEQA

SGFPMLKVKDIKSAYSNWQILKEILGKMIKQTKASSGVIWNSFKELEESELETVIREIPA

PSFLIPLPKHLTASSSSLLDHDRTVFQWLDQQPPSSVLYVSFGSTSEVDEKDFLEIARGL

VDSKQSFLWVVRPGFVKGSTWVEPLPDGFLGERGRIVKWVPQQEVLAHGAIGAFWT

HSGWNSTLESVCEGVPMIFSDFGLDQPLNARYMSDVLKVGVYLENGWERGEIANAIR

RVMVDEEGEYIRQNARVLKQKADVSLMKGGSSYESLESLVSYISSL

UGT76G1: DNA Sequence
(SEQ ID NO: 2)

ATGGAGAATAAGACAGAAACAACCGTAAGACGGAGGCGGAGGATTATCTTGTTCC

CTGTACCATTTCAGGGCCATATTAATCCGATCCTCCAATTAGCAAACGTCCTCTAC

TCCAAGGGATTTTCAATAACAATCTTCCATACTAACTTTAACAAGCCTAAAACGAG

TAATTATCCTCACTTTACATTCAGGTTCATTCTAGACAACGACCCTCAGGATGAGC

GTATCTCAAATTTACCTACGCATGGCCCCTTGGCAGGTATGCGAATACCAATAATC

AATGAGCATGGAGCCGATGAACTCCGTCGCGAGTTAGAGCTTCTCATGCTCGCAA

GTGAGGAAGACGAGGAAGTTTCGTGCCTAATAACTGATGCGCTTTGGTACTTCGCC

CAATCAGTCGCAGACTCACTGAATCTACGCCGTTTGGTCCTTATGACAAGTTCATT

ATTCAACTTTCACGCACATGTATCACTGCCGCAATTTGACGAGTTGGGTTACCTGG

ACCCGGATGACAAAACGCGATTGGAGGAACAAGCGTCGGGCTTCCCCATGCTGAA

AGTCAAAGATATTAAGAGCGCTTATAGTAATTGGCAAATTCTGAAAGAAATTCTC

GGAAAAATGATAAAGCAAACCAAAGCGTCCTCTGGAGTAATCTGGAACTCCTTCA

AGGAGTTAGAGGAATCTGAACTTGAAACGGTCATCAGAGAAATCCCCGCTCCCTC

GTTCTTAATTCCACTACCCAAGCACCTTACTGCAAGTAGCAGTTCCCTCCTAGATC

ATGACCGAACCGTGTTTCAGTGGCTGGATCAGCAACCCCCGTCGTCAGTTCTATAT

GTAAGCTTTGGGAGTACTTCGGAAGTGGATGAAAAGGACTTCTTAGAGATTGCGC

GAGGGCTCGTGGATAGCAAACAGAGCTTCCTGTGGGTAGTGAGACCGGGATTCGT

-continued

TAAGGGCTCGACGTGGGTCGAGCCGTTGCCAGATGGTTTTCTAGGGGAGAGAGGG

AGAATCGTGAAATGGGTTCCACAGCAAGAGGTTTTGGCTCACGGAGCTATAGGGG

CCTTTTGGACCCACTCTGGTTGGAATTCTACTCTTGAAAGTGTCTGTGAAGGCGTT

CCAATGATATTTTCTGATTTTGGGCTTGACCAGCCTCTAAACGCTCGCTATATGTCT

GATGTGTTGAAGGTTGGCGTGTACCTGGAGAATGGTTGGGAAAGGGGGGAAATTG

CCAACGCCATACGCCGGGTAATGGTGGACGAGGAAGGTGAGTACATACGTCAGAA

CGCTCGGGTTTTAAAACAAAAAGCGGACGTCAGCCTTATGAAGGGAGGTAGCTCC

TATGAATCCCTAGAATCCTTGGTAAGCTATATATCTTCGTTATAA

HV1 UDP-glycosyltransferase: Amino Acid Sequence (SEQ ID NO: 3)

MDGNSSSSPLHVVICPWLALGHLLPCLDIAERLASRGHRVSFVSTPRNIARLPPLRPAV

APLVDFVALPLPHVDGLPEGAESTNDVPYDKFELHRKAFDGLAAPFSEFLRAACAEGA

GSRPDWLIVDTFHHWAAAAAVENKVPCVMLLLGAATVIAGFARGVSEHAAAAVGKE

RPAAEAPSFETERRKLMTTQNASGMTVAERYFLTLMRSDLVAIRSCAEWEPESVAALT

TLAGKPVVPLGLLPPSPEGGRGVSKEDAAVRWLDAQPAKSVVYVALGSEVPLRAEQV

HELALGLELSGARFLWALRKPTDAPDAAVLPPGFEERTRGRGLVVTGWVPQIGVLAH

GAVAAFLTHCGWNSTIEGLLFGHPLIMLPISSDQGPNARLMEGRKVGMQVPRDESDGS

FRREDVAATVRAVAVEEDGRRVFTANAKKMQEIVADGACHERCIDGFIQQLRSYKA

HV1 UDP-glycosyltransferase: DNA Sequence (SEQ ID NO: 4)

ATGGATGGTAACTCCTCCTCCTCGCCGCTGCATGTGGTCATTTGTCCGTGGCTGGC

TCTGGGTCACCTGCTGCCGTGTCTGGATATTGCTGAACGTCTGGCGTCACGCGGCC

ATCGTGTCAGTTTTGTGTCCACCCCGCGCAACATTGCCCGTCTGCCGCCGCTGCGT

CCGGCTGTTGCACCGCTGGTTGATTTCGTCGCACTGCCGCTGCCGCATGTTGACGG

TCTGCCGGAGGGTGCGGAATCGACCAATGATGTGCCGTATGACAAATTTGAACTG

CACCGTAAGGCGTTCGATGGTCTGGCGGCCCCGTTTAGCGAATTTCTGCGTGCAGC

TTGCGCAGAAGGTGCAGGTTCTCGCCCGGATTGGCTGATTGTGGACACCTTTCATC

ACTGGGCGGCGGCGGCGGCGGTGGAAAACAAAGTGCCGTGTGTTATGCTGCTGCT

GGGTGCAGCAACGGTGATCGCTGGTTTCGCGCGTGGTGTTAGCGAACATGCGGCG

GCGGCGGTGGGTAAAGAACGTCCGGCTGCGGAAGCCCCGAGTTTTGAAACCGAAC

GTCGCAAGCTGATGACCACGCAGAATGCCTCCGGCATGACCGTGGCAGAACGCTA

TTTCCTGACGCTGATGCGTAGCGATCTGGTTGCCATCCGCTCTTGCGCAGAATGGG

AACCGGAAAGCGTGGCAGCACTGACCACGCTGGCAGGTAAACCGGTGGTTCCGCT

GGGTCTGCTGCCGCCGAGTCCGGAAGGCGGTCGTGGCGTTTCCAAAGAAGATGCT

GCGGTCCGTTGGCTGGACGCACAGCCGGCAAAGTCAGTCGTGTACGTCGCACTGG

GTTCGGAAGTGCCGCTGCGTGCGGAACAAGTTCACGAACTGGCACTGGGCCTGGA

ACTGAGCGGTGCTCGCTTTCTGTGGGCGCTGCGTAAACCGACCGATGCACCGGAC

GCCGCAGTGCTGCCGCCGGGTTTCGAAGAACGTACCCGCGGCCGTGGTCTGGTTGT

CACGGGTTGGGTGCCGCAGATTGGCGTTCTGGCTCATGGTGCGGTGGCTGCGTTTC

TGACCCACTGTGGCTGGAACTCTACGATCGAAGGCCTGCTGTTCGGTCATCCGCTG

ATTATGCTGCCGATCAGCTCTGATCAGGGTCCGAATGCGCGCCTGATGGAAGGCC

GTAAAGTCGGTATGCAAGTGCCGCGTGATGAATCAGACGGCTCGTTTCGTCGCGA

-continued

AGATGTTGCCGCAACCGTCCGCGCCGTGGCAGTTGAAGAAGACGGTCGTCGCGTC

TTCACGGCTAACGCGAAAAAGATGCAAGAAATTGTGGCCGATGGCGCATGCCACG

AACGTTGTATTGACGGTTTTATCCAGCAACTGCGCAGTTACAAGGCGTAA

UGT76G1-sucrose synthase (SUS) fusion enzyme: Amino Acid Sequence (SEQ ID NO: 5)

MENKTETTVRRRRRIILFPVPFQGHINPILQLANVLYSKGFSITIFHTNFNKPKTSNYPHF

TFRFILDNDPQDERISNLPTHGPLAGMRIPIINEHGADELRRELELLMLASEEDEEVSCLI

TDALWYFAQSVADSLNLRRLVLMTSSLFNFHAHVSLPQFDELGYLDPDDKTRLEEQA

SGFPMLKVKDIKSAYSNWQILKEILGKMIKQTKASSGVIWNSFKELEESELETVIREIPA

PSFLIPLPKHLTASSSSLLDHDRTVFQWLDQQPPSSVLYVSFGSTSEVDEKDFLEIARGL

VDSKQSFLWVVRPGFVKGSTWVEPLPDGFLGERGRIVKWVPQQEVLAHGAIGAFWT

HSGWNSTLESVCEGVPMIFSDFGLDQPLNARYMSDVLKVGVYLENGWERGEIANAIR

RVMVDEEGEYIRQNARVLKQKADVSLMKGGSSYESLESLVSYISSLGSGANAERMITR

VHSQRERLNETLVSERNEVLALLSRVEAKGKGILQQNQIIAEFEALPEQTRKKLEGGPF

FDLLKSTQEAIVLPPWVALAVRPRPGVWEYLRVNLHALVVEELQPAEFLHFKEELVD

GVKNGNFTLELDFEPFNASIPRPTLHKYIGNGVDFLNRHLSAKLFHDKESLLPLLKFLR

LHSHQGKNLMLSEKIQNLNTLQHTLRKAEEYLAELKSETLYEEFEAKFEEIGLERGWG

DNAERVLDMIRLLLDLLEAPDPCTLETFLGRVPMVFNVVILSPHGYFAQDNVLGYPDT

GGQVVYILDQVRALEIEMLQRIKQQGLNIKPRILILTRLLPDAVGTTCGERLERVYDSE

YCDILRVPFRTEKGIVRKWISRFEVWPYLETYTEDAAVELSKELNGKPDLIIGNYSDGN

LVASLLAHKLGVTQCTIAHALEKTKYPDSDIYWKKLDDKYHFSCQFTADIFAMNHTD

FIITSTFQEIAGSKETVGQYESHTAFTLPGLYRVVHGIDVFDPKFNIVSPGADMSIYFPYT

EEKRRLTKFHSEIEELLYSDVENKEHLCVLKDKKKPILFTMARLDRVKNLSGLVEWYG

KNTRLRELANLVVVGGDRRKESKDNEEKAEMKKMYDLIEEYKLNGQFRWISSQMDR

VRNGELYRYICDTKGAFVQPALYEAFGLTVVEAMTCGLPTFATCKGGPAEIIVHGKSG

FHIDPYHGDQAADTLADFFTKCKEDPSHWDEISKGGLQRIEEKYTWQIYSQRLLTLTG

VYGFWKHVSNLDRLEARRYLEMFYALKYRPLAQAVPLAQDD

UGT76G1-sucrose synthase (SUS) fusion enzyme: DNA Sequence (SEQ ID NO: 6)

ATGGAGAATAAGACAGAAACAACCGTAAGACGGAGGCGGAGGATTATCTTGTTCC

CTGTACCATTTCAGGGCCATATTAATCCGATCCTCCAATTAGCAAACGTCCTCTAC

TCCAAGGGATTTTCAATAACAATCTTCCATACTAACTTTAACAAGCCTAAAACGAG

TAATTATCCTCACTTTACATTCAGGTTCATTCTAGACAACGACCCTCAGGATGAGC

GTATCTCAAATTTACCTACGCATGGCCCCTTGGCAGGTATGCGAATACCAATAATC

AATGAGCATGGAGCCGATGAACTCCGTCGCGAGTTAGAGCTTCTCATGCTCGCAA

GTGAGGAAGACGAGGAAGTTTCGTGCCTAATAACTGATGCGCTTTGGTACTTCGCC

CAATCAGTCGCAGACTCACTGAATCTACGCCGTTTGGTCCTTATGACAAGTTCATT

ATTCAACTTTCACGCACATGTATCACTGCCGCAATTTGACGAGTTGGGTTACCTGG

ACCCGGATGACAAAACGCGATTGGAGGAACAAGCGTCGGGCTTCCCCATGCTGAA

AGTCAAAGATATTAAGAGCGCTTATAGTAATTGGCAAATTCTGAAAGAAATTCTC

GGAAAAATGATAAAGCAAACCAAAGCGTCCTCTGGAGTAATCTGGAACTCCTTCA

AGGAGTTAGAGGAATCTGAACTTGAAACGGTCATCAGAGAAATCCCCGCTCCCTC

-continued

GTTCTTAATTCCACTACCCAAGCACCTTACTGCAAGTAGCAGTTCCCTCCTAGATC

ATGACCGAACCGTGTTTCAGTGGCTGGATCAGCAACCCCCGTCGTCAGTTCTATAT

GTAAGCTTTGGGAGTACTTCGGAAGTGGATGAAAAGGACTTCTTAGAGATTGCGC

GAGGGCTCGTGGATAGCAAACAGAGCTTCCTGTGGGTAGTGAGACCGGGATTCGT

TAAGGGCTCGACGTGGGTCGAGCCGTTGCCAGATGGTTTTCTAGGGGAGAGAGGG

AGAATCGTGAAATGGGTTCCACAGCAAGAGGTTTTGGCTCACGGAGCTATAGGGG

CCTTTTGGACCCACTCTGGTTGGAATTCTACTCTTGAAAGTGTCTGTGAAGGCGTT

CCAATGATATTTTCTGATTTTGGGCTTGACCAGCCTCTAAACGCTCGCTATATGTCT

GATGTGTTGAAGGTTGGCGTGTACCTGGAGAATGGTTGGGAAAGGGGGGAAATTG

CCAACGCCATACGCCGGGTAATGGTGGACGAGGAAGGTGAGTACATACGTCAGAA

CGCTCGGGTTTTAAAACAAAAAGCGGACGTCAGCCTTATGAAGGGAGGTAGCTCC

TATGAATCCCTAGAATCCTTGGTAAGCTATATATCTTCGTTAGGTTCTGGTGCAAA

CGCTGAACGTATGATAACGCGCGTCCACAGCCAACGTGAGCGTTTGAACGAAACG

CTTGTTTCTGAGAGAAACGAAGTCCTTGCCTTGCTTTCCAGGGTTGAAGCCAAAGG

TAAAGGTATTTTACAACAAAACCAGATCATTGCTGAATTCGAAGCTTTGCCTGAAC

AAACCCGGAAGAAACTTGAAGGTGGTCCTTTCTTTGACCTTCTCAAATCCACTCAG

GAAGCAATTGTGTTGCCACCATGGGTTGCTCTAGCTGTGAGGCCAAGGCCTGGTGT

TTGGGAATACTTACGAGTCAATCTCCATGCTCTTGTCGTTGAAGAACTCCAACCTG

CTGAGTTTCTTCATTTCAAGGAAGAACTCGTTGATGGAGTTAAGAATGGTAATTTC

ACTCTTGAGCTTGATTTCGAGCCATTCAATGCGTCTATCCCTCGTCCAACACTCCAC

AAATACATTGGAAATGGTGTTGACTTCCTTAACCGTCATTTATCGGCTAAGCTCTT

CCATGACAAGGAGAGTTTGCTTCCATTGCTTAAGTTCCTTCGTCTTCACAGCCACC

AGGGCAAGAACCTGATGTTGAGCGAGAAGATTCAGAACCTCAACACTCTGCAACA

CACCTTGAGGAAAGCAGAAGAGTATCTAGCAGAGCTTAAGTCCGAAACACTGTAT

GAAGAGTTTGAGGCCAAGTTTGAGGAGATTGGTCTTGAGAGGGGATGGGGAGACA

ATGCAGAGCGTGTCCTTGACATGATACGTCTTCTTTTGGACCTTCTTGAGGCGCCT

GATCCTTGCACTCTTGAGACTTTTCTTGGAAGAGTACCAATGGTGTTCAACGTTGT

GATCCTCTCTCCACATGGTTACTTTGCTCAGGACAATGTTCTTGGTTACCCTGACAC

TGGTGGACAGGTTGTTTACATTCTTGATCAAGTTCGTGCTCTGGAGATAGAGATGC

TTCAACGTATTAAGCAACAAGGACTCAACATTAAACCAAGGATTCTCATTCTAACT

CGACTTCTACCTGATGCGGTAGGAACTACATGCGGTGAACGTCTCGAGAGAGTTT

ATGATTCTGAGTACTGTGATATTCTTCGTGTGCCCTTCAGAACAGAGAAGGGTATT

GTTCGCAAATGGATCTCAAGGTTCGAAGTCTGGCCATATCTAGAGACTTACACCGA

GGATGCTGCGGTTGAGCTATCGAAAGAATTGAATGGCAAGCCTGACCTTATCATT

GGTAACTACAGTGATGGAAATCTTGTTGCTTCTTTATTGGCTCACAAACTTGGTGT

CACTCAGTGTACCATTGCTCATGCTCTTGAGAAAACAAAGTACCCGGATTCTGATA

TCTACTGGAAGAAGCTTGACGACAAGTACCATTTCTCATGCCAGTTCACTGCGGAT

ATTTTCGCAATGAACCACACTGATTTCATCATCACTAGTACTTTCCAAGAAATTGC

TGGAAGCAAAGAAACTGTTGGGCAGTATGAAAGCCACACAGCCTTTACTCTTCCC

GGATTGTATCGAGTTGTTCACGGGATTGATGTGTTTGATCCCAAGTTCAACATTGT

CTCTCCTGGTGCTGATATGAGCATCTACTTCCCTTACACAGAGGAGAAGCGTAGAT

-continued

TGACTAAGTTCCACTCTGAGATCGAGGAGCTCCTCTACAGCGATGTTGAGAACAA

AGAGCACTTATGTGTGCTCAAGGACAAGAAGAAGCCGATTCTCTTCACAATGGCT

AGGCTTGATCGTGTCAAGAACTTGTCAGGTCTTGTTGAGTGGTACGGGAAGAACA

CCCGCTTGCGTGAGCTAGCTAACTTGGTTGTTGTTGGAGGAGACAGGAGGAAAGA

GTCAAAGGACAATGAAGAGAAAGCAGAGATGAAGAAAATGTATGATCTCATTGA

GGAATACAAGCTAAACGGTCAGTTCAGGTGGATCTCCTCTCAGATGGACCGGGTA

AGGAACGGTGAGCTGTACCGGTACATCTGTGACACCAAGGGTGCTTTTGTCCAAC

CTGCATTATATGAAGCCTTTGGGTTAACTGTTGTGGAGGCTATGACTTGTGGTTTA

CCGACTTTCGCCACTTGCAAAGGTGGTCCAGCTGAGATCATTGTGCACGGTAAATC

GGGTTTCCACATTGACCCTTACCATGGTGATCAGGCTGCTGATACTCTTGCTGATTT

CTTCACCAAGTGTAAGGAGGATCCATCTCACTGGGATGAGATCTCAAAAGGAGGG

CTTCAGAGGATTGAGGAGAAATACACTTGGCAAATCTATTCACAGAGGCTCTTGA

CATTGACTGGTGTGTATGGATTCTGGAAGCATGTCTCGAACCTTGACCGTCTTGAG

GCTCGCCGTTACCTTGAAATGTTCTATGCATTGAAGTATCGCCCATTGGCTCAGGC

TGTTCCTCTTGCACAAGATGATTGA

HV1-SUS fusion enzyme: Amino Acid Sequence (SEQ ID NO: 7)

MDGNSSSSPLHVVICPWLALGHLLPCLDIAERLASRGHRVSFVSTPRNIARLPPLRPAV

APLVDFVALPLPHVDGLPEGAESTNDVPYDKFELHRKAFDGLAAPFSEFLRAACAEGA

GSRPDWLIVDTFHHWAAAAAVENKVPCVMLLLGAATVIAGFARGVSEHAAAAVGKE

RPAAEAPSFETERRKLMTTQNASGMTVAERYFLTLMRSDLVAIRSCAEWEPESVAALT

TLAGKPVVPLGLLPPSPEGGRGVSKEDAAVRWLDAQPAKSVVYVALGSEVPLRAEQV

HELALGLELSGARFLWALRKPTDAPDAAVLPPGFEERTRGRGLVVTGWVPQIGVLAH

GAVAAFLTHCGWNSTIEGLLFGHPLIMLPISSDQGPNARLMEGRKVGMQVPRDESDGS

FRREDVAATVRAVAVEEDGRRVFTANAKKMQEIVADGACHERCIDGFIQQLRSYKAG

SGANAERMITRVHSQRERLNETLVSERNEVLALLSRVEAKGKGILQQNQIIAEFEALPE

QTRKKLEGGPFFDLLKSTQEAIVLPPWVALAVRPRPGVWEYLRVNLHALVVEELQPA

EFLHFKEELVDGVKNGNFTLELDFEPFNASIPRPTLHKYIGNGVDFLNRHLSAKLFHDK

ESLLPLLKFLRLHSHQGKNLMLSEKIQNLNTLQHTLRKAEEYLAELKSETLYEEFEAKF

EEIGLERGWGDNAERVLDMIRLLLDLLEAPDPCTLETFLGRVPMVFNVVILSPHGYFA

QDNVLGYPDTGGQVVYILDQVRALEIEMLQRIKQQGLNIKPRILILTRLLPDAVGTTCG

ERLERVYDSEYCDILRVPFRTEKGIVRKWISRFEVWPYLETYTEDAAVELSKELNGKP

DLIIGNYSDGNLVASLLAHKLGVTQCTIAHALEKTKYPDSDIYWKKLDDKYHFSCQFT

ADIFAMNHTDFIITSTFQEIAGSKETVGQYESHTAFTLPGLYRVVHGIDVFDPKFNIVSP

GADMSIYFPYTEEKRRLTKFHSEIEELLYSDVENKEHLCVLKDKKKPILFTMARLDRV

KNLSGLVEWYGKNTRLRELANLVVVGGDRRKESKDNEEKAEMKKMYDLIEEYKLN

GQFRWISSQMDRVRNGELYRYICDTKGAFVQPALYEAFGLTVVEAMTCGLPTFATCK

GGPAEIIVHGKSGFHIDPYHGDQAADTLADFFTKCKEDPSHWDEISKGGLQRIEEKYT

WQIYSQRLLTLTGVYGFWKHVSNLDRLEARRYLEMFYALKYRPLAQAVPLAQDD

-continued

HV1-SUS fusion enzyme: DNA Sequence (SEQ ID NO: 8)

ATGGATGGTAACTCCTCCTCCTCGCCGCTGCATGTGGTCATTTGTCCGTGGCTGGC

TCTGGGTCACCTGCTGCCGTGTCTGGATATTGCTGAACGTCTGGCGTCACGCGGCC

ATCGTGTCAGTTTTGTGTCCACCCCGCGCAACATTGCCCGTCTGCCGCCGCTGCGT

CCGGCTGTTGCACCGCTGGTTGATTTCGTCGCACTGCCGCTGCCGCATGTTGACGG

TCTGCCGGAGGGTGCGGAATCGACCAATGATGTGCCGTATGACAAATTTGAACTG

CACCGTAAGGCGTTCGATGGTCTGGCGGCCCCGTTTAGCGAATTTCTGCGTGCAGC

TTGCGCAGAAGGTGCAGGTTCTCGCCCGGATTGGCTGATTGTGGACACCTTTCATC

ACTGGGCGGCGGCGGCGGCGGTGGAAAACAAAGTGCCGTGTGTTATGCTGCTGCT

GGGTGCAGCAACGGTGATCGCTGGTTTCGCGCGTGGTGTTAGCGAACATGCGGCG

GCGGCGGTGGGTAAAGAACGTCCGGCTGCGGAAGCCCCGAGTTTTGAAACCGAAC

GTCGCAAGCTGATGACCACGCAGAATGCCTCCGGCATGACCGTGGCAGAACGCTA

TTTCCTGACGCTGATGCGTAGCGATCTGGTTGCCATCCGCTCTTGCGCAGAATGGG

AACCGGAAAGCGTGGCAGCACTGACCACGCTGGCAGGTAAACCGGTGGTTCCGCT

GGGTCTGCTGCCGCCGAGTCCGGAAGGCGGTCGTGGCGTTTCCAAAGAAGATGCT

GCGGTCCGTTGGCTGGACGCACAGCCGGCAAAGTCAGTCGTGTACGTCGCACTGG

GTTCGGAAGTGCCGCTGCGTGCGGAACAAGTTCACGAACTGGCACTGGGCCTGGA

ACTGAGCGGTGCTCGCTTTCTGTGGGCGCTGCGTAAACCGACCGATGCACCGGAC

GCCGCAGTGCTGCCGCCGGGTTTCGAAGAACGTACCCGCGGCCGTGGTCTGGTTGT

CACGGGTTGGGTGCCGCAGATTGGCGTTCTGGCTCATGGTGCGGTGGCTGCGTTTC

TGACCCACTGTGGCTGGAACTCTACGATCGAAGGCCTGCTGTTCGGTCATCCGCTG

ATTATGCTGCCGATCAGCTCTGATCAGGGTCCGAATGCGCGCCTGATGGAAGGCC

GTAAAGTCGGTATGCAAGTGCCGCGTGATGAATCAGACGGCTCGTTTCGTCGCGA

AGATGTTGCCGCAACCGTCCGCGCCGTGGCAGTTGAAGAAGACGGTCGTCGCGTC

TTCACGGCTAACGCGAAAAAGATGCAAGAAATTGTGGCCGATGGCGCATGCCACG

AACGTTGTATTGACGGTTTTATCCAGCAACTGCGCAGTTACAAGGCGGGTTCTGGT

GCAAACGCTGAACGTATGATAACGCGCGTCCACAGCCAACGTGAGCGTTTGAACG

AAACGCTTGTTTCTGAGAGAAACGAAGTCCTTGCCTTGCTTTCCAGGGTTGAAGCC

AAAGGTAAAGGTATTTTACAACAAAACCAGATCATTGCTGAATTCGAAGCTTTGC

CTGAACAAACCCGGAAGAAACTTGAAGGTGGTCCTTTCTTTGACCTTCTCAAATCC

ACTCAGGAAGCAATTGTGTTGCCACCATGGGTTGCTCTAGCTGTGAGGCCAAGGC

CTGGTGTTTGGGAATACTTACGAGTCAATCTCCATGCTCTTGTCGTTGAAGAACTC

CAACCTGCTGAGTTTCTTCATTTCAAGGAAGAACTCGTTGATGGAGTTAAGAATGG

TAATTTCACTCTTGAGCTTGATTTCGAGCCATTCAATGCGTCTATCCCTCGTCCAAC

ACTCCACAAATACATTGGAAATGGTGTTGACTTCCTTAACCGTCATTTATCGGCTA

AGCTCTTCCATGACAAGGAGAGTTTGCTTCCATTGCTTAAGTTCCTTCGTCTTCACA

GCCACCAGGGCAAGAACCTGATGTTGAGCGAGAAGATTCAGAACCTCAACACTCT

GCAACACACCTTGAGGAAAGCAGAAGAGTATCTAGCAGAGCTTAAGTCCGAAACA

CTGTATGAAGAGTTTGAGGCCAAGTTTGAGGAGATTGGTCTTGAGAGGGGATGGG

GAGACAATGCAGAGCGTGTCCTTGACATGATACGTCTTCTTTTGGACCTTCTTGAG

-continued

GCGCCTGATCCTTGCACTCTTGAGACTTTTCTTGGAAGAGTACCAATGGTGTTCAA

CGTTGTGATCCTCTCTCCACATGGTTACTTTGCTCAGGACAATGTTCTTGGTTACCC

TGACACTGGTGGACAGGTTGTTTACATTCTTGATCAAGTTCGTGCTCTGGAGATAG

AGATGCTTCAACGTATTAAGCAACAAGGACTCAACATTAAACCAAGGATTCTCAT

TCTAACTCGACTTCTACCTGATGCGGTAGGAACTACATGCGGTGAACGTCTCGAGA

GAGTTTATGATTCTGAGTACTGTGATATTCTTCGTGTGCCCTTCAGAACAGAGAAG

GGTATTGTTCGCAAATGGATCTCAAGGTTCGAAGTCTGGCCATATCTAGAGACTTA

CACCGAGGATGCTGCGGTTGAGCTATCGAAAGAATTGAATGGCAAGCCTGACCTT

ATCATTGGTAACTACAGTGATGGAAATCTTGTTGCTTCTTTATTGGCTCACAAACTT

GGTGTCACTCAGTGTACCATTGCTCATGCTCTTGAGAAAACAAAGTACCCGGATTC

TGATATCTACTGGAAGAAGCTTGACGACAAGTACCATTTCTCATGCCAGTTCACTG

CGGATATTTTCGCAATGAACCACACTGATTTCATCATCACTAGTACTTTCCAAGAA

ATTGCTGGAAGCAAAGAAACTGTTGGGCAGTATGAAAGCCACACAGCCTTTACTC

TTCCCGGATTGTATCGAGTTGTTCACGGGATTGATGTGTTTGATCCCAAGTTCAAC

ATTGTCTCTCCTGGTGCTGATATGAGCATCTACTTCCCTTACACAGAGGAGAAGCG

TAGATTGACTAAGTTCCACTCTGAGATCGAGGAGCTCCTCTACAGCGATGTTGAGA

ACAAAGAGCACTTATGTGTGCTCAAGGACAAGAAGAAGCCGATTCTCTTCACAAT

GGCTAGGCTTGATCGTGTCAAGAACTTGTCAGGTCTTGTTGAGTGGTACGGGAAG

AACACCCGCTTGCGTGAGCTAGCTAACTTGGTTGTTGTTGGAGGAGACAGGAGGA

AAGAGTCAAAGGACAATGAAGAGAAAGCAGAGATGAAGAAAATGTATGATCTCA

TTGAGGAATACAAGCTAAACGGTCAGTTCAGGTGGATCTCCTCTCAGATGGACCG

GGTAAGGAACGGTGAGCTGTACCGGTACATCTGTGACACCAAGGGTGCTTTTGTC

CAACCTGCATTATATGAAGCCTTTGGGTTAACTGTTGTGGAGGCTATGACTTGTGG

TTTACCGACTTTCGCCACTTGCAAAGGTGGTCCAGCTGAGATCATTGTGCACGGTA

AATCGGGTTTCCACATTGACCCTTACCATGGTGATCAGGCTGCTGATACTCTTGCT

GATTTCTTCACCAAGTGTAAGGAGGATCCATCTCACTGGGATGAGATCTCAAAAG

GAGGGCTTCAGAGGATTGAGGAGAAATACACTTGGCAAATCTATTCACAGAGGCT

CTTGACATTGACTGGTGTGTATGGATTCTGGAAGCATGTCTCGAACCTTGACCGTC

TTGAGGCTCGCCGTTACCTTGAAATGTTCTATGCATTGAAGTATCGCCCATTGGCT

CAGGCTGTTCCTCTTGCACAAGATGATTAA

*Arabidopsis thaliana* sucrose synthase I: Amino Acid Sequence (SEQ ID NO: 9)

MANAERMITRVHSQRERLNETLVSERNEVLALLSRVEAKGKGILQQNQIIAEFEALPE

QTRKKLEGGPFFDLLKSTQEAIVLPPWVALAVRPRPGVWEYLRVNLHALVVEELQPA

EFLHFKEELVDGVKNGNFTLELDFEPFNASIPRPTLHKYIGNGVDFLNRHLSAKLFHDK

ESLLPLLKFLRLHSHQGKNLMLSEKIQNLNTLQHTLRKAEEYLAELKSETLYEEFEAKF

EEIGLERGWGDNAERVLDMIRLLLDLLEAPDPCTLETFLGRVPMVFNVVILSPHGYFA

QDNVLGYPDTGGQVVYILDQVRALEIEMLQRIKQQGLNIKPRILILTRLLPDAVGTTCG

ERLERVYDSEYCDILRVPFRTEKGIVRKWISRFEVWPYLETYTEDAAVELSKELNGKP

DLIIGNYSDGNLVASLLAHKLGVTQCTIAHALEKTKYPDSDIYWKKLDDKYHFSCQFT

ADIFAMNHTDFIITSTFQEIAGSKETVGQYESHTAFTLPGLYRVVHGIDVFDPKFNIVSP

GADMSIYFPYTEEKRRLTKFHSEIEELLYSDVENKEHLCVLKDKKKPILFTMARLDRV

-continued

KNLSGLVEWYGKNTRLRELANLVVVGGDRRKESKDNEEKAEMKKMYDLIEEYKLN

GQFRWISSQMDRVRNGELYRYICDTKGAFVQPALYEAFGLTVVEAMTCGLPTFATCK

GGPAEIIVHGKSGFHIDPYHGDQAADTLADFFTKCKEDPSHWDEISKGGLQRIEEKYT

WQIYSQRLLTLTGVYGFWKHVSNLDRLEARRYLEMFYALKYRPLAQAVPLAQDD

*Arabidopsis thaliana* sucrose synthase I: DNA Sequence
(SEQ ID NO: 10)

ATGGCAAACGCTGAACGTATGATTACCCGTGTCCACTCCCAACGCGAACGCCTGA

ACGAAACCCTGGTGTCGGAACGCAACGAAGTTCTGGCACTGCTGAGCCGTGTGGA

AGCTAAGGGCAAAGGTATTCTGCAGCAAAACCAGATTATCGCGGAATTTGAAGCC

CTGCCGGAACAAACCCGCAAAAAGCTGGAAGGCGGTCCGTTTTTCGATCTGCTGA

AATCTACGCAGGAAGCGATCGTTCTGCCGCCGTGGGTCGCACTGGCAGTGCGTCC

GCGTCCGGGCGTTTGGGAATATCTGCGTGTCAACCTGCATGCACTGGTGGTTGAAG

AACTGCAGCCGGCTGAATTTCTGCACTTCAAGGAAGAACTGGTTGACGGCGTCAA

AAACGGTAATTTTACCCTGGAACTGGATTTTGAACCGTTCAATGCCAGTATCCCGC

GTCCGACGCTGCATAAATATATTGGCAACGGTGTGGACTTTCTGAATCGCCATCTG

AGCGCAAAGCTGTTCCACGATAAAGAATCTCTGCTGCCGCTGCTGAAATTCCTGCG

TCTGCATAGTCACCAGGGCAAGAACCTGATGCTGTCCGAAAAAATTCAGAACCTG

AATACCCTGCAACACACGCTGCGCAAGGCGGAAGAATACCTGGCCGAACTGAAAA

GTGAAACCCTGTACGAAGAATTCGAAGCAAAGTTCGAAGAAATTGGCCTGGAACG

TGGCTGGGGTGACAATGCTGAACGTGTTCTGGATATGATCCGTCTGCTGCTGGACC

TGCTGGAAGCACCGGACCCGTGCACCCTGGAAACGTTTCTGGGTCGCGTGCCGAT

GGTTTTCAACGTCGTGATTCTGTCCCCGCATGGCTATTTTGCACAGGACAATGTGC

TGGGTTACCCGGATACCGGCGGTCAGGTTGTCTATATTCTGGATCAAGTTCGTGCG

CTGGAAATTGAAATGCTGCAGCGCATCAAGCAGCAAGGCCTGAACATCAAACCGC

GTATTCTGATCCTGACCCGTCTGCTGCCGGATGCAGTTGGTACCACGTGCGGTGAA

CGTCTGGAACGCGTCTATGACAGCGAATACTGTGATATTCTGCGTGTCCCGTTTCG

CACCGAAAAGGGTATTGTGCGTAAATGGATCAGTCGCTTCGAAGTTTGGCCGTATC

TGGAAACCTACACGGAAGATGCGGCCGTGGAACTGTCCAAGGAACTGAATGGCAA

ACCGGACCTGATTATCGGCAACTATAGCGATGGTAATCTGGTCGCATCTCTGCTGG

CTCATAAACTGGGTGTGACCCAGTGCACGATTGCACACGCTCTGGAAAAGACCAA

ATATCCGGATTCAGACATCTACTGGAAAAAGCTGGATGACAAATATCATTTTTCGT

GTCAGTTCACCGCGGACATTTTTGCCATGAACCACACGGATTTTATTATCACCAGT

ACGTTCCAGGAAATCGCGGGCTCCAAAGAAACCGTGGGTCAATACGAATCACATA

CCGCCTTCACGCTGCCGGGCCTGTATCGTGTGGTTCACGGTATCGATGTTTTTGAC

CCGAAATTCAATATTGTCAGTCCGGGCGCGGATATGTCCATCTATTTTCCGTACAC

CGAAGAAAAGCGTCGCCTGACGAAATTCCATTCAGAAATTGAAGAACTGCTGTAC

TCGGACGTGGAAAACAAGGAACACCTGTGTGTTCTGAAAGATAAAAAGAAACCG

ATCCTGTTTACCATGGCCCGTCTGGATCGCGTGAAGAATCTGTCAGGCCTGGTTGA

ATGGTATGGTAAAAACACGCGTCTGCGCGAACTGGCAAATCTGGTCGTGGTTGGC

GGTGACCGTCGCAAGGAATCGAAAGATAACGAAGAAAAGGCTGAAATGAAGAAA

ATGTACGATCTGATCGAAGAATACAAGCTGAACGGCCAGTTTCGTTGGATCAGCT

-continued

```
CTCAAATGGACCGTGTGCGCAATGGCGAACTGTATCGCTACATTTGCGATACCAA

GGGTGCGTTTGTTCAGCCGGCACTGTACGAAGCTTTCGGCCTGACCGTCGTGGAAG

CCATGACGTGCGGTCTGCCGACCTTTGCGACGTGTAAAGGCGGTCCGGCCGAAAT

TATCGTGCATGGCAAATCTGGTTTCCATATCGATCCGTATCACGGTGATCAGGCAG

CTGACACCCTGGCGGATTTCTTTACGAAGTGTAAAGAAGACCCGTCACACTGGGA

TGAAATTTCGAAGGGCGGTCTGCAACGTATCGAAGAAAAATATACCTGGCAGATT

TACAGCCAACGCCTGCTGACCCTGACGGGCGTCTACGGTTTTTGGAAACATGTGTC

TAATCTGGATCGCCTGGAAGCCCGTCGCTATCTGGAAATGTTTTACGCACTGAAGT

ATCGCCCGCTGGCACAAGCCGTTCCGCTGGCACAGGACGACTAA
```

TABLE 1

$^1H$ and $^{13}C$ NMR spectral data (chemical shifts and coupling constants) for R7-2 compound [a-c].

| Position | $^1H$ NMR | $^{13}C$ NMR |
|---|---|---|
| 1 | 0.75 t (12.8), 1.78 m | 40.0 |
| 2 | 1.65 m, 2.02 m | 19.8 |
| 3 | 1.08 m, 2.27 m | 38.7 |
| 4 | — | 44.5 |
| 5 | 1.06 d (13.2) | 57.6 |
| 6 | 2.27 m, 2.42 m | 23.7 |
| 7 | 1.42 m, 1.76 m | 42.8 |
| 8 | — | 41.4 |
| 9 | 0.91 d (7.7) | 54.5 |
| 10 | — | 40.5 |
| 11 | 1.66 m, 1.74 m | 20.4 |
| 12 | 2.26 m, 2.74 d (13.3) | 38.7 |
| 13 | — | 87.6 |
| 14 | 2.02 m, 2.72 m | 43.9 |
| 15 | 1.88 m, 2.02 m | 46.6 |
| 16 | — | 153.2 |
| 17 | 5.00 s, 5.74 s | 105.5 |
| 18 | 1.33 s | 28.4 |
| 19 | — | 177.2 |
| 20 | 1.39 s | 17.0 |
| 1' | 6.40 d (8.1) | 95.2 |
| 2' | 4.45 m | 76.8 |
| 3' | 5.16 m | 88.7 |
| 4' | 4.14 m | 70.3 |
| 5' | 4.16 m | 77.7 |
| 6' | 4.04 m, 4.28 m | 62.3 |
| 1'' | 5.43 d (7.7) | 96.2 |
| 2'' | 3.98 m | 81.4 |
| 3'' | 4.96 m | 87.9 |
| 4'' | 4.12 m | 70.4 |
| 5'' | 3.92 m | 78.1 |
| 6'' | 4.24 m, 4.58 m | 69.8 |
| 1''' | 5.35 d (8.1) | 103.9 |
| 2''' | 4.14 m | 75.8 |
| 3''' | 4.16 m | 78.6 |
| 4''' | 3.96 m | 73.4 |
| 5''' | 3.73 ddd (2.8, 6.3, 9.2) | 78.2 |
| 6''' | 4.33 m, 4.53 m | 64.2 |
| 1'''' | 5.38 dd (7.7, 4.2) | 104.2 |
| 2'''' | 3.91 m | 75.9 |
| 3'''' | 4.04 m | 78.1 |
| 4'''' | 4.10 m | 71.9 |
| 5'''' | 3.88 m | 78.6 |
| 6'''' | 4.15 m, 4.27 m | 63.0 |
| 1''''' | 5.05 d (7.4) | 106.2 |
| 2''''' | 3.92 m | 75.6 |
| 3''''' | 4.06 m | 78.0 |
| 4''''' | 4.16 m | 73.8 |
| 5''''' | 3.89 m | 78.0 |
| 6''''' | 4.18 m, 4.48 m | 62.5 |
| 1'''''' | 5.82 d (6.3) | 104.3 |
| 2'''''' | 4.01 m | 75.7 |
| 3'''''' | 4.18 m | 78.3 |
| 4'''''' | 4.20 m | 71.6 |
| 5'''''' | 3.96 m | 78.7 |
| 6'''''' | 4.06 m, 4.32 m | 62.0 |
| 1''''''' | 4.99 d (7.6) | 106.2 |
| 2''''''' | 4.01 m | 77.1 |
| 3''''''' | 4.17 m | 78.1 |
| 4''''''' | 4.23 m | 71.4 |
| 5''''''' | 3.92 m | 78.7 |
| 6''''''' | 4.03 m, 4.28 m | 64.2 |

[a] assignments made based on TOCSY, HSQC, ROESY and HMBC correlations;
[b] Chemical shift values are in δ (ppm);
[c] Coupling constants are in Hz.

TABLE 2

$^1H$ and $^{13}C$ NMR spectral data (chemical shifts and coupling constants) for R6-1 produced by enzymatic bioconversion [a-c].

| Position | $^1H$ NMR | $^{13}C$ NMR |
|---|---|---|
| 1 | 0.74 t (12.4), 1.85 m | 40.4 |
| 2 | 1.45 m, 2.18 m | 19.8 |
| 3 | 1.09 m, 2.16 m | 37.4 |
| 4 | — | 42.1 |
| 5 | 0.98 d (12.4) | 57.2 |
| 6 | 1.90 m, 2.14 m | 21.8 |
| 7 | 1.73 m, 2.48 m | 43.9 |
| 8 | — | 41.5 |
| 9 | 0.88 d (6.3) | 53.7 |
| 10 | — | 37.4 |
| 11 | 1.66 m, 2.12 m | 20.4 |
| 12 | 1.90 m, 2.87 d (12.3) | 39.5 |
| 13 | — | 86.2 |
| 14 | 1.73 d (11.1), 2.48 d (10.7) | 44.1 |
| 15 | 2.08 m, 2.11 m | 47.5 |
| 16 | — | 153.9 |
| 17 | 5.01 s, 5.64 s | 104.5 |
| 18 | 1.48 s | 29.0 |
| 19 | — | 175.5 |
| 20 | 1.12 s | 16.7 |
| 1' | 6.36 d (7.6) | 92.8 |
| 2' | 4.15 m | 82.0 |
| 3' | 4.54 m | 78.2 |
| 4' | 4.14 m | 71.7 |
| 5' | 4.16 m | 78.8 |
| 6' | 4.18 m, 4.35 m | 61.3 |
| 1'' | 5.04 d (7.6) | 97.8 |
| 2'' | 4.23 m | 80.4 |
| 3'' | 4.05 m | 85.2 |
| 4'' | 4.04 m | 70.8 |
| 5'' | 3.96 m | 77.8 |
| 6'' | 4.22 m, 4.36 m | 61.9 |
| 1''' | 5.05 d (7.4) | 104.4 |

TABLE 2-continued

$^1$H and $^{13}$C NMR spectral data (chemical shifts and coupling constants) for R6-1 produced by enzymatic bioconversion [a-c].

| Position | $^1$H NMR | $^{13}$C NMR |
|---|---|---|
| 2''' | 4.08 m | 76.1 |
| 3''' | 4.12 m | 78.9 |
| 4''' | 4.02 m | 69.6 |
| 5''' | 3.66 ddd (2.8, 6.4, 9.4) | 77.6 |
| 6''' | 4.32 m, 4.54 m | 62.7 |
| 1'''' | 5.24 d (7.6) | 106.0 |
| 2'''' | 4.04 m | 76.4 |
| 3'''' | 4.40 m | 77.3 |
| 4'''' | 4.19 m | 71.3 |
| 5'''' | 4.00 m | 77.2 |
| 6'''' | 4.20 m, 4.32 m | 62.5 |
| 1''''' | 5.37 t (7.4) | 103.6 |
| 2''''' | 4.28 m | 87.7 |
| 3''''' | 4.35 m | 77.0 |
| 4''''' | 4.24 m | 74.9 |
| 5''''' | 3.92 ddd (2.8, 6.4, 9.9) | 77.8 |
| 6''''' | 4.26 m, 4.51 m | 62.1 |
| 1'''''' | 5.57 d (7.7) | 104.6 |
| 2'''''' | 4.03 m | 77.1 |
| 3'''''' | 4.38 m | 78.8 |
| 4'''''' | 4.26 m | 71.2 |
| 5'''''' | 3.96 ddd (2.1, 6.4, 9.4) | 77.8 |
| 6'''''' | 4.06 m, 4.36 m | 62.0 |

[a] assignments made based on TOCSY, HSQC, ROESY and HMBC correlations;
[b] Chemical shift values are in δ (ppm);
[c] Coupling constants are in Hz.

TABLE 3

$^1$H and $^{13}$C NMR spectral data (chemical shifts and coupling constants) for R6-4 (R6-4A/R6-4B) compound [a-c].

| Position | $^1$H NMR (R6-4A/R6-4B) | $^{13}$C NMR (R6-4A/R6-4B) |
|---|---|---|
| 1 | 0.73 t (12.8), 1.65 m | 40.0 |
| 2 | 1.42 m, 2.12 m | 20.4/20.3 |
| 3 | 1.13 m, 2.90 d (13.2)/ 1.11 m, 2.86 m | 38.0 |
| 4 | — | 44.7 |
| 5 | 0.97 d (12.2) | 57.9 |
| 6 | 1.66 m, 2.09 m | 22.4 |
| 7 | 1.25 m, 1.70 m | 42.9 |
| 8 | — | 42.0 |
| 9 | 0.88 br s | 54.3 |
| 10 | — | 41.0 |
| 11 | 1.68 m | 20.9 |
| 12 | 1.12 m, 2.12 m | 37.5 |
| 13 | — | 86.3/86.8 |
| 14 | 1.75 m, 2.45 d (11.3) | 44.7 |
| 15 | 2.02 m, 2.12 m | 48.2/48.1 |
| 16 | — | 155.0/154.8 |
| 17 | 5.05/5.03 s, 5.67/5.65 s | 105.0/105.2 |
| 18 | 1.49/1.46 s | 29.7/29.6 |
| 19 | — | 176.0/176.1 |
| 20 | 1.09/1.13 s | 17.1/17.2 |
| 1' | 6.35 d (7.7)/6.44 d (7.3) | 93.4/93.6 |
| 2' | 3.97 | 82.6/81.6 |
| 3' | 4.25 m | 78.4 |
| 4' | 4.22 m | 71.6 |
| 5' | 3.74 m | 79.6 |
| 6' | 4.12 m, 4.55 m | 62.7 |
| 1'' | 5.12 d (7.6)/5.07 d (7.4)/ | 98.1/98.3 |
| 2'' | 4.03 m | 85.4/85.2 |
| 3'' | 4.32 m | 78.3 |
| 4'' | 4.15 m | 70.1 |
| 5'' | 3.88 m | 78.5 |
| 6'' | 4.18 m, 4.42 m | 62.8/62.6 |
| 1''' | 5.33 d (7.8)/5.46 d (7.8)/ | 104.2/104.9 |
| 2''' | 4.12 m | 85.5/77.7 |
| 3''' | 4.28 m | 78.2 |
| 4''' | 4.14 m | 71.5/71.9 |
| 5''' | 3.92 m | 79.4/77.8 |

TABLE 3-continued

$^1$H and $^{13}$C NMR spectral data (chemical shifts and coupling constants) for R6-4 (R6-4A/R6-4B) compound [a-c].

| Position | $^1$H NMR (R6-4A/R6-4B) | $^{13}$C NMR (R6-4A/R6-4B) |
|---|---|---|
| 6''' | 4.17 m, 4.48 m | 63.2/63.4 |
| 1'''' | 5.48 d (7.9)/5.42 d (7.6) | 106.3/105.1 |
| 2'''' | 4.10 m | 85.6 |
| 3'''' | 4.19 m | 78.2 |
| 4'''' | 4.30 m | 71.3/71.0 |
| 5'''' | 3.96 m | 79.4 |
| 6'''' | 4.22 m, 4.54 m | 62.8 |
| 1''''' | 5.28 d (7.5)/5.38 d (7.5)/ | 106.6/106.4 |
| 2''''' | 4.06 m | 77.1/86.4 |
| 3''''' | 4.20 m | 78.0 |
| 4''''' | 4.32 m | 70.8/71.2 |
| 5''''' | 3.98 m | 77.9 |
| 6''''' | 4.16 m, 4.43 m | 62.7 |
| 1'''''' | 5.40 d (7.5)/5.58 d (7.5)/ | 104.3/105.0 |
| 2'''''' | 4.08 m | 76.7 |
| 3'''''' | 4.32 m | 78.0 |
| 4'''''' | 4.17 m | 72.0 |
| 5'''''' | 3.98 m | 77.8 |
| 6'''''' | 4.12 m, 4.49 m | 62.8 |

[a] assignments made based on TOCSY, HSQC, ROESY and HMBC correlations;
[b] Chemical shift values are in δ (ppm);
[c] Coupling constants are in Hz.

STATEMENT OF INDUSTRIAL APPLICABILITY/TECHNICAL FIELD

This disclosure has applicability in the food, feed, beverage, and pharmacological industries. This disclosure relates generally to a method for the biosynthetic production of certain steviol glycosides via enzymes and/or modified microbial strain(s) and potential uses thereof as a sweetener for food products and beverages as well as related compositions.

REFERENCES

1. Bedir, E. et al., (2001), *A new dammarane type triterpene glycoside from Polyscias fulva*. J. Natural Products, (64): 95-97.
2. Brandle, J. E. et al., (1998). *Stevia Rebaudiana: Its Agricultural, Biological, and Chemical Properties*, Canadian J. Plant Science. 78 (4): 527-36.
3. Ceunen, S., and J. M. C. Geuns, *Steviol Glycosides: Chemical Diversity, Metabolism, and Function*, J. Nat. Prod., 2013, 76 (6), pp 1201-28 (2013).
4. Chaturvedula, V. S. P. et al., (2003), *New cytotoxic oleanane saponis from the infructescences of Polyscias amplifolia from the Madagascar rainforest*. Planta Medica, (69): 440-44.
5. Daugherty, A. B., et al., *Structural and Functional Consequences of Circular Permutation on the Active Site of Old Yellow Enzyme*, ACS Catal. (2015) 5:892-99.
6. Du J et al., (2011), *Engineering microbial factories for synthesis of value-added products*, J Ind Microbiol. Biotechnol. 38: 873-90.
7. GRAS Notices, USA Food and Drug Administration, United States Health & Human Services. (2016) (relevant to steviol glycosides & polyglycosides).
8. Huan, V. D. et al., (1998). *Oleanane saponins from Polyscias fructicosa*. Phytochemistry, (47):451-57.
9. Häusler A, and Münch T., (1997), *Microbial Production of Natural Flavors*, ASM News (63): 551-59.
10. Mao, G. et al., (2017), *Enzymatic Synthesis and Structural Characterization of Rebaudioside D3, a Minor Steviol Glycoside of Stevia rebaudiana Bertoni*, Amer. J. Plant Sciences, (8): 441-50.

11. Ohtani, K., et al., (1992). *Minor diterpene glycosides from sweet leaves of Rubus Suavissimus*, PHYTOCHEMISTRY, (31): 1553-59.

12. Prakash I., et al.; *Isolation and Characterization of a Novel Rebaudioside M Isomer from a Bio conversion Reaction of Rebaudioside A and NMR Comparison Studies of Rebaudioside M Isolated from Stevia rebaudiana Bertoni and Stevia rebaudiana Morita*, BIOMOLECULES, 2014 June; 4(2): 374-89. (Published online 2014 Mar. 31, 2014).

13. Prakash I., et al., *Development of Next Generation Stevia Sweetener: Rebaudioside M*, FOODS, (2014), 3:162-175.

14. Qian, Z. et al., *Improving the catalytic activity of Candida antarctica lipase B by circular permutation*, J. OF THE AMERICAN CHEMICAL SOCIETY. (2005) 127(39): 13466-13467.

15. Richman A, et. al., *Functional genomics uncovers three glucosyltransferases involved in the synthesis of the major sweet glucosides of Stevia rebaudiana*, PLANT J. (2005) January; 41(1):56-67.

16. Shockey J. M. et al., (2003), *Arabidopsis contains a large superfamily of acyl-activating enzymes: phylogenetic and biochemical analysis reveals a new class of acyl-coenzyme A synthetases*. PLANT PHYSIOL. 132 1065-76.

17. Tanaka, T. et al., (2007), *Facile discrimination of aldose enantiomers by reversed-phase HPLC*, CHEM. PHARM. BULL., (55): 899-901.

18. Topell, S. et al., *Circularly permuted variants of the green fluorescent protein*, FEBS LETTERS. (1999) 457(2): 283-89.

19. Wang J., et al., *Pathway mining-based integration of critical enzyme parts for de novo biosynthesis of steviol glycosides sweetener in Escherichia coli*, CELL RESEARCH (2016) 26:258-61.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, patent application publication, and database entry was specifically and individually incorporated herein by reference. In case of conflict, the present application, including any definitions herein, will control.

What is claimed is:

1. A method of producing rebaudioside R6-2A and/or R6-2B, the method comprising:

(I) preparing a reaction mixture comprising:

(i) rebaudioside D3;

(ii) one or more substrates selected from the group consisting of sucrose, uridine diphosphate (UDP), uridine diphosphate-glucose (UDP-glucose), and combinations thereof; and (iii) an enzyme selected from the group consisting of:

(a) a UDP-glycosyltransferase (UGT);

(b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain; and (II) incubating the reaction mixture for a sufficient time to produce rebaudioside R6-2A and/or R6-2B; wherein the UDP-glycosyltransferase is at least 90% identical to the amino acid sequence of SEQ ID NO: 1 or 3;

wherein the UDP-glycosyltransferase fusion enzyme is at least 90% identical to the amino acid sequence of SEQ ID NO: 5 or 7;

wherein the rebaudioside D3 has the structure of:

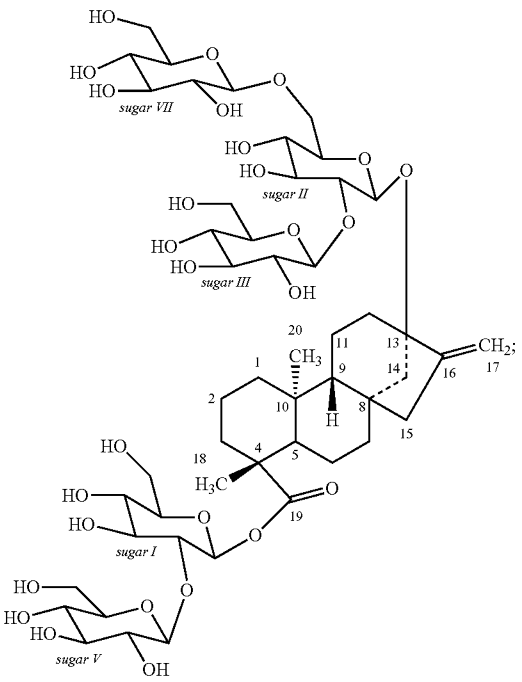

the rebaudioside R6-2A has the structure of:

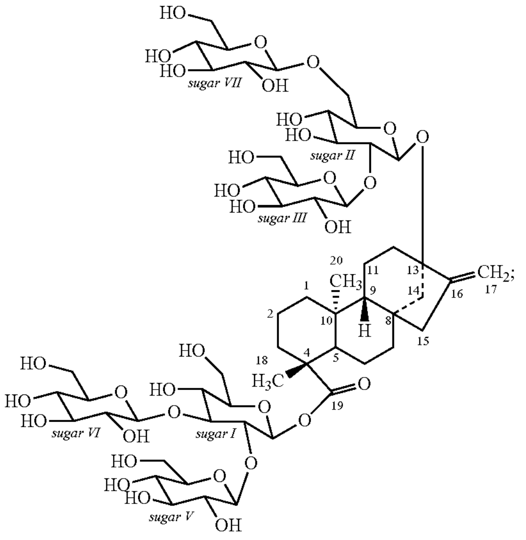

and the rebaudioside R6-2B has the structure of:

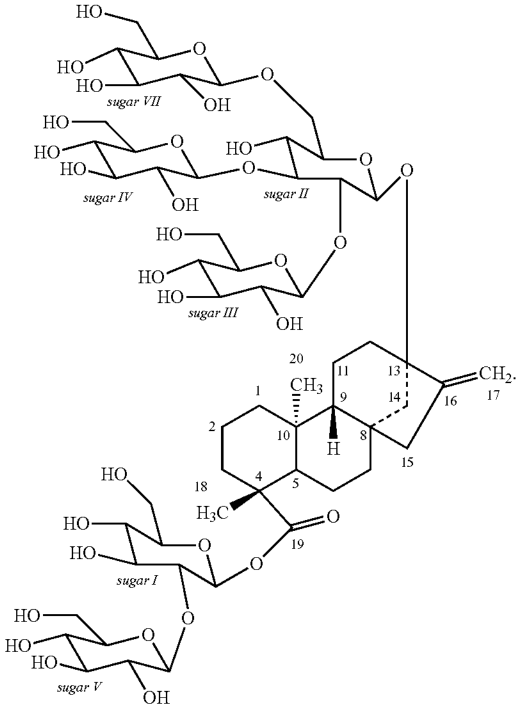

2. The method of claim 1, wherein the sucrose synthase or sucrose synthase domain is selected from the group consisting of an *Arabidopsis* sucrose synthase I, an *Arabidopsis* sucrose synthase 3 and a *Vigna* radiate sucrose synthase.

3. The method of claim 1, wherein the UDP-glycosyltransferase comprises the amino acid sequence of SEQ ID NOs: 1 or 3.

4. The method of claim 1, further comprising producing rebaudioside D3 by incubating rebaudioside E with a UDP-glycosyltransferase and a substrate selected from the group consisting of sucrose, UDP, UDP-glucose, and combinations thereof.

5. A method of producing rebaudioside R6-1, the method comprising:

(I) preparing a reaction mixture comprising:

(i) rebaudioside D;

(ii) one or more substrates selected from the group consisting of sucrose, uridine diphosphate (UDP), uridine diphosphate-glucose (UDP-glucose), and combinations thereof; and (iii) an enzyme selected from the group consisting of:

(a) a UDP-glycosyltransferase (UGT), wherein the UDP-glycosyltransferase is at least 90% identical to the amino acid sequence of SEQ ID NO: 3;

(b) a UDP-glycosyltransferase and a sucrose synthase separately added to the reaction mixture; and (c) a UDP-glycosyltransferase fusion enzyme comprising a UDP-glycosyltransferase domain coupled to a sucrose synthase domain, wherein the UDP-glycosyltransferase fusion enzyme is at least 90% identical to the amino acid sequence of SEQ ID NO: 7; and (II) incubating the reaction mixture for a sufficient time to produce rebaudioside R6-1;

wherein the rebaudioside D has the structure of:

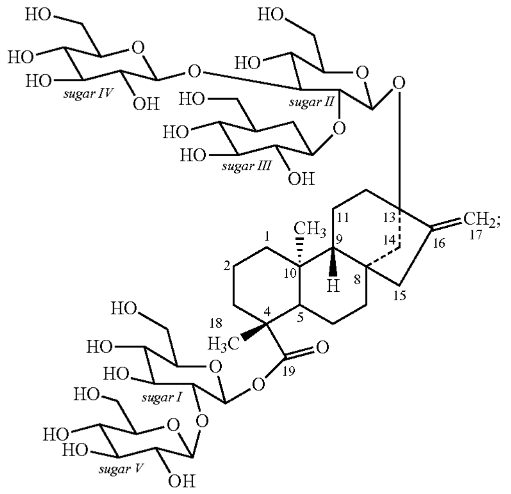

and the rebaudioside R6-1 has the structure of:

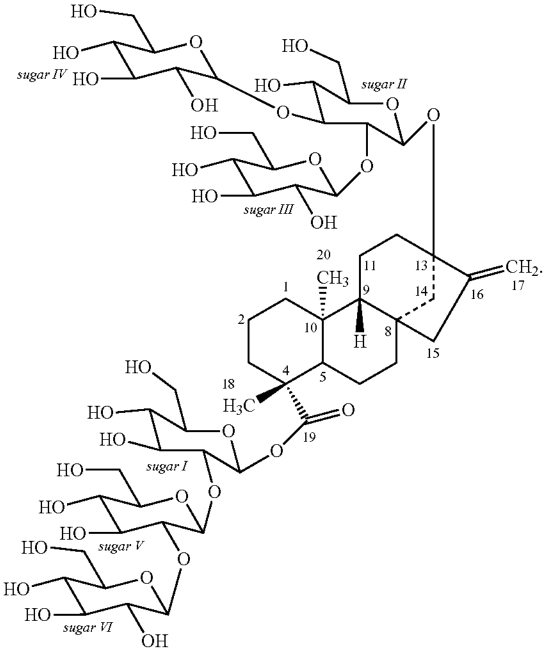

6. The method of claim 5, wherein the sucrose synthase or sucrose synthase domain is selected from the group consisting of an *Arabidopsis* sucrose synthase I, an *Arabidopsis* sucrose synthase 3 and a *Vigna* radiate sucrose synthase.

7. The method of claim 5, wherein the UDP-glycosyltransferase comprises the amino acid sequence of SEQ ID NO: 3.

8. The method of claim 5, wherein the UDP-glycosyltransferase fusion enzyme comprises the amino acid sequence of SEQ ID NO: 7.

9. The method of claim 5, further comprising producing rebaudioside D by incubating rebaudioside E and/or rebaudioside A with a UDP-glycosyltransferase and a substrate selected from the group consisting of sucrose, UDP, UDP-glucose, and combinations thereof.

10. The method of claim 1, wherein the reaction mixture is in vitro.

11. The method of claim 1, wherein the reaction mixture is a cell-based reaction mixture.

* * * * *